(12) United States Patent
McCormick et al.

(10) Patent No.: US 7,514,549 B2
(45) Date of Patent: Apr. 7, 2009

(54) TUMOR INHIBITION BY MODULATING SPROUTY EXPRESSION OR ACTIVITY

(75) Inventors: J. Justin McCormick, Port Austin, MI (US); Lito Piro, Okemos, MI (US)

(73) Assignee: Michigan State University, East Lansing, MI (US)

( * ) Notice: Subject to any disclaimer, the term of this patent is extended or adjusted under 35 U.S.C. 154(b) by 22 days.

(21) Appl. No.: 11/404,766

(22) Filed: Apr. 17, 2006

(65) Prior Publication Data
US 2007/0066522 A1 Mar. 22, 2007

Related U.S. Application Data

(60) Provisional application No. 60/671,783, filed on Apr. 16, 2005.

(51) Int. Cl.
*C07H 21/02* (2006.01)
*C07H 21/04* (2006.01)
(52) U.S. Cl. .............. 536/24.5; 536/23.1; 536/24.3; 536/24.33
(58) Field of Classification Search ............... 536/23.1, 536/24.3, 24.33, 24.5
See application file for complete search history.

(56) References Cited

OTHER PUBLICATIONS

Tsavachidou et al. SPRY2 is an inhibitor of the Ras/extracellular signal-regulated kinase pathway in melanocytes and melanoma cells with wild-type BRAF but not with the V599E mutant. Cancer Research, 2004 vol. 64:5556-559.*
GenBank Accession No. AF039843, Feb. 25, 1998.*
Elbashir et al. Analysis of gene function in somatic mammalian cells using small interfering RNAs. Methods, 2002 vol. 26:199-213.*
Burridge, K. et al., "Rho and RAC Take Center Stage", Cell, vol. 116, pp. 167-179, Jan. 23, 2004.
Casco, T. et al., "Sprouty, an Intracellular Inhibitor of Ras Signaling", Cell, vol. 96, pp. 655-665, Mar. 5, 1999.
Chen, X. et al., "Activation of Mitogen-activated Protein Kinase by Membrane-targeted Raf Chimeras Is Independent of Raft Localization", The Journal of Biological Chemistry, vol. 276, No. 37, pp. 34617-34623, issue of Sep. 14, 2001.
Christofori, G., "Split personalities: the agonistic antagonis Sprouty", Nature Cell Biology, vol. 5, pp. 377-379, May 2003.
De Maximy, A. A. et al., "Cloning and expression pattern of a mouse homologue of *Drosophila sprouty* in the mouse embryo", Mechanisms of Development, vol. 81, pp. 213-216, 1999.
Egan, J. E. et al., "The bimodal regulation of epidermal growth factor signaling by human Sprouty proteins", PNAS, vol. 99, No. 9, pp. 6041-6046, Apr. 30, 2002.

(Continued)

*Primary Examiner*—Sean McGarry
*Assistant Examiner*—Terra C. Gibbs
(74) *Attorney, Agent, or Firm*—Wilmer Cutler Pickering Hale and Dorr LLP

(57) ABSTRACT

Methods are provided for identifying compounds that decrease the expression or activity of an overexpressed Sprouty protein in certain cancers. Such compounds can be useful for treating cancers in which a Sprouty protein is overexpressed. Also provided are therapeutic formulations and pharmaceutical formulations for treating cancers characterized by overexpression of a Sprouty protein.

10 Claims, 17 Drawing Sheets

OTHER PUBLICATIONS

Franke, T. F. et al., "PI3K/Akt and apoptosis: size matters", Oncogene, vol. 22, pp. 8983-8998, 2003.

Gross, I. et al., "Mammalian Sprouty Proteins Inhibit Cell Growth and Differentiation by Preventing Ras Activation", The Journal of Biological Chemistry, vol. 276, No. 49, pp. 46460-46468, Dec. 7, 2001.

Guy, G. R. et al., "Sprouty: how does the branch manager work", Journal of Cell Science, vol. 116, No. 15, pp. 3061-3068, 2003.

Hacohen, N. et al., "*sprouty* Encodes a Novel Antagonist of FGF Signaling that Patterns Apical Branching of the *Drosophila* Airways", Cell, vol. 92, pp. 253-263, Jan. 23, 1998.

Haglund, K. et al., "Sprouty2 acts at the Cbl/CIN85 interface to inhibit epidermal growth factor receptor downregulation", EMBO Reports, vol. 6, No. 7, pp. 635-641, 2005.

Hanafusa, H. et al., "Sprouty1 and Sprouty2 provide a control mechanism for the Ras/MAPL signaling pathway", Nature Cell Biology, vol. 4, pp. 850-858, Nov. 2002.

Impagnatiello, M. A. et al., "Mammalian Sprouty-1 and -2 Are Membrame-anchored Phosphoprotein Inhibitors of Growth Factor Signaling in Endothelial Cells", The Journal of Cell Biology, vol. 152, No. 5, pp. 1087-1098, Mar. 5, 2001.

International Search Authority, International Search Report for PCT/US06/14334, mailed May 15, 2007, 5 pages.

Kim, HJ et al., "Modulation of signaling by Sprouty: a developing story", Nat. Rev. Mol. Cell Biol., vol. 5, No. 6, pp. 441-450, Jun. 2004.

Lakin, N. D. et al., "Regulation of p53 in response to DNA damage", Oncogene, vol. 18, pp. 7644-7655, 1999.

Lambert, J. M. et al., "Tiam1 mediates Ras activation of Rac by a PI(3)K-independent mechanism", Nature Cell Biology, vol. 4, pp. 621-625, Aug. 2002.

Levitzki, A. et al., "Tyrosine Kinase Inhibition: An Approach to Drug Development", Science, vol. 267, pp. 17821788, Mar. 24, 1995.

Levkowitz, G. et al., "Ubiquitin Ligase Activity and Tyrosine Phosphorylation Underlie Suppression of Growth Factor Signaling by c-Cbl/Sli-1", Molecular Cell. vol. 4, pp. 1029-1040, Dec. 1999.

Mason, J. M. et al., "Tyrosine Phosphorylation of Sprouty Proteins Regulates Their Ability to Inhibit Growth Factor Signaling: A Dual Feedback Loop", Molecular Biology of the Cell, vol. 15, pp. 2176-2188, May 2004.

Medema, R. H. et al., "The Role of p21ras in Receptor Tyrosine Kinase Signaling", Critical Reviews in Oncogenesis, vol. 4, No. 6, pp. 615-661, 1993.

Miller, W. E. et al., "The Epstein-Barr Virus Latent Membrane Protein 1 Induces Expression of the Epidermal Growth Factor Receptor", Journal of Virology, vol. 69, No. 7, pp. 4390-4398, Jul. 1995.

Minowada, G. et al., "Vertebrate Sprouty genes are induced by FGF signaling and can cause chondrodysplasia when overexpressed", Development, vol. 126, pp. 4465-4475, 1999.

Murga, C. et al., "Rac1 and RhoG promote cell survival by the activation of PI3K and Akt, independently of their ability to stimulate JNK and NF-κB". Oncogene, vol. 21, pp. 207-216, 2002.

Ogawara, Y. et al., "Akt Enhances Mdm2-mediated Ubiquitination and Degradation of p53", The Journal of Biological Chemistry, vol. 277, No. 24, pp. 21843-21850, Issue of Jun. 14, 2002.

Okano, J. et al., "Akt/Protein Kinase B Isoforms Are Differentlially Regulated by Epidermal Growth Factor Stimulation", The Journal of Biological Chemistry, vol. 275, No. 40, pp. 30934-30942, Issue of Oct. 6, 2000.

Rubin, C. et al., "Sprouty Fine-Tunes EGF Signaling through Interlinked Positive and Negative Feedback Loops", Current Biology, vol. 13, pp. 297-307, Feb. 18, 2003.

Sasaki, A. et al., "Mammalian Sprouty4 suppresses Ras-indepdent ERK activation by binding to Raf1", Nat. Cell Biol., vol. 5, No. 5, pp. 427-432, May 2003.

Shields, J. M. et al., "Understanding Ras: 'it ain't over 'til it's over'", trends in Cell Biology, vol. 10, pp. 147-154, Apr. 2000.

Sithanandam, G. et al., "Alternate Paths from Epidermal Growth Factor Receptor to Akt in Malignant Versus Nontransformed Lung Epithelial Cells", American Journal of Respiratory Cell and Molecular Biology, vol. 33, pp. 490-499, 2005.

Stein, R. C. et al., "PI3-kinase inhibition: a target for drug development?", Molecular Medicine Today, vol. 6, pp. 347-357, Sep. 2000.

Suzuki-Hirano, A. et al., Regulation of isthmic Fgf8 signal by *spourty2*, Development, vol. 132, pp. 257-265, 2005.

Tefft, J. D. et al., "Conserved function of *mSpry-2*, a murine homolog of *Drosophila sprouty*, which negatively modulates respiratory organogenesis", Current Biology, vol. 9, No. 4, pp. 219-222, Feb. 15, 1999.

Thien, C. B. F. et al., "CBL: Many Adaptations to Regulate Protein Tyrosine Kinases", Nature Reviews, Molecular Cell Biology, vol. 2, pp. 294-305, Apr. 2001.

Tiganis, T. et al., "The Protein-tyrosine Phosphatase TCPTP Regulates Epidermal Growth Factor Receptor-mediated and Phosphatidylinositol 3-Kinase-dependent Signaling", The Journal of Biological Chemistry, vol. 274, No. 39, pp. 27768-27775, Sep. 24, 1999.

Wang, H. Q. et al., "Epidermal Growth Factor Receptor-dependent, NF-κB-independent Activation of the Phosphatidylinositol 3-Kinase/Akt Pathway Inhibits Ultraviolet Irradiation-induced Caspases-3, -8, and -9 in Human Keratinocytes", The Journal of Biological Chemistry, vol. 278, No. 46, pp. 45737-45745, Nov. 14, 2003.

Wong, E. S. M. et al., "Evidence for Direct Interaction between Sprouty and Cbl", The Journal of Biological Chemistry, vol. 276, No. 8, pp. 5866-5875, Issue of Feb. 23, 2001.

Wong, E. S. M. et al., "Sprouty2 attenuates epidermal growth factor receptor ubiquitylation and endocytosis, and consequently enhances Ras/ERK signaling", The EMBO Journal, vol. 21, No. 18, pp. 4796-4808, 2002.

Yigzaw, Y. et al., "The C Terminus of Sprouty is Important for Modulation of Cellular Migration and Proliferation", The Journal of Biological Chemistry, vol. 276, No. 25, pp. 22742-22747, Jun. 22, 2001.

* cited by examiner

POLYPEPTIDE SEQUENCE OF HUMAN SPROUTY-2
(GENBANK ACCESSION NO. NP_005833 (SEQ ID NO. 3))

```
  1 MEARAQSGNG SQPLLQTPRD GGRQRGEPDP RDALTQQVHV LSLDQIRAIR NTNEYTEGPT
 61 VVPRPGLKPA PRPSTQHKHE RLHGLPEHRQ PPRLQHSQVH SSARAPLSRS ISTVSSGSRS
121 STRTSTSSSS SEQRLLGSSF SSGPVADGII RVQPKSELKP GELKPLSKED LGLHAYRCED
181 CGKCKCKECT YPRPLPSDWI CDKQCLCSAQ NVIDYGTCVC CVKGLFYHCS NDDEDNCADN
241 PCSCSQSHCC TRWSAMGVMS LFLPCLWCYL PAKGCLKLCQ GCYDRVNRPG CRCKNSNTVC
301 CKVPTVPPRN FEKPT
```

| FIG. 7B-1 |
| FIG. 7B-2 |
| FIG. 7B-3 |

FIG. 7B-1

**DNA SEQUENCE OF HUMAN SPROUTY-2
(GENBANK ACCESSION NO. AF039843 (SEQ ID NO. 4))**

```
  1 GGCACGAGGG TAAGGCCGTT TTCTTTTCCC ATTCGCTCAT CTGCCAGGAA AAGGGACTTG
 61 CCGTTGGCGC TTCGGCCTCT TGTTCATTGA GAAAAAAGAG GAAATACTCC GCGTGCGCTT
121 GTAGAAGGGG AGTCGTCTCC AGCTCCGAAC CCCGGAGTGT TCATCAGCGG GGAATCTGGC
181 TCCGAATTCT CTTTTTTTCT CCCGCCGATT GCTCGGAAGT TGGTCTAAAG CAGAGGTTGG
241 AAAGAAAGGA AAAAAGTTTG CATCGAGACT GGATTTATTT GCACATCGCA GAAAGAAGAG
301 AATCCAAGGG AGAGGGGTTG GTGCAAAGCC GCGATCACGG AGTTCAGATG TGTTCTAAGC
361 CTGCTGGAGT GACCACACTT CCAAGACCTG ATGGAGGCCA GAGCTCAGAG TGGCAACGGG
421 TCGCAGCCCT TGCTGCAGAC GCCCCGTGAC GGTGGCAGAC AGCGTGGGGA GCCCGACCCC
481 AGAGACGCCC TCACCCAGCA GGTACATGTC TTGTCTCTGG ATCAGATCAG AGCCATCCGA
541 AACACCAATG AGTACACAGA GGGGCCTACT GTCGTCCCAA GACCTGGGCT CAAGCCTGCT
```

```
 601  CCTCGCCCCT  CCACTCAGCA  CAAACACGAG  AGACTCCACG  GTCTGCCTGA  GCACCGCCAG
 661  CCTCCTAGGC  TCCAGCACTC  GCAGGTCCAT  TCTTCTGCAC  GAGCCCCTCT  GTCCAGATCC
 721  ATAAGCACGG  TCAGCTCAGG  GTCGCGGAGC  AGTACGAGGA  CAAGTACCAG  CAGCAGCTCC
 781  TCTGAACAGA  GACTGCTAGG  ATCATCCTTC  TCCTCCGGGC  CTGTTGCTGA  TGGCATAATC
 841  CGGGTGCAAC  CCAAATCTGA  GCTCAAGCCA  GGTGAGCTTA  AGCCACTGAG  CAAGGAAGAT
 901  TTGGGCCTGC  ACGCCTACAG  GTGTGAGGAC  TGTGGCAAGT  GCAAATGTAA  GGAGTGCACC
 961  TACCCAAGGC  CTCTGCCATC  AGACTGGATC  TGCCGACAAGC  AGTGCCTTTG  CTCGGCCCAG
1021  AACGTGATTG  ACTATGGGAC  TTGTGTATGC  TGTGTGAAAG  GTCTCTTCTA  TCACTGTTCT
1081  AATGATGATG  AGGACAACTG  TGCTGACAAC  CCATGTTCTT  GCAGCCAGTC  TCACTGTTGT
1141  ACACGATGGT  CAGCCATGGG  TGTCATGTCC  CTCTTTTTGC  CTTGTTTATG  GTGTTACCTT
1201  CCAGCCAAGG  GTTGCCTTAA  ATTGTGCCAG  GGGTGTTATG  ACCGGGTTAA  CAGGCCTGGT
1261  TGCCGCTGTA  AAAACTCAAA  CACAGTTTGC  TGCAAAGTTC  CCACTGTCCC  CCCTAGGAAC
1321  TTTGAAAAAC  CAACATAGCA  TCATTAATCA  GGAATATTAC  AGTAATGAGG  ATTTTTCTT
```

FIG. 7B-2

```
1381  TCTTTTTTTA ATACACATAT GCAACCAACT AAACAGTTAT AATCTTGGCA CTGTTAATCG
1441  AAAGTTGGGA TAGTCTTTGC TGTTTGCGGT GAAATGCTTT TTGTCCATGT GCCGTTTAA
1501  CTGATATGCT TGTTAGAACT CAGCTAAATGG AGCTCAAAGT ATGAGATACA GAACTTGGTG
1561  ACCCATGTAT TGCATAAGCT AAAGCAACAC AGACACTCCT AGGCAAAGTT TTTGTTTGTG
1621  AATAGTACTT GCAAAAACTTG TAAATTAGCA GATGACTTTT TTCCATTGTT TTCTCCAGAG
1681  AGAATGTGCT ATATTTTTGT ATATACAATA ATATTTGCAA CTGTGAAAAA CAAGTGTGC
1741  CATACTACAT GGCACAGACA CAAAATATTA TACTAATATG TTGTACATTC GGAAGAATGT
1801  GAATCAATCA GTATGTTTTT AGATTGTATT TTGCCTTACA GAAAGCCTTT ATTGTAAGAC
1861  TCTGATTTCC CTTTGGACTT CATGTATATT GTACAGTTAC AGTAAAATTC AACCTTTATT
1921  TTCTAATTTT TTCAACATAT TGTTTAGTGT AAAGAATATT TATTTGAAGT TTTATTATTT
1981  TATAAAAAAG AATATTTATT TTAAGAGGCA TCTTACAAAT TTTGCCCCTT TTATGAGGAT
2041  GTGATAGTTG CTGCAAATGA GGGGTTACAG ATGCATATGT CCAATATAAA ATAGAAAATA
2101  TATTAACGTT TGAAATTAAA AAAAAAAAAA AAAAA
```

FIG. 7B-3

| Overhang | siRNA | LOOP |
|---|---|---|

```
5'GAGACUGCUAGGAUCAUCCU  UCA
                            A
 UUUUU CUCUGACGAUCCUAGUAGGA GAG

5'GCCACUGAGCAAGGAAGAUU  UCA
                            A
 UUUUU CGGUGACUCGUUCCUUCUAA GAG
```

FIG. 7C

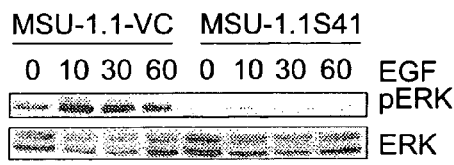
FIG. 9A
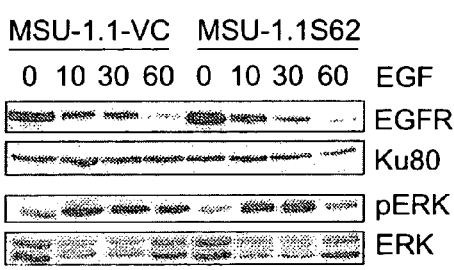
FIG. 9B
FIG. 9C
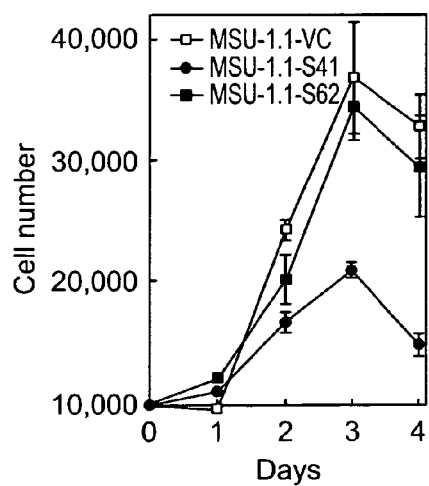
FIG. 9D
FIG. 9E

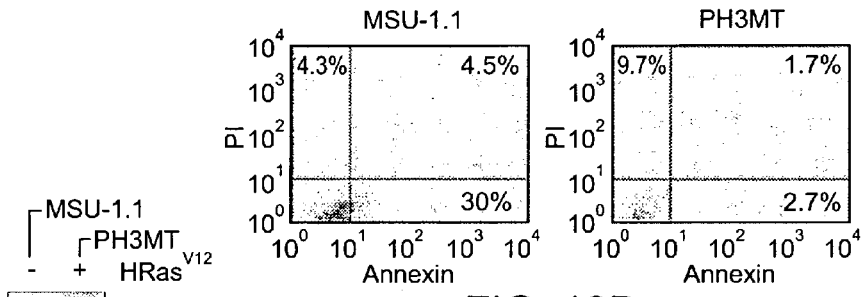
FIG. 10A
FIG. 10B
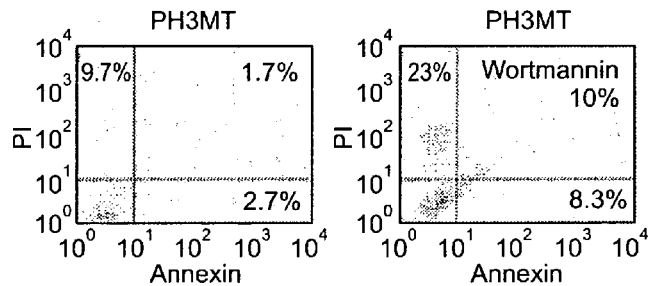
FIG. 10C
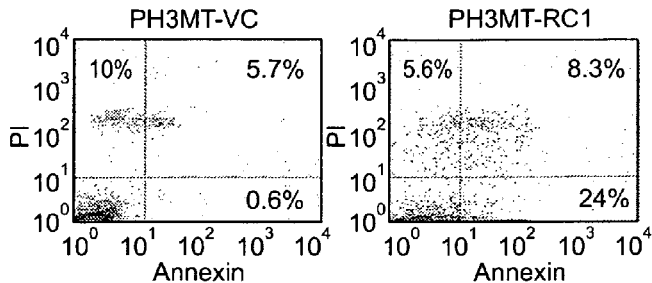
FIG. 10D
FIG. 10E

PH3MT

| + | − | *Scrambled* shRNA |
|---|---|---|
| − | + | *Spry2*- shRNA |

Spry2

Spry1

Ku80

SC 2A3

PH3MT

SC 2A3 pp85 p85 pAkt

Akt

MSU-1.1

| + | − | Vector |
|---|---|---|
| − | + | Spry2-V5 |

Spry2

Ku80

VC S62

FIG. 14A
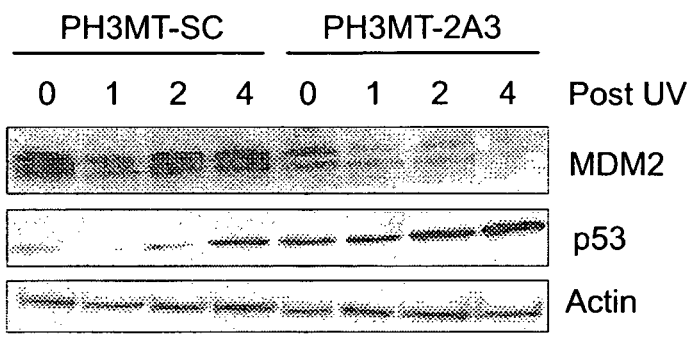
FIG. 14B
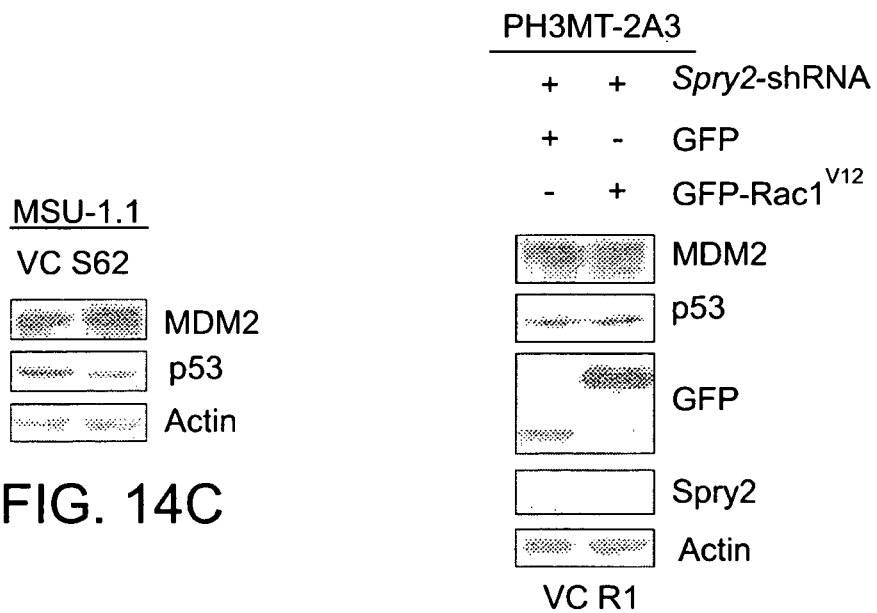
FIG. 14C
FIG. 14D

SEQUENCE LISTING

<160> NUMBER OF SEQ ID NOS: 8

<210> SEQ ID NO 1
<211> LENGTH: 64
<212> TYPE: DNA
<213> ORGANISM: Artificial Sequence

```
<220> FEATURE:
<223> OTHER INFORMATION: Description of Artificial Sequence: Synthetic
      oligonucleotide

<400> SEQUENCE: 1
gatccccgag actgctagga tcatccttca agagaggagt gatcctagca gctcttttg      60 gaaa                                                                   64

<210> SEQ ID NO 2
<211> LENGTH: 64
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
gatccccgcc actgagcaag gaagatttca agagaatctt ccttgctcag tggcttttg      60 gaaa                                                                   64

<210> SEQ ID NO 3
<211> LENGTH: 315
<212> TYPE: PRT
<213> ORGANISM: Homo sapiens

<400> SEQUENCE: 3
```

Met Glu Ala Arg Ala Gln Ser Gly Asn Gly Ser Gln Pro Leu Leu Gln
 1               5                  10                  15

Thr Pro Arg Asp Gly Gly Arg Gln Arg Gly Glu Pro Asp Pro Arg Asp
                20                  25                  30

Ala Leu Thr Gln Gln Val His Val Leu Ser Leu Asp Gln Ile Arg Ala
            35                  40                  45

Ile Arg Asn Thr Asn Glu Tyr Thr Glu Gly Pro Thr Val Val Pro Arg
        50                  55                  60

Pro Gly Leu Lys Pro Ala Pro Arg Pro Ser Thr Gln His Lys His Glu
 65                  70                  75                  80

Arg Leu His Gly Leu Pro Glu His Arg Gln Pro Pro Arg Leu Gln His
                85                  90                  95

Ser Gln Val His Ser Ala Arg Ala Pro Leu Ser Arg Ser Ile Ser
                100                 105                 110

Thr Val Ser Ser Gly Ser Arg Ser Thr Arg Thr Ser Thr Ser Ser
            115                 120                 125

Ser Ser Ser Glu Gln Arg Leu Leu Gly Ser Ser Phe Ser Gly Pro
        130                 135                 140

Val Ala Asp Gly Ile Ile Arg Val Gln Pro Lys Ser Glu Leu Lys Pro
145                 150                 155                 160

Gly Glu Leu Lys Pro Leu Ser Lys Glu Asp Leu Gly Leu His Ala Tyr
                165                 170                 175

Arg Cys Glu Asp Cys Gly Lys Cys Lys Cys Lys Glu Cys Thr Tyr Pro
            180                 185                 190

Arg Pro Leu Pro Ser Asp Trp Ile Cys Asp Lys Gln Cys Leu Cys Ser
        195                 200                 205

Ala Gln Asn Val Ile Asp Tyr Gly Thr Cys Val Cys Val Lys Gly
        210                 215                 220

Leu Phe Tyr His Cys Ser Asn Asp Asp Glu Asp Asn Cys Ala Asp Asn
225                 230                 235                 240

Pro Cys Ser Cys Ser Gln Ser His Cys Cys Thr Arg Trp Ser Ala Met 245                 250                 255
Gly Val Met Ser Leu Phe Leu Pro Cys Leu Trp Cys Tyr Leu Pro Ala
                260                 265                 270
Lys Gly Cys Leu Lys Leu Cys Gln Gly Cys Tyr Asp Arg Val Asn Arg
            275                 280                 285
Pro Gly Cys Arg Cys Lys Asn Ser Asn Thr Val Cys Cys Lys Val Pro
        290                 295                 300
Thr Val Pro Pro Arg Asn Phe Glu Lys Pro Thr
305                 310                 315

<210> SEQ ID NO 4
<211> LENGTH: 2135
<212> TYPE: DNA
<213> ORGANISM: Homo sapiens

<400> SEQUENCE: 4

```
ggcacgaggg taaggccgtt ttcttttccc attcgctcat ctgccaggaa aagggacttg    60
ccgttggcgc ttcggcctct tgttcattga aaaaaagag gaaatactcc gcgtgcgctt   120
gtagaagggg agtcgtctcc agctccgaac cccggagtgt tcatcagcgg ggaatctggc   180
tccgaattct ctttttttct cccgccgatt gctcggaagt tggtctaaag cagaggttgg   240
aaagaaagga aaaagtttg catcgagact ggatttattt gcacatcgca gaaagaagag   300
aatccaaggg agaggggttg gtgcaaagcc gcgatcacgg agttcagatg tgttctaagc   360
ctgctggagt gaccacactt ccaagacctg atggaggcca gagctcagag tggcaacggg   420
tcgcagccct tgctgcagac gccccgtgac ggtggcagac agcgtgggga gcccgacccc   480
agagacgccc tcacccagca ggtacatgtc ttgtctctgg atcagatcag agccatccga   540
aacaccaatg agtacacaga ggggcctact gtcgtcccaa gacctgggct caagcctgct   600
cctcgcccct ccactcagca caacacgag agactccacg gtctgcctga gcaccgccag   660
cctcctaggc tccagcactc gcaggtccat tcttctgcac gagcccctct gtccagatcc   720
ataagcacgg tcagctcagg gtcgcggagc agtacgagga caagtaccag cagcagctcc   780
tctgaacaga gactgctagg atcatccttc tcctccgggc ctgttgctga tggcataatc   840
cgggtgcaac ccaaatctga gctcaagcca ggtgagctta gccactgag caaggaagat   900
ttgggcctgc acgcctacag tgtgaggac tgtggcaagt gcaaatgtaa ggagtgcacc   960
tacccaaggc ctctgccatc agactggatc tgcgacaagc agtgcctttg ctcggcccag  1020
aacgtgattg actatgggac ttgtgtatgc tgtgtgaaag gtctcttcta tcactgttct  1080
aatgatgatg aggacaactg tgctgacaac ccatgttctt gcagccagtc tcactgttgt  1140
acacgatggt cagccatggg tgtcatgtcc ctcttttttgc cttgtttatg gtgttacctt  1200
ccagccaagg gttgccttaa attgtgccag gggtgttatg accgggttaa caggcctggt  1260
tgccgctgta aaaactcaaa cacagtttgc tgcaaagttc ccactgtccc cctaggaac   1320
tttgaaaaac caacatagca tcattaatca ggaatattac agtaatgagg attttttctt  1380
tcttttttta atacacatat gcaaccaact aaacagttat aatcttggca ctgttaatcg  1440
aaagttggga tagtctttgc tgtttgcggt gaaatgcttt tgtccatgt gccgttttaa   1500
ctgatatgct tgttagaact cagctaatgg agctcaaagt atgagataca gaacttggtg  1560
acccatgtat tgcataagct aaagcaacac agacactcct aggcaaagtt tttgtttgtg  1620
aatagtactt gcaaaacttg taaattagca gatgactttt ttccattgtt ttctccagag  1680
agaatgtgct atattttgt atatacaata atatttgcaa ctgtgaaaaa caagttgtgc   1740
```

-continued

```
catactacat ggcacagaca caaaatatta tactaatatg ttgtacattc ggaagaatgt      1800
gaatcaatca gtatgttttt agattgtatt ttgccttaca gaaagccttt attgtaagac      1860
tctgatttcc ctttggactt catgtatatt gtacagttac agtaaaattc aacctttatt      1920 ttctaattt ttcaacatat tgtttagtgt aaagaatatt tatttgaagt tttattattt      1980
tataaaaaag aatatttatt ttaagaggca tcttacaaat tttgcccctt ttatgaggat      2040
gtgatagttg ctgcaaatga ggggttacag atgcatatgt ccaatataaa atagaaaata    2100
tattaacgtt tgaaattaaa aaaaaaaaaa aaaaa                                2135
```

```
<210> SEQ ID NO 5
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 5
gagacugcua ggaucauccu                                                    20

<210> SEQ ID NO 6
<211> LENGTH: 20
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 6
gccacugagc aaggaagauu                                                    20

<210> SEQ ID NO 7
<211> LENGTH: 52
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 7
gagacugcua ggaucauccu ucaagagagg augauccuag cagucucuuu uu               52

<210> SEQ ID NO 8
<211> LENGTH: 52
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 8
gccacugagc aaggaagauu ucaagagaau cuuccuugcu caguggcuuu uu               52
```

TUMOR INHIBITION BY MODULATING SPROUTY EXPRESSION OR ACTIVITY

RELATED APPLICATIONS

This application claims the benefit of U.S. Provisional Application No. 60/671,783, filed on Apr. 16, 2005, the contents of which are incorporated herein in their entirety.

GOVERNMENT SUPPORT

The U.S. Government may have certain rights in this invention pursuant to Grant No. CA098305, awarded by the National Institutes of Health.

TECHNICAL FIELD

This application relates to the medical arts. In particular, the invention relates to compositions and methods for diagnosis and treating cancer.

BACKGROUND

Sprouty (Spry) is a family of intracellular proteins that are endogenous regulators of receptor tyrosine kinase pathways such as the Ras/MAP kinase pathway. Sprouty was first identified in *Drosophila* as an inhibitor of fibroblast growth factor (FGF)-induced tracheal branching (Hacohen et al. (1998) *Cell* 92:253-263) and epidermal growth factor (EGF)-induced eye development (Casci et al. (1999) *Cell* 96:655-665). Mammalian species express four isoforms of Sprouty (Spry1-4) (Hacohen et al. (1998) *Cell* 92:253-263; de Maximy et al. (1999) *Mech. Dev.* 81:213-216; Minowada et al. (1999) *Develop.* 126:4465-4475), which act as inhibitors of growth factor-induced cellular differentiation, migration, and proliferation (Gross et al. (2001) *J. Biol. Chem.* 276:46460-46468; Impagnatiello et al. (2001) *J. Cell Biol.* 152(5):187-1098; Yigzaw et al. (2001) *J. Biol. Chem.* 276:22742-22747; Hanafusa et al. (2002) *Nat. Cell Biol.* 4:850-858). Although this antagonistic function is mediated by the ability of Sprouty proteins to regulate the RTK-RAS/mitogen-activated protein kinase (MAPK) pathway, the protein(s) on which they exert their action appears to be highly signal-specific (Gross et al. (2001) *J. Biol. Chem.* 276:46460-46468; Hanafusa et al. (2002) *Nat. Cell Biol.* 4:850-858; Sasaki et al. (2003) *Nat. Cell Biol.* 2:281-282).

At least four Sprouty proteins have been identified in humans. The specific role of Sprouty2 in the regulation of RTK signaling in human cells appears more complicated than in other mammalian cells. Recent evidence shows that in addition to the antagonistic function, Sprouty2 also acts as an agonist of the RTK pathway, specifically the epidermal growth factor receptor (EGFR) pathway (Egan et al. (2002) *Proc. Natl. Acad. Sci. U.S.A.* 99:6041-6046; Wong et al. (2002) *EMBO J.* 21:4796-4808; Rubin et al. (2003) *Curr. Biol.*, 13:297-307). This agonistic function is the result of the interaction of Sprouty2 with c-Cbl, an E3 ubiquitin ligase that catalyzes the ubiquitination of EGFR, targeting this receptor for proteosomal degradation (Thien et al. (2001) *Nat. Rev. Mol. Cell. Biol.* 2:294-307). By binding to c-Cbl, Sprouty2 prevents the interaction between c-Cbl and EGFR, and this blocks the degradation of the receptor, which leads to sustained EGFR-induced ERK activity (Wong et al. (2001) *J. Biol. Chem.* 276:5866-5875; Egan et al. (2002) *Proc. Natl. Acad. Sci. U.S.A.*, 99:6041-6046; Wong et al. (2002) *EMBO J.* 21:4796-4808; Rubin et al. (2003) *Curr. Biol.* 13:297-307). While the antagonistic function of Sprouty2 regulates several cellular functions, little is know about the cellular functions that are regulated by the agonistic function of Sprouty2.

SUMMARY

Aspects of the present invention are based on the finding that a protein, Sprouty, involved in the regulation of cellular signaling pathways, has a critical role in the formation of tumors that are induced by the oncogene, Ras. It has been determined that down-regulation of Sprouty (e.g., Sprouty2) inhibits the growth of the oncogene-transformed cells and such down-regulated cells are unable to form tumors. Sprouty is expressed in a number of cancer cells, and targeting its functions can be used to inhibit tumor growth and/or tumor formation.

These findings have been exploited to produce the present invention, which, in one aspect, includes Spry 2 antagonist compositions that decreases Spry2 expression or activity. In some embodiments, the Spry2 antagonist is an siRNA. In particular embodiments, the siRNA is expressed from an siRNA-expression vector that includes the Spry2-targetting fragments 5'GATCCCCGAG ACTGCTAGGA TCATCCT-TCA AGAGAGGAGT GATCCTAGCA GCTCTTTTTG GAAA (SEQ ID NO:1) or 5'GATCCCCGCC ACTGAG-CAAG GAAGATFTCA AGAGAATCTT CCTTGCTCAG TGGCTTTTTG GAAA (SEQ ID NO:2). In other embodiments, the siRNA antagonist is a Spry2 siRNA having a Spry2 sequence such as GAGACUGCUA GGAUCAUCCU (SEQ ID NO: 5) or GCCACUGAGC AAGGAAGAUU (SEQ ID NO: 6). In yet other embodiments, the siRNA antagonist is one of the two Spry2 siRNAs shown in FIG. 7C. In still other embodiments, the Spry2 antagonist is a Spry2-targeted ribozyme, a Spry2-targeted antisense oligonucleotide, or a Spry2-targeted siRNA. In further embodiments, the Spry2 antagonist is an aptamer, a protein, a peptide, a cyclic peptide, a peptidomimetic or a small molecule. In particularly useful embodiments, the Spry2 antagonist is a polypeptide fragment or mutant form of a Spry2 protein, which may function as a competitive inhibitor of a Spry2-interacting polypeptide (e.g., the c-Cbl E3 ubiquitin ligase, EGFR, Ras, or CIN85). In certain embodiments, the Spry2 protein has the polypeptide sequence of SEQ ID NO:3, shown in FIG. 7A.

In another aspect, the invention provides pharmaceutical formulations of a Spry2 antagonist that decreases Spry2 expression or activity and a pharmaceutical carrier. In some embodiments, the Spry2 antagonist included in the pharmaceutical formulation is an siRNA. In particular embodiments, the siRNA is expressed from an siRNA-expression vector that includes the Spry2-targetting fragments 5'GATCCCCGAG ACTGCTAGGA TCATCCTTCA AGAGAGGAGT GATC-CTAGCA GCTCTTTTTG GAAA (SEQ ID NO:1) or 5'GATCCCCGCC ACTGAGCAAG GAAGATTTCA AGAGAATCTT CCTTGCTCAG TGGCTTTTTG GAAA (SEQ ID NO:2). In other embodiments, the siRNA antagonist is a Spry2 siRNA having a Spry2 sequence such as GAGACUGCUA GGAUCAUCCU (SEQ ID NO: 5) or GCCACUGAGC AAGGAAGAUU (SEQ ID NO: 6). In yet other embodiments, the Spry2 siRNA pharmaceutical formulation includes one of the two Spry2 siRNAs shown in FIG. 7C. In still other embodiments, the Spry2 antagonist included in the pharmaceutical formulation is a Spry2-targeted ribozyme, a Spry2-targeted antisense oligonucleotide, or a Spry2-targeted siRNA. In further embodiments, the Spry2 antagonist in the pharmaceutical formulation is an aptamer, a protein, a peptide, a cyclic peptide, a peptidomimetic or a small molecule. In particularly useful embodiments, the Spry2 antagonist in the pharmaceutical formulation is a polypeptide fragment or mutant form of a Spry2 protein, which may function as a competitive inhibitor of a Spry2-interacting polypeptide (e.g., the c-Cbl E3 ubiquitin ligase, EGFR, Ras, or CIN85). In certain embodiments, the Spry2 protein has the polypeptide sequence of SEQ ID NO:3, shown in FIG. 7A.

In a further aspect, the invention provides methods of treating a cancer in a subject by administering a pharmaceutically effective amount of a Spry2 antagonist that decreases Spry2 expression or activity. In particular embodiments, the cancer treated is a malignancy characterized by an elevated level of Ras (e.g., Ras expression and/or activity). In some embodiments, the cancer treated is a fibrosarcoma, or a melanoma. In other embodiments, the cancer treated is a pancreatic cancer. In still other embodiments, the cancer treated is a lung cancer, e.g., a lung cancer that is characterized by malignant cell growth having an elevated level of activated EGFR, an elevated level of EGFR or an elevated level of phosphorylated EGFR compared to a normal lung cell. In some embodiments, the Spry2 antagonist administered is an siRNA. In particular embodiments, the siRNA administered is expressed from an siRNA-expression vector that includes the Spry2-targetting fragments GATCCCCGAG ACTGCTAGGA TCATCCTTCA AGAGAGGAGT GATCCTAGCA GCTCTTTTTG GAAA (SEQ ID NO:1) or GATCCCCGCC ACTGAGCAAG GAAGATTTCA AGAGAATCTT CCTTGCTCAG TGGCTTTTTG GAAA (SEQ ID NO:2). In yet other embodiments, the siRNA antagonist administered is a Spry2 siRNA having a Spry2 sequence such as GAGACUGCUA GGAUCAUCCU (SEQ ID NO: 5) or GCCACUGAGC AAGGAAGAUU (SEQ ID NO: 6). In other embodiments, the siRNA antagonist administered is one of the two Spry2 siRNAs shown in FIG. 7C. In still other embodiments, the Spry2 antagonist administered is a Spry2-targeted ribozyme, a Spry2-targeted antisense oligonucleotide, or a Spry2-targeted siRNA. In further embodiments, the Spry2 antagonist administered is an aptamer, a protein, a peptide, a cyclic peptide, a peptidomimetic or a small molecule. In particularly useful embodiments, the Spry2 antagonist administered is a polypeptide fragment or mutant form of a Spry2 protein, which may function as a competitive inhibitor of a Spry2-interacting polypeptide (e.g., the c-Cbl E3 ubiquitin ligase, EGFR, Ras, or CIN85). In certain useful embodiments, the method of the invention further includes administering a pharmaceutically-effective amount of an agent that induces apoptosis of malignant cells in combination with the Spry2 antagonist. In particularly useful embodiments, the method includes the step of administering a pharmaceutically-effective amount of an EGFR-targeted chemotherapeutic drug in combination with the Spry2 antagonist. In particular embodiments, the EGFR-targeted chemotherapeutic drug is certuximab, erlotinib, gefitinib or matuzumab.

In still another aspect, the invention provides methods of inhibiting the tumor forming potential of a cancer cell by contacting the cell (e.g., in vitro) with an effective amount of a Spry2 antagonist that decreases Spry2 expression or activity. In particularly useful embodiments, the cancer cell is one characterized by an elevated level of Ras (e.g., Ras expression and/or activity). In particular embodiments, the cancer cell contacted is a fibrosarcoma, or a melanoma. In other embodiments, the cancer cell is a pancreatic cancer cell. In still other embodiments, the cancer cell is a lung cancer cell, e.g., a lung cancer cell that is characterized an elevated level of activated EGFR, an elevated level of EGFR or an elevated level of phosphorylated EGFR compared to a normal lung cell. In some embodiments, the Spry2 antagonist that the cancer cell is contacted with is an siRNA. In particular embodiments, the siRNA is expressed from an siRNA-expression vector that includes the Spry2-targetting fragments GATCCCCGAG ACTGCTAGGA TCATCCTTCA AGAGAGGAGT GATCCTAGCA GCTCTTTTTG GAAA (SEQ ID NO:1) or GATCCCCGCC ACTGAGCAAG GAAGATTTCA AGAGAATCTT CCTTGCTCAG TGGCTTTTTG GAAA (SEQ ID NO:2). In other embodiments, the siRNA antagonist that the cell is contacted with is a Spry2 siRNA having a Spry2 sequence such as GAGACUGCUA GGAUCAUCCU (SEQ ID NO: 5) or GCCACUGAGC AAGGAAGAWU (SEQ ID NO: 6). In particular embodiments, the siRNA antagonist that the cancer cell is contacted with is one of the two Spry2 siRNAs shown in FIG. 7C. In still other embodiments, the Spry2 antagonist that the cancer cell is contacted with is a Spry2-targeted ribozyme, a Spry2-targeted antisense oligonucleotide, or a Spry2-targeted siRNA. In further embodiments, the Spry2 antagonist is an aptamer, a protein, a peptide, a cyclic peptide, a peptidomimetic or a small molecule. In particular embodiments, the Spry2 antagonist that the cancer cell is contacted with is a polypeptide fragment or mutant form of a Spry2 protein, which may function as a competitive inhibitor of a Spry2-interacting polypeptide (e.g., the c-Cbl E3 ubiquitin ligase, EGFR, Ras, or CIN85). In another embodiment, the method of the invention further includes the step of treating the cancer cell with UV light. In certain embodiments, the method of the invention further includes the step of treating the cancer cell with an effective amount of an agent that induces apoptosis. In some embodiments, the method further includes the step of contacting the cancer cell with an EGFR-targeted chemotherapeutic drug (sequentially, or in combination with the Spry2 antagonist). In certain embodiments, the EGFR-targeted chemotherapeutic drug that the cancer cell is contacted with is certuximab, erlotinib, gefitinib or matuzumab.

In yet another aspect, the invention provides methods identifying a compound that reduces the tumorigenicity of a malignant cell. In general, method includes the steps of contacting a Ras-transformed or Spry2-overexpressing malignant cell with a test compound, so as to provide a "test sample", and then comparing the level of Spry2 expression or activity in the test sample to the level of Spry2 expression or activity in a control Ras-transformed or Spry2-overexpressing malignant cell that has not been contacted with the test compound. A decrease in the expression or activity of Spry in the test sample compared to the control indicates that the test compound will reduce the tumorigenicity of a malignant cell. In certain embodiments, the method includes step of assaying the test sample for its ability to form colonies in soft agar. In further embodiments, the method includes the step of measuring the expression or activity of epidermal growth factor receptor (EGFR) in the test sample. In particular embodiments, the malignant cell is derived from a human. In further embodiments, the malignant cell is a Ras-transformed cell. In other embodiments, the malignant cell is derived from a fibrosarcoma, melanoma, or a pancreatic cancer cell. In certain embodiments, the test compound is a nucleic acid molecule. In other embodiments, the test compound is an siRNA. In still other embodiments, the test compound is an aptamer, a peptide, a peptidomimetic, a small non-nucleic acid organic molecule, or a small organic or inorganic molecule.

In still another aspect, the invention provides methods of diagnosing or detecting a Ras-related cancer in a subject by obtaining a cellular specimen from the subject; detecting the level of expression or activity of Spry2 in the subject's cellular specimen; and comparing the level of expression or activity of Spry2 in the subject's cellular specimen to the level of Spry2 in a control, non-cancerous cellular specimen from the same or a similar tissue as that of the subject's cellular specimen. In general, the subject has, or is at risk for having, a Ras-related cancer if the level of expression or activity of Spry2 in the subject's cellular specimen is higher than the level of expression or activity of Spry2 in the control cellular specimen. In particular embodiments, the Ras-related cancer diagnosed or detected is a fibrosarcoma, a melanoma, or a pancreatic cancer. In further embodiments, the Ras-related cancer is a pancreatic cancer. In still further embodiments, the Ras-related cancer is a lung cancer, e.g., a lung cancer that is characterized by an activated EGFR, an elevated level of EGFR or an elevated level of phosphorylated EGFR compared to a normal lung cell.

DESCRIPTION OF THE DRAWINGS

FIG. 7A is a is a schematic representation of the polypeptide sequence of a human Sprouty-2 (GenBank Accession No. NP_0055833 (SEQ ID NO: 3).

FIG. 7B is a schematic representation of the nucleotide sequence of a human Sprouty-2 nucleic acid (GenBank Accession No. AF039843 (SEQ ID NO: 4)). The initiation and termination codons of the profilin protein open reading frame (ORF) are underlined and the sequences targeted by the anti-Sprouty2 siRNAs shown in FIG. 7C are highlighted in bold.

FIG. 7C is a schematic representation of two anti-Sprouty2 siRNAs, showing the folded structure of each of the expressed RNAs (SEQ ID NOS 7 & 8 disclosed respectively in order of appearance).

FIG. 9A is a photographic representation of a Western blot depicting the results of experiments in which MSU-1.1 cells were stably transfected with an empty vector (MSU-1.1-VC), or a vector encoding V5-tagged Spry2 (MSU-1.1S41 and S62) and whole cell lysates from the indicated cell strains were analyzed for Spry2 expression using Western blotting.

FIG. 9B is a photographic representation of a Western blot depicting the results of experiments in which whole cell lysates were prepared from MSU-1.1-VC or MSU-1.1S41 cells that were treated with EGF and then assayed using Western blotting for ERK activation.

FIG. 9C is a photographic representation of a Western blot depicting the results of experiments in which whole cell lysates were prepared from MSU-1.1-VC or MSU-1.1S41 cells that were treated with EGF and then assayed for EGFR, Ku80, pERK, or ERK as indicated using Western blotting.

FIG. 9D is a photographic representation of a Western blot depicting the results of experiments in which whole cell lysates from the indicated cell lines were pulled down with RafRBD conjugated beads and the total amount of Ras in the whole cell lysate was determined using a Pan-Ras-specific antibody.

FIG. 9E is a graph representation depicting the results of experiments in which MSU-1.1-VC, MSU-1.1-S41, or MSU-1.1-S62 cell strains were grown in medium containing 0.1% serum, and the number of cells determined during the culture period. One of two experimental repeats (N=4) is shown.

FIG. 10A is a photographic representation of the results of experiments in which the levels of Spry2 and HRas expression were assayed by Western blot in immortalized human fibroblasts (MSU-1.1) and the HRas oncogene-transformed derivatives (PH3MT).

FIG. 10B is a representation of a flow cytometry plot of the results of experiments in which indicated cell lines were treated with UV, stained with Annexin V, and analyzed using flow cytometry. Live cells are represented in the lower left quadrant. Early apoptotic cells are represented in the lower right quadrant. Late apoptotic and necrotic cells are represented in the upper right quadrant. Dead cells are represented in the upper left quadrant.

FIG. 10C is a representation of a flow cytometry plot of the results of experiments in which HRas-transformed cells (PH3MT) were treated as in 10B in the presence or absence of Wortmannin (50 nM).

FIG. 10D is a photographic representation of Western blots from experiments in which whole cell lysates from HRas-transformed fibroblasts (PH3MT) were stably transfected with an empty vector or a vector encoding a Myc-tagged, dominant negative form of Rac1 (Rac1$^{N17}$) and expression of dominant negative Rac1 analyzed.

FIG. 10E (left panel) is a representation of a flow cytometry plot of the results of experiments in which PH3MT cells expressing an empty vector (PH3MT-VC) were analyzed as in FIG. 10B.

FIG. 10E (right panel) is a representation of a flow cytometry plot of the results of experiments in which PH3MT cells expressing Rac1$^{N17}$ (PH3MT-RC1) were analyzed as in FIG. 10B.

FIG. 14A is a photographic representation of a Western blot depicting the results of an experiment in which control HRas-transformed cells (PH3MT-SC) and HRas-transformed cells with down-regulated Spry2 (PH3MT-2A3) were analyzed using the indicated antibodies.

FIG. 14B is a photographic representation of a Western blot depicting the results of an experiment in which the same cell strains as for FIG. 14B were treated with UV, cultured under normal conditions for the indicated time periods following UV treatment, then prepared and analyzed.

FIG. 14C is a photographic representation of a Western blot depicting the results of an experiment in which immortalized fibroblasts expressing either an empty vector (MSU-1.1-VC) or Spry2-V5 (MSU-1.1-S62) were analyzed to for MDM2 and p53.

FIG. 14D is a photographic representation of a Western blot depicting the results of an experiment in which whole cell lysates from HRas-transformed cells with down-regulated Spry2 (PH3MT-2A3) were stably transfected with a vector encoding GFP-Rac1$^{V12}$ (2A3-R1) or with a vector encoding GFP alone (2A3-VC) were analyzed by Western blotting with the indicated antibodies.

DETAILED DESCRIPTION

Figure 1A:
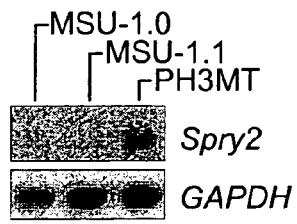
FIG. 1A is a photographic representation of a Northern blot depicting the expression of Sprouty2 in Ras-transformed cells and in immortalized human fibroblasts, MSU-1.0, MSU-1.1, and in MSU-1.1 cells malignantly transformed by the H-Ras oncogene (PH3MT).

All publications, patent applications, patents, and other references mentioned herein are incorporated by reference in their entirety. In addition, the materials, methods, and examples are illustrative only and not intended to be limiting. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below.

The invention is based on discoveries related to the function of Sprouty2 in the H-Ras oncogene-transformed human fibroblast cell line PH3MT. It has been determined that this cell line expresses a substantially higher level of Sprouty2 protein than is found in a direct precursor of the cell line, i.e., the non-tumorigenic MSU-1.1 cell strain. When the expression of Sprouty2 was stably down-regulated in PH3MT cells, not only were there decreased levels of EGFR and activated ERK, but also a complete loss of tumor-forming ability by the H-Ras-transformed cells was observed. These results demonstrate that Sprouty2 contributes to the malignant transformation of human fibroblasts by the H-Ras oncogene.

Assays for Compounds that Inhibit Sprouty Expression or Activity

In one aspect, the invention provides, a cell-based assay that is useful for identifying a compound that inhibits Sprouty expression or activity. In this assay, a cell that expresses a Sprouty protein, or biologically active portion thereof, is contacted with a test compound, and the ability of the test compound to decrease Sprouty activity is determined. Such assays can be combined with other assays or used as a secondary assay to test compounds that, e.g., bind to a Sprouty protein, decrease the amount of Sprouty protein in a cell, or decrease the amount of Sprouty RNA in a cell.

Determining the ability of the test compound to decrease Sprouty activity can be accomplished by monitoring, for example, EGFR protein levels, EGFR activity, or ERK activity. In general, a compound that decreases Sprouty by decreasing Sprouty expression or activity in a Ras-transformed cell will decrease EGFR protein levels or activity and decrease ERK activity. Methods of monitoring such activities are known in the art, e.g., Egan et al. (2002) *Proc. Natl. Acad. Sci. U.S.A.*, 99:6041-6046 Wong et al. (2001) *J. Biol. Chem.*, 276:5866-5875; and Wong et al. (2002) *EMBO J.* 2: 4796-4808). The cell can be of mammalian origin, e.g., human.

The ability of the test compound to decrease Sprouty binding to a compound, e.g., a Sprouty substrate, or to bind to Sprouty, is also provided by the present invention. Compounds that bind to Sprouty are candidate compounds for modulators of Sprouty expression or activity. Binding assays can be accomplished, for example, by coupling the compound with a radioisotope or enzymatic label such that binding of the compound to Sprouty can be determined by detecting the labeled compound in a complex. Alternatively, Sprouty can be coupled with a radioisotope or enzymatic label to monitor the ability of Sprouty to bind to a test compound.

In another aspect, a Sprouty protein is labeled and bound to a Sprouty substrate (a molecule or fragment thereof to which Sprouty can bind or interact such as a CB1 (e.g., GenBank Accession No. P22682) or a Ras (e.g., GenBank Accession No. P01112 (H-Ras), P0111 (N-Ras), or P01116 (K-Ras)) to form a complex, and the ability of a test compound to decrease Sprouty binding to a Sprouty substrate in the complex is tested. For example, a molecule (e.g., a Sprouty substrate) can be labeled, e.g., with $^{125}$I, $^{35}$S, $^{14}$C, or $^{3}$H, either directly or indirectly, and the radioisotope detected by direct counting of radioemission or by scintillation counting. Alternatively, compounds can be enzymatically labeled with, for example, horseradish peroxidase, alkaline phosphatase, or luciferase, and the enzymatic label detected by determination of conversion of an appropriate substrate to product. Such assays can be conducted as displacement assays (in which a Sprouty protein and substrate are permitted to bind and then a test compound is added and the ability of the test compound to displace binding between the Sprouty protein and substrate determined), or as competition assays (in which a Sprouty protein is incubated with both a Sprouty substrate and a test compound and the ability of the test compound to compete with the substrate for binding to the Sprouty protein is determined), as described herein, and are known in the art.

The ability of a compound (e.g., a Sprouty substrate or a test compound) to interact with Sprouty with or without the labeling of any of the interactants can be evaluated according to methods of the invention. For example, the interaction of a compound with Sprouty can be detected, e.g., using a microphysiometer, without the labeling of either the compound or the Sprouty (McConnell et al. (1992) *Science*, 257:1906-1912). As used herein, a "microphysiometer" (e.g., Cytosensor®) is an analytical instrument that measures the rate at which a cell acidifies its environment using a light-addressable potentiometric sensor (LAPS). Changes in this acidification rate can be used as an indicator of the interaction between a compound and Sprouty.

In general, cell-free assays involve preparing a reaction mixture of the target gene protein and the test compound under conditions and for a time sufficient to allow the two components to interact and bind, thus forming a complex that can be removed and/or detected. A cell-free assay is also provided by the invention, in which a Sprouty protein or biologically active portion thereof is contacted with a test compound and the ability of the test compound to bind to the Sprouty protein or biologically active portion thereof is evaluated. Biologically active portions of the Sprouty proteins to be used in assays of the present invention include fragments that participate in interactions with non-Sprouty molecules, e.g., fragments with high surface probability scores.

Soluble and/or membrane-associated forms of isolated proteins (e.g., Sprouty proteins or biologically active portions thereof) are also useful in the cell-free assays. When membrane-associated forms of the protein are used, it may be desirable to utilize a solubilizing agent. Non-limiting examples of such solubilizing agents include non-ionic detergents such as n-octylglucoside, n-dodecylglucoside, n-dodecylmaltoside, octanoyl-N-methylglucamide, decanoyl-N-methylglucamide, Triton® X-100, Triton® X-114, Thesit®, Isotridecypoly(ethylene glycol ether)$_n$, 3-[(3-cholamidopropyl)dimethylammonio]-1-propane sulfonate (CHAPS), 3-[(3-cholamidopropyl)dimethylammonio]-2-hydroxypropane-1-sulfonate (CHAPSO), or N-dodecyl=N,N-dimethyl-3-ammonio-1-propane sulfonate.

The interaction between two molecules such as a Sprouty protein and a test compound can also be detected, e.g., using fluorescence energy transfer (FET) (see, e.g., U.S. Pat. Nos. 5,631,169 and 4,868,103). A fluorophore label on the first, 'donor' molecule is selected such that its emitted fluorescent energy will be absorbed by a fluorescent label on a second, 'acceptor' molecule, which in turn is able to fluoresce due to the absorbed energy. Alternately, the 'donor' protein molecule can simply utilize the natural fluorescent energy of tryptophan residues. Labels are chosen that emit different wavelengths of light, such that the 'acceptor' molecule label can be differentiated from that of the 'donor'. Since the efficiency of energy transfer between the labels is related to the distance separating the molecules, the spatial relationship between the molecules can be assessed. In a situation in which binding occurs between the molecules, the fluorescent emission of the 'acceptor' molecule label in the assay should be maximal. An FET binding event can be conveniently measured through standard fluorometric detection means well known in the art (e.g., using a fluorimeter).

In another aspect, determining the ability of the Sprouty protein to bind to a target molecule can be accomplished using real-time Biomolecular Interaction Analysis (BIA) (e.g., Sjolander et al. (1991) *Anal. Chem.* 63:2338-2345; and Szabo et al. (1995) *Curr. Opin. Struct. Biol.* 5:699-705). "Surface plasmon resonance" or "BIA" detects biospecific interactions in real time, without labeling any of the interactants (e.g., BIAcore). Changes in the mass at the binding surface (indicative of a binding event) result in alterations of the refractive index of light near the surface (the optical phenomenon of surface plasmon resonance (SPR)), resulting in a detectable signal that can be used as an indication of real-time reactions between biological molecules.

The Sprouty protein or the test substance can be anchored onto a solid phase. The Sprouty protein/test compound complexes anchored on the solid phase can be detected at the end of the reaction. For example, the Sprouty protein is anchored onto a solid surface, and the test compound, (which is not anchored), can be labeled, either directly or indirectly, with detectable labels discussed herein.

In some assays, it is desirable to immobilize either Sprouty, an anti-Sprouty antibody or its target molecule to facilitate separation of complexed from uncomplexed forms of one or both of the proteins, as well as to accommodate automation of the assay. Binding of a test compound to a Sprouty protein, or interaction of a Sprouty protein with a Sprouty binding molecule (such as Cb1) in the presence and absence of a candidate compound, can be accomplished in any vessel suitable for containing the reactants. Nonlimiting examples of such vessels include microtiter plates, test tubes, and micro-centrifuge tubes. In one example, a fusion protein can be provided which adds a domain that allows one or both of the proteins to be bound to a matrix. For example, a glutathione-S-transferase/Sprouty fusion protein or glutathione-S-transferase/target fusion protein can be adsorbed onto glutathione Sepharose® beads (Sigma Chemical, St. Louis, Mo.) or glutathione derivatized microtiter plates, which are then combined with the test compound or the test compound and either the non-adsorbed Sprouty binding protein (e.g., Cb1) or Sprouty protein, and the mixture incubated under conditions conducive to complex formation (e.g., at physiological conditions for salt and pH). Following incubation, the beads or microtiter plate wells are washed to remove any unbound components, the matrix immobilized in the case of beads, complex determined either directly or indirectly, for example, as described above. Alternatively, the complexes can be dissociated from the matrix, and the level of Sprouty binding or activity determined using techniques known in the art.

Other techniques for immobilizing either a Sprouty protein or a molecule that can bind a Sprouty protein on matrices include using conjugation of biotin and streptavidin. Biotinylated Sprouty protein or Sprouty binding molecules can be prepared from biotin-NHS (N-hydroxy-succinimide) using techniques known in the art (e.g., biotinylation kit, Pierce Chemicals, Rockford, Ill.), and immobilized in the wells of streptavidin-coated 96 well plates (Pierce Chemical). To conduct the assay, the non-immobilized component is added to the coated surface containing the anchored component. After the reaction is complete, unreacted components are removed (e.g., by washing) under conditions such that any complexes formed will remain immobilized on the solid surface. The detection of complexes anchored on the solid surface can be accomplished in a number of ways. Where the previously non-immobilized component is pre-labeled, the detection of label immobilized on the surface indicates that complexes were formed. Where the previously non-immobilized component is not pre-labeled, an indirect label can be used to detect complexes anchored on the surface; e.g., using a labeled antibody specific for the immobilized component (the antibody, in turn, can be directly labeled or indirectly labeled with, e.g., a labeled anti-Ig antibody).

An assay, e.g., to identify a compound that can bind to a Sprouty protein, can be performed according to the method of the invention using antibodies reactive with Sprouty protein or target molecules but that do not interfere with binding of the Sprouty protein to a Sprouty binding molecule. Such antibodies can be derivatized to the wells of the plate, and unbound target or Sprouty protein trapped in the wells by antibody conjugation. Methods for detecting such complexes, in addition to those described above for the GST-immobilized complexes, include, but are not limited to, immunodetection of complexes using antibodies reactive with the Sprouty protein or a Sprouty binding molecule, as well as enzyme-linked assays which rely on detecting an enzymatic activity associated with the Sprouty protein or Sprouty binding molecule.

Cell free assays can also be conducted in a liquid phase. In such an assay, the reaction products are separated from unreacted components, by any of a number of standard techniques, including but not limited to, differential centrifugation (see, e.g., Rivas et al. (1993) *Trends Biochem. Sci.* 18:284-287); chromatography (gel filtration chromatography, ion-exchange chromatography); electrophoresis (see, e.g., Ausubel et al. eds. *Current Protocols in Molecular Biology*. New York, N.Y.: J. Wiley, 1999); and immunoprecipitation (see, e.g., Ausubel et al. eds. *Current Protocols in Molecular Biology*. New York, N.Y.: J. Wiley, 1999). Such resins and chromatographic techniques are known to those in the art (see, e.g., Heegaard (1998) *J. Mol. Recognit.* 11:141-148; Hage et al. (1997) *J. Chromatogr. B. Biomed. Sci. Appl.* 699:499-525). Fluorescence energy transfer can also be utilized, as described herein, to detect binding without further purification of the complex from solution.

In some cases, an assay according to the invention includes contacting the Sprouty protein or a biologically active portion thereof with a known compound that binds Sprouty (a Sprouty binding molecule) to form an assay mixture, contacting the assay mixture with a test compound, and determining the ability of the test compound to interact with a Sprouty protein, wherein determining the ability of the test compound to interact with a Sprouty protein includes determining the ability of the test compound to preferentially bind to Sprouty or biologically active portion thereof, or to decrease the activity the Sprouty binding molecule, as compared to the known compound.

Compounds that disrupt the interaction of Sprouty with a naturally-occurring Sprouty binding molecule can be useful for regulating the activity of the Sprouty protein. Such compounds can include, but are not limited to, molecules such as antibodies, peptides, peptidomimetics, and small molecules (non-nucleic acid molecules and nucleic-acid molecules).

Provided herein are also methods for determining the ability of the test compound to decrease the activity of a Sprouty protein through modulation of the activity of a downstream effector of a Sprouty target molecule. For example, the activity of an effector molecule such as EGFR on an appropriate target can be determined, or the binding of the effector to an appropriate target can be determined, as described herein and as is known in the art.

To identify a compound that can interfere with the interaction between the a Sprouty protein and its cellular or extracellular binding partner(s) (i.e., a Sprouty binding molecule), a reaction mixture containing the Sprouty protein and the binding partner is prepared, under conditions and for a time sufficient, to allow the two products to form complex. To test an inhibitory agent, the reaction mixture is provided in the presence and absence of the test compound. The test compound can be initially included in the reaction mixture (a competition assay), or can be added at a time subsequent to the addition of the target gene and its cellular or extracellular binding partner (displacement assay). Control reaction mixtures are incubated without the test compound or with a compound that does not interact with the Sprouty protein or the binding partner. The formation of any complexes between a Sprouty protein and the cellular or extracellular binding partner is then detected. The formation of a complex in the control reaction, but not in the reaction mixture containing the test compound, indicates that the compound interferes with the interaction of the Sprouty protein and the interactive binding partner. Additionally, complex formation within reaction mixtures containing the test compound and normal Sprouty can also be compared to complex formation within reaction mixtures containing the test compound and a mutant Sprouty. This comparison can be important in those cases wherein it is desirable to identify compounds that disrupt interactions of a mutant but not normal (wild type) Sprouty protein.

Assays can be conducted in a heterogeneous or homogeneous format. Heterogeneous assays involve anchoring either a Sprouty protein or a Sprouty binding molecule onto a solid phase, and detecting complexes anchored on the solid phase at the end of the reaction. In homogeneous assays, the entire reaction is carried out in a liquid phase. In either approach, the order of addition of reactants can be varied to obtain different information about the compounds being tested. For example, test compounds that interfere with the interaction between the Sprouty protein and the binding partner, e.g., by competition, can be identified by conducting the reaction in the presence of the test substance. Alternatively, test compounds that disrupt preformed complexes, e.g., compounds with higher binding constants that displace one of the components from the complex, can be tested by adding the test compound to the reaction mixture after complexes have been formed.

In a heterogeneous assay system, either the Sprouty protein or the interactive cellular or extracellular binding partner, is anchored onto a solid surface (e.g., a microtiter plate), while the non-anchored species is labeled, either directly or indirectly. The anchored species can be immobilized by non-covalent or covalent attachments. Alternatively, an immobilized antibody specific for the species to be anchored can be used to anchor the species to the solid surface.

To conduct the assay, the partner of the immobilized species is exposed to the coated surface with or without the test compound. After the reaction is complete, unreacted components are removed (e.g., by washing) and any complexes formed remain immobilized on the solid surface. Where the non-immobilized species is pre-labeled, the detection of label immobilized on the surface indicates that complexes were formed. Where the non-immobilized species is not pre-labeled, an indirect label can be used to detect complexes anchored on the surface; e.g., using a labeled antibody specific for the initially non-immobilized species (the antibody, in turn, can be directly labeled or indirectly labeled with, e.g., a labeled anti-Ig antibody). Depending upon the order of addition of reaction components, test compounds that inhibit complex formation or that disrupt preformed complexes can be detected.

Alternatively, the reaction can be conducted in a liquid phase in the presence or absence of the test compound, the reaction products separated from unreacted components, and complexes detected; e.g., using an immobilized antibody specific for one of the binding components to anchor any complexes formed in solution, and a labeled antibody specific for the other partner to detect anchored complexes. Again, depending upon the order of addition of reactants to the liquid phase, test compounds that inhibit complex or that disrupt preformed complexes can be identified.

In some cases, a homogeneous assay can be used. For example, a preformed complex of the Sprouty protein and a cellular or extracellular binding partner product is prepared in that either the Sprouty protein or the binding partner is labeled, but the signal generated by the label is quenched due to complex formation (see, e.g., U.S. Pat. No. 4,109,496 that utilizes this approach for immunoassays). The addition of a test substance that competes with and displaces one of the species from the preformed complex results in the generation of a signal above background. In this way, test substances that disrupt Sprouty protein-binding partner interaction can be identified.

In another embodiment of the present invention, modulators of Sprouty expression are identified. For example, a cell or cell free mixture is contacted with a test compound and the expression of Sprouty mRNA or protein evaluated relative to the level of expression of Sprouty mRNA or protein in the absence of the test compound. When expression of Sprouty mRNA or protein is greater in the presence of the test compound than in its absence, the test compound is identified as a stimulator of Sprouty mRNA or protein expression. Alternatively, when expression of Sprouty mRNA or protein is less (statistically significantly less) in the presence of the test compound than in its absence, the test compound is identified as an inhibitor of Sprouty mRNA or protein expression. The level of Sprouty mRNA or protein expression can be determined by methods described herein for detecting Sprouty mRNA or protein.

In another aspect, the invention pertains to a combination of two or more of the assays described herein. For example, a modulating agent can be identified using a cell-based or a cell free assay, and the ability of the agent to decrease the activity of a Sprouty protein can be confirmed in vivo, e.g., in an animal such as an animal model for pancreatic cancer or fibrosarcoma. Examples of animal models that are useful in the invention include, without limitation, models such as those described in Lou et al. (2005) Cancer Res. 65:1007-1017; Linden et al. (2005) Leuk. Res. 29:435-44; and Morioka et al. (2004) In vivo 18:113-117.

Aspects of this invention further pertain to novel agents identified using the screening assays described herein. Accordingly, it is within the scope of this invention to further use an agent identified as described herein (e.g., a Sprouty modulating agent, an antisense Sprouty nucleic acid molecule, or a Sprouty-specific antibody) in an appropriate animal model to determine the efficacy, toxicity, side effects, or mechanism of action, for treatment with such an agent. Furthermore, novel agents identified by the screening assays can be used for treatments as described herein.

Nucleic Acid Compounds for Inhibiting Sprouty Expression or Activity

Antisense Nucleic Acid Molecules, Ribozymes, siRNAs, and Aptamers

Compounds that can be tested for the ability to decrease Sprouty expression or activity include nucleic acid molecules, including, without limitation, small inhibitory RNAs (siRNA, including short hairpin RNA (shRNA)), antisense RNAs, ribozymes, and triple helix oligonucleotides. In general, such molecules can be designed and synthesized using methods known in the art, and/or can generally be obtained from commercial sources (e.g., Dharmacon, Lafayette, Colo.; Open Biosystems, Huntsville, Ala.; and Ambion, Austin, Tex.).

Isolated nucleic acid molecules that are antisense to a Sprouty nucleotide sequence are useful for reducing activity or expression of the Sprouty mRNA or polypeptide. An "antisense" nucleic acid (antisense oligonucleotide) can include a nucleotide sequence that is complementary to a "sense" nucleic acid encoding a protein, e.g., complementary to the coding strand of a double-stranded cDNA molecule, or complementary to an mRNA sequence. The antisense nucleic acid can be complementary to an entire Sprouty coding strand, or to only a portion thereof (e.g., coding region of a human Sprouty nucleotide sequence). In another embodiment, the antisense nucleic acid molecule is antisense to a "noncoding region" of the coding strand of a nucleotide sequence encoding a Sprouty polypeptide (e.g., the 5' or 3' untranslated regions).

An antisense nucleic acid can be designed such that it is complementary to the entire coding region of Sprouty mRNA, but in general, is an oligonucleotide that is antisense to only a portion of the coding or noncoding region of Sprouty mRNA. For example, the antisense oligonucleotide can be complementary to the region surrounding the translation start site of Sprouty mRNA, e.g., between the −10 and +10 regions of the target gene nucleotide sequence of interest. An antisense oligonucleotide can be, e.g., about 5-100 or from about 7, 10, 15, 20, 25, 30, 35, 40, 45, 50, 55, 60, 65, 70, 75, 80, or more nucleotides in length.

An antisense nucleic acid can be constructed using chemical synthesis and enzymatic ligation reactions using procedures known in the art. For example, an antisense nucleic acid (e.g., an antisense oligonucleotide) can be chemically synthesized using naturally occurring nucleotides or variously modified nucleotides designed to increase the biological stability of the molecules or to increase the physical stability of the duplex formed between the antisense and sense nucleic acids, e.g., phosphorothioate derivatives and acridine substituted nucleotides can be used (see, e.g., Agrawal, ed. *Protocols for Olijonucleotides and Analogs*. Totowa, N.J.: Humana Press, 1993; *Protocols for Oligonucleotide Conjugates*. Totowa, N.J.: Humana Press, 1994; and commercially available services from, for example, Dharmacon, Lafayette, Colo. and Ambion, Austin, Tex.). The antisense nucleic acid also can be produced biologically using an expression vector into which a nucleic acid has been subcloned in an antisense orientation (i.e., RNA transcribed from the inserted nucleic acid will be of an antisense orientation to a target nucleic acid of interest, described further in the following subsection). Antisense nucleic acids can also be produced from synthetic methods such as phosphoramidite methods, H-phosphonate methodology, and phosphite trimester methods. Antisense nucleic acids can also be produced by PCR methods. Such methods produce cDNA and cRNA sequences complementary to the mRNA.

In certain embodiments, antisense molecules can be modified or unmodified RNA, DNA, or mixed polymer oligonucleotides and primarily function by specifically binding to matching sequences resulting in inhibition of peptide synthesis (Wu-Pong (November 1994) *BioPharm.* 20:33). The antisense oligonucleotide binds to target RNA by Watson Crick base-pairing and blocks gene expression by preventing ribosomal translation of the bound sequences either by steric blocking or by activating RNase H enzyme. Antisense molecules can also alter protein synthesis by interfering with RNA processing or transport from the nucleus into the cytoplasm (Mukhopadhyay & Roth (1996) *Crit. Rev. Oncogen.* 7:151-190).

An antisense nucleic acid can be an α-anomeric nucleic acid molecule. An α-anomeric nucleic acid molecule forms specific double-stranded hybrids with complementary RNA in which, contrary to the usual β-units, the strands run parallel to each other (Gaultier et al. (1987) *Nucleic Acids. Res.* 15:6625-6641). The antisense nucleic acid molecule can also comprise a 2'-O-methylribonucleotide (Inoue et al. (1987) *Nucleic Acids Res.* 15:6131-6148) or a chimeric RNA-DNA analog (Inoue et al. (1987) *FEBS Lett.* 215:327-330), and can have mixed internucleoside linkages (see, e.g., Agrawal, ed. *Protocols for Oligonucleotides and Analogs*. Totowa, N.J.: Humana Press, 1993; *Protocols for Oligonucleotide Conjugates*. Totowa N.J.: Humana Press, 1994).

For treatment protocols, antisense nucleic acid molecules are typically administered to a subject (e.g., by direct injection at a tissue site), or are generated in situ such that they hybridize with or bind to cellular RNA (e.g., mRNA) and/or genomic DNA encoding a Sprouty protein to thereby inhibit expression of the protein, e.g., by inhibiting transcription and/or translation. Alternatively, antisense nucleic acid molecules can be modified to target selected cells and then administered systemically. For systemic administration, antisense molecules can be modified such that they specifically bind to receptors or antigens expressed on a selected cell surface, e.g., by linking the antisense nucleic acid molecules to peptides or antibodies that bind to cell surface receptors or antigens. The antisense nucleic acid molecules can also be delivered to cells using the vectors described herein. To achieve sufficient intracellular concentrations of the antisense molecules, vector constructs in which the antisense nucleic acid molecule is placed under the control of a strong pol II or pol III promoter are generally used. Methods of administering antisense nucleic molecules are also known in the art (e.g., Wacheck et al. (2000) *Lancet* 356:1728-1733; Webb et al. (1997) *Lance* 349:1137-1141.

Sprouty gene expression can be inhibited by targeting nucleotide sequences complementary to the regulatory region of the Sprouty (e.g., the Sprouty promoter and/or enhancers) to form triple helical structures that prevent transcription of the Sprouty gene in target cells (see generally, Helene (1991) *Anticancer Drug Des.* 6(6):569-84; Helene et al. (1992) *Ann. N.Y. Acad. Sci.* 660:27-36; and Maher (1992) *Bioassays* 14:807-15). The potential sequences that can be targeted for triple helix formation can be increased by creating a so-called "switchback" nucleic acid molecule. Switchback molecules are synthesized in an alternating 5'-3', 3'-5' manner, such that they base pair with first one strand of a duplex and then the other, eliminating the necessity for a sizeable stretch of either purines or pyrimidines to be present on one strand of a duplex.

A Sprouty nucleic acid molecule can be modified at the base moiety, sugar moiety or phosphate backbone to improve, e.g., the stability, hybridization, or solubility of the molecule. For example, the deoxyribose phosphate backbone of the nucleic acid molecules can be modified to generate peptide nucleic acids (see Hyrup et al. (1996) *Bioorgan. Med. Chem.* 4:5-23). As used herein, the terms "peptide nucleic acid" or "PNA" refer to a nucleic acid mimic, e.g., a DNA mimic, in which the deoxyribose phosphate backbone is replaced by a pseudopeptide backbone and only the four natural nucleobases are retained. The neutral backbone of a PNA can allow for specific hybridization to DNA and RNA under conditions of low ionic strength. The synthesis of PNA oligomers can be performed using standard solid phase peptide synthesis protocols as described in Hyrup et al. (1996, supra) and Perry-O'Keefe et al. (1996) *Proc. Natl. Acad. Sci. U.S.A.* 93:14670-14675).

PNAs of Sprouty nucleic acid molecules can be used in therapeutic and diagnostic applications. For example, PNAs can be used as antisense or antigene agents for sequence-specific modulation of gene expression by, for example, inducing transcription or translation arrest or inhibiting replication. PNAs of Sprouty nucleic acid molecules can also be used in the analysis of single base pair mutations in a gene, (e.g., by PNA-directed PCR clamping); as "artificial restriction enzymes" when used in combination with other enzymes, (e.g., S1 nucleases (Hyrup (1996, supra)); or as probes or primers for DNA sequencing or hybridization (Hyrup et al. (1996, supra); Perry-O'Keefe et al. (1996, supra)).

The nucleic acid can include other appended groups such as peptides (e.g., for targeting host cell receptors in vivo), or agents facilitating transport across the cell membrane (e.g., Letsinger et al. (1989) *Proc. Natl. Acad. Sci. U.S.A.* 86:6553-6556; Lemaitre et al. (1987) *Proc. Natl. Acad. Sci. U.S.A.* 84:648-652; PCT Publ. No. W088/09810) or the blood-brain barrier (see, e.g., PCT Publication No. W089/10134). In addition, oligonucleotides can be modified with hybridization-triggered cleavage agents (e.g., Krol et al. (1988) *Bio-Techniques* 6:958-976) or intercalating agents (e.g., Zon (1988)

*Pharm. Res.* 5:539-549). To this end, the oligonucleotide can be conjugated to another molecule, (e.g., a peptide, hybridization triggered cross-linking agent, transport agent, or hybridization-triggered cleavage agent).

Also useful in the methods described herein are molecular beacon oligonucleotide primer and probe molecules having at least one region that is complementary to a Sprouty nucleic acid of the invention, two complementary regions, one having a fluorophore and one a quencher such that the molecular beacon is useful for quantitating the presence of the Sprouty nucleic acid of the invention in a sample. Molecular beacon nucleic acids are described, for example, in U.S. Pat. Nos. 5,854,033, 5,866,336 and 5,876,930.

RNA interference (RNAi) is a process whereby double-stranded RNA (dsRNA) induces the sequence-specific degradation of homologous mRNA in animals and plant cells (Hutvagner and Zamore (2002) *Curr. Opin. Genet. Dev.* 12225-12232; Sharp (2001) *Genes Dev.* 15:485-490). Thus, methods using molecules that can act in RNAi can be used to regulate protein expression of a targeted sequence. In mammalian cells, RNAi can be triggered by, e.g., approximately 21-nucleotide (nt) duplexes of small interfering RNA (siRNA) (Chiu et al. (2002) *Mol. Cell.* 10:549-561; Elbashir et al. (2001) *Nature* 411:494-498), or by micro-RNAs (miRNA), functional small-hairpin RNA (shRNA), or other dsRNAs which are expressed in vivo using DNA templates with RNA polymerase III promoters (Zeng et al. (2002) *Mol. Cell* 9:1327-1333; Paddison et al. (2002) *Genes Dev.* 16:948-958; Lee et al. (2002) *Nature Biotechnol.* 20:500-505; Paul et al. (2002) *Nature Biotechnol.* 20:505-508; Tuschl (2002) *Nature Biotechnol.* 20:440-448; Yu et al. (2002) *Proc. Natl. Acad. Sci. U.S.A.* 99:6047-6052; McManus et al. (2002) *RNA* 8:842-850; Sui et al. (2002) *Proc. Natl. Acad. Sci. U.S.A.* 99:5515-5520).

Methods of using siRNA to inhibit gene expression are well known in the art (see e.g., U.S. Pat. No. 6,506,559). Typically, complementary RNA sequences that can hybridize to a specific region of the target RNA are introduced into the cell. RNA annealing to the target transcripts allows the internal machinery of the cell to cut the dsRNA sequences into short segments. Such mechanisms have been utilized in in vitro and in vivo studies of human genes (see, e.g., Mizutani et al. (2002) *J. Biol. Chem.* 277(18): 15859-64; Wang et al. (2005) *Breast Cancer Res.* 7(2):R220-8).

Examples of molecules that can be used to decrease expression of a Sprouty include double-stranded RNA (dsRNA) molecules that can function as siRNAs and that comprise 16-30, e.g., 16, 17, 18, 19, 20, 21, 22, 23, 24, 25, 26, 27, 28, 29, or 30 nucleotides in each strand, wherein one of the strands is substantially complementary to, e.g., at least 80% (or more, e.g., 85%, 90%, 95%, or 100%) complementary to, e.g., having for example 3, 2, 1, or 0 mismatched nucleotide(s), a target region, e.g., a transcribed region of a Sprouty nucleic acid, and the other strand is identical or substantially identical to the first strand. The dsRNA molecules can be chemically synthesized, or can be transcribed in vitro from a DNA template, or in vivo from an engineered RNA precursor, e.g., shRNA.

The dsRNA molecules can be designed using methods known in the art (e.g., "The siRNA User Guide," available at rockefeller.edu/labheads/tuschl/siRNA) and can be obtained from commercial sources, e.g., Dharmacon, Inc. (Lafayette, Colo.) and Ambion, Inc. (Austin, Tex.). Small-interfering RNAs can be obtained by any means known in the art. For example, they can be synthetically produced using the Expedite™ Nucleic Acid Synthesizer (Applied Biosystems, Foster City, Calif.) or other similar devices (see, e.g., Applied Biosystems, Foster City, Calif.). Synthetic oligonucleotides also can be produced using methods well known in the art such as phosphoramidite methods (see, e.g., Pan et. al. (2004) *Biol. Proc. Online* 6:257-262), H-phosphonate methodology (see, e.g., Agrawal et. al. (1987) *Tetrahedron Lett.* 28(31): 3539-3542) and phosphite trimester methods (Finnan et al. (1980) *Nucleic Acids Symp. Ser.* (7):133-45).

Negative control siRNAs generally have the same nucleotide composition as the selected siRNA, but without significant sequence complementarity to the targeted genome. Such negative controls can be designed by randomly scrambling the nucleotide sequence of the selected siRNA; a homology search can be performed to ensure that the negative control lacks homology to any other gene in the appropriate genome. In addition, negative control siRNAs can be designed by introducing one or more base mismatches into the sequence.

The siRNAs for use in the present invention as described herein can be delivered to a cell by methods known in the art and as described herein such as, but not limited to, transfection, e.g., utilizing commercially available kits and reagents. For example, viral infection, e.g., using a lentivirus vector, or adenovirus vector, can be used. In some cases, a commercially available viral delivery system can be used (see, e.g., vectors for siRNA delivery that are available from Ambion, Austin, Tex.). Other methods for delivery are known to those in the art (e.g., siRNA Delivery Centre, sirna.dk/index.html).

Still further compositions, methods and applications of RNAi technology for use as described herein are provided in U.S. Pat. Nos. 6,278,039, 5,723,750 and 5,244,805.

In addition to RNAi, enzymatic nucleic acid molecules that are directed against a Sprouty nucleotide sequence are useful for reducing activity or expression of the Sprouty mRNA or polypeptide. As used herein, the term "enzymatic nucleic acid molecules" means a nucleic acid molecule which has complementarity in a substrate binding region to a specified gene target, and also has an enzymatic activity which is active to specifically cleave target RNA. The enzymatic nucleic acid molecule is able to intermolecularly cleave RNA and thereby inactivate a target RNA molecule. These complementary regions allow sufficient hybridization of the enzymatic nucleic acid molecule to the target RNA and thus permit cleavage. 100% complementarity can be utilized, but complementarity as low as 50 75% can also be useful in this invention (see for example Werner and Uhlenbeck (1995) *Nucleic Acids Res.* 23:2092-2096; Hammann et al. (1999) *Antisense Nucl. Acid Drug Dev.* 9:25-31). The nucleic acids can be modified at the base, sugar, and/or phosphate groups. The term enzymatic nucleic acid is used interchangeably with phrases such as ribozymes, catalytic RNA, enzymatic RNA, catalytic DNA, aptazyme or aptamer-binding ribozyme, regulatable ribozyme, catalytic oligonucleotides, nucleozyme, DNAzyme, RNA enzyme, endoribonuclease, endonuclease, minizyme, leadzyme, oligozyme or DNA enzyme. All of these terminologies describe nucleic acid molecules with enzymatic activity.

The specific enzymatic nucleic acid molecules described in the instant application are not limiting in the invention and those skilled in the art will recognize that all that is important in an enzymatic nucleic acid molecule of this invention is that it has a specific substrate binding site which is complementary to one or more of the target nucleic acid regions, and that it have nucleotide sequences within or surrounding that substrate binding site which impart a nucleic acid cleaving and/or ligation activity to the molecule (U.S. Pat. No. 4,987,071; Cech et al. (1988) *JAMA* 260:3030).

Several varieties of enzymatic RNAs are presently known. In addition, several in vitro selection (evolution) strategies (Orgel (1979) *Proc. R. Soc. London* B 205:435) have been used to evolve new nucleic acid catalysts capable of catalyzing cleavage and ligation of phosphodiester linkages (Joyce (1989) *Gene* 82:83-87; Beaudry et al. (1992) *Science* 257:635-641; Joyce (1992) *Sci. Am.* 267:90-97; Breaker et al. (1994) *TIBTECH* 12:268; Bartel et al. (1993) *Science* 261: 1411-1418; Szostak (1993) *TIBS* 17:89-93; Kumar et al. (1995) *FASEB J.* 9:1183; Breaker (1996) *Curr. Op. Biotech.* 7:442; Santoro et al. (1997) *Proc. Natl. Acad. Sci.* 94:4262; Tang et al. (1997) *RNA* 3:914; Nakacane & Eckstein (1994, supra); Long & Uhlenbeck (1994, supra); Ishizaka et al. (1995, supra); Vaish et al. (1997) *Biochem.* 36:6495). Each can catalyze a series of reactions including the hydrolysis of phosphodiester bonds in trans (and thus can cleave other RNA molecules) under physiological conditions.

In specific embodiments, the enzymatic nucleic acid molecule is a ribozyme having specificity for a Sprouty-encoding nucleic acid can include one or more sequences complementary to the nucleotide sequence of a Sprouty cDNA and a sequence having known catalytic sequence responsible for mRNA cleavage (see, for example, U.S. Pat. No. 5,093,246 or Haselhoff et al. (1988) *Nature* 334:585-591). For example, a derivative of a Tetrahymena L-19 IVS RNA can be constructed in which the nucleotide sequence of the active site is complementary to the nucleotide sequence to be cleaved in a Sprouty-encoding mRNA (see, e.g., U.S. Pat. Nos. 4,987,071 and 5,116,742). Alternatively, Sprouty mRNA can be used to select a catalytic RNA having a specific ribonuclease activity from a pool of RNA molecules (e.g., Bartel et al. (1993) *Science* 261:1411-1418).

Nucleic acid molecules of this invention will block to some extent Sprouty expression and can be used to treat disease or diagnose disease associated with the levels of Sprouty. The enzymatic nature of an enzymatic nucleic acid molecule can allow the concentration of enzymatic nucleic acid molecule necessary to affect a therapeutic treatment to be lower. This reflects the ability of the enzymatic nucleic acid molecule to act enzymatically. Thus, a single enzymatic nucleic acid molecule is able to cleave many molecules of target RNA. In addition, the enzymatic nucleic acid molecule is a highly specific inhibitor, with the specificity of inhibition depending not only on the base-pairing mechanism of binding to the target RNA, but also on the mechanism of target RNA cleavage. Single mismatches, or base-substitutions, near the site of cleavage can be chosen to greatly attenuate the catalytic activity of an enzymatic nucleic acid molecule.

Nucleic acid molecules having an endonuclease enzymatic activity are able to repeatedly cleave other separate RNA molecules in a nucleotide base sequence-specific manner. Such enzymatic nucleic acid molecules can be targeted to virtually any RNA transcript, and achieve efficient cleavage in vitro (Zaug et al. (1986) *Nature* 324:429; Uhlenbeck (1987) *Nature* 328:596; Kim et al. (1987) *Proc. Natl. Acad. Sci. U.S.A.* 84:8788; Dreyfus (1988) *Einstein Quart. J. Bio. Med.* 6:92; Haseloff and Gerlach (1988) *Nature* 334:585; Cech (1988) *JAMA* 260:3030; and Jefferies et al. (1989) *Nucleic Acids Res.* 17:1371; Santoro et al. (1997, supra)).

Because of their sequence specificity, trans-cleaving enzymatic nucleic acid molecules can be used as therapeutic agents for human disease (Usman & McSwiggen (1995), *Ann. Rep. Med. Chem.* 30:285-294; Christoffersen and Marr (1995) *J. Med. Chem.* 38:2023-2037). Enzymatic nucleic acid molecules can be designed to cleave specific RNA targets within the background of cellular RNA. Such a cleavage event renders the RNA non-functional and abrogates protein expression from that RNA. In this manner, synthesis of a protein associated with a disease state can be selectively inhibited (Warashina et al. (1999) *Chem. Biol.* 6:237-250).

In certain embodiments, enzymatic nucleic acid molecules can be allosterically regulated ("allozymes") to modulate Sprouty expression. These allosteric enzymatic nucleic acids or allozymes (see for example U.S. Pat. Nos. 5,834,186, 5,741,679, 5,589,332 and 5,871,914, PCT Pub. Nos. WO 00/24931, WO 00/26226, WO 98/27104, and WO 99/29842) are designed to respond to a signaling agent, for example, mutant Sprouty protein, wild-type Sprouty protein, mutant Sprouty RNA, other proteins and/or RNAs involved in Sprouty activity, compounds, metals, polymers, molecules and/or drugs that are targeted to Sprouty, which in turn modulates the activity of the enzymatic nucleic acid molecule. In response to interaction with a predetermined signaling agent, the allosteric enzymatic nucleic acid molecule's activity is activated or inhibited such that the expression of a particular target is selectively down-regulated. The target can comprise wild-type Sprouty, mutant Sprouty, a component of Sprouty, and/or a predetermined cellular component that modulates Sprouty activity. In a specific example, allosteric enzymatic nucleic acid molecules that are activated by interaction with a RNA encoding a mutant Sprouty protein are used as therapeutic agents in vivo. The presence of RNA encoding the mutant Sprouty activates the allosteric enzymatic nucleic acid molecule that subsequently cleaves the RNA encoding a mutant Sprouty protein resulting in the inhibition of mutant Sprouty protein expression. In this manner, cells that express the mutant form of the Sprouty protein are selectively targeted. Such an approach, can be used to treat, for example, incontinentia pigmenti.

In another non-limiting example, an allozyme can be activated by a Sprouty protein, peptide, or mutant polypeptide that caused the allozyme to inhibit the expression of Sprouty gene, by, for example, cleaving RNA encoded by Sprouty gene. In this non-limiting example, the allozyme acts as a decoy to inhibit the function of Sprouty and also inhibit the expression of Sprouty once activated by the Sprouty protein.

Another method by which nucleic acid molecules can be utilized in treating or preventing a disease characterized by Sprouty expression is through the use of aptamer molecules specific for a Sprouty protein. Aptamers are nucleic acid molecules having a tertiary structure that permits them to specifically bind to protein ligands (see, e.g., Osborne et al. (1997) *Curr. Opin. Chem. Biol.* 1:5-9; and Patel (1997) *Curr. Opin. Chem. Biol.* 1:32-46). Since nucleic acid molecules can in many cases be more conveniently introduced into target cells than therapeutic protein molecules can be, aptamers offer a method by which Sprouty protein activity can be specifically decreased without the introduction of drugs or other molecules which can have pluripotent effects.

The term "aptamer," used herein interchangeably with the term "nucleic acid ligand," means a nucleic acid that, through its ability to adopt a specific three-dimensional conformation, binds to and has an antagonizing (i.e., inhibitory) effect on a target. The target of the present invention is Sprouty, and hence the term Sprouty aptamer or nucleic acid ligand is used. Inhibition of the target by the aptamer can occur by binding of the target, by catalytically altering the target, by reacting with the target in a way which modifies/alters the target or the functional activity of the target, by covalently attaching to the target as in a suicide inhibitor, by facilitating the reaction between the target and another molecule. Aptamers can be comprised of multiple ribonucleotide units, deoxyribonucleotide units, or a mixture of both types of nucleotide residues. Aptamers can further comprise one or more modified bases, sugars or phosphate backbone units as described above.

Aptamers can be made by any known method of producing oligomers or oligonucleotides. Many synthesis methods are known in the art. For example, 2'-O-allyl modified oligomers that contain residual purine ribonucleotides, and bearing a suitable 3'-terminus such as an inverted thymidine residue (Ortigao et al. (1992) *Antisense Res. Devel.* 2:129-146) or two phosphorothioate linkages at the 3'-terminus to prevent eventual degradation by 3'-exonucleases, can be synthesized by solid phase beta-cyanoethyl phosphoramidite chemistry (Sinha et al. (1984) *Nucleic Acids Res.* 12:4539-4557) on any commercially available DNA/RNA synthesizer. One method is the 2'-O-tert-butyldimethylsilyl (TBDMS) protection strategy for the ribonucleotides (Usman et al., (1987) *J. Am. Chem. Soc.* 109:7845-7854), and all the required 3'-O-phosphoramidites are commercially available. In addition, aminomethylpolystyrene can be used as the support material due to its advantageous properties (McCollum and Andrus (1991) *Tetrahedron Lett.* 32:4069-4072). Fluorescein can be added to the 5'-end of a substrate RNA during the synthesis by using commercially available fluorescein phosphoramidites. In general, an aptamer oligomer can be synthesized using a standard RNA cycle. Upon completion of the assembly, all base labile protecting groups are removed by an 8 hr. treatment at 55° C. with concentrated aqueous ammonia/ethanol (3:1 v/v) in a sealed vial. The ethanol suppresses premature removal of the 2'-O-TBDMS groups that would otherwise lead to appreciable strand cleavage at the resulting ribonucleotide positions under the basic conditions of the deprotection (Usman et al. (1987) *J. Am. Chem. Soc.* 109:7845-7854). After lyophilization, the TBDMS protected oligomer is treated with a mixture of triethylamine trihydrofluoride/triethylamine/N-methylpyrrolidinone for 2 hrs. at 60° C. to afford fast and efficient removal of the silyl protecting groups under neutral conditions (see, e.g., Wincott et al. (1995) *Nucleic Acids Res.* 23:2677-2684). The fully deprotected oligomer can then be precipitated with butanol according to the procedure of Cathala and Brunel ((1990) *Nucleic Acids Res.* 18:201). Purification can be performed either by denaturing polyacrylamide gel electrophoresis or by a combination of ion-exchange HPLC (Sproat et al. (1995) *Nucleosides Nucleotides* 14:255-273) and reversed phase HPLC. For use in cells, synthesized oligomers are converted to their sodium salts by precipitation with sodium perchlorate in acetone. Traces of residual salts can then be removed using small disposable gel filtration columns that are commercially available. As a final step the authenticity of the isolated oligomers can be checked by matrix assisted laser desorption mass spectrometry (Pieles et al. (1993) *Nucleic Acids Res.* 21:3191-3196) and by nucleoside base composition analysis.

The disclosed aptamers can also be produced through enzymatic methods, when the nucleotide subunits are available for enzymatic manipulation. For example, the RNA molecules can be made through in vitro RNA polymerase T7 reactions. They can also be made by strains of bacteria or cell lines expressing T7, and then subsequently isolated from these cells. As discussed below, the disclosed aptamers can also be expressed in cells directly using vectors and promoters.

The stability of the aptamer can be greatly increased by the introduction of such modifications and as well as by modifications and substitutions along the phosphate backbone of the RNA. In addition, a variety of modifications can be made on the nucleobases themselves, which both inhibit degradation and which can increase desired nucleotide interactions or decrease undesired nucleotide interactions (see above).

Nucleic acids of the present invention can also include modified bases. Modifications include the incorporation of modified bases (or modified nucleoside or modified nucleotides) that are variations of standard bases, sugars and/or phosphate backbone chemical structures occurring in ribonucleic (i.e., A, C, G and U) and deoxyribonucleic (i.e., A, C, G and T) acids. Included within this scope are, for example: Gm (2'-methoxyguanylic acid), Am (2'-methoxyadenylic acid), Cf (2'-fluorocytidylic acid), Uf (2'-fluorouridylic acid), Ar (riboadenylic acid). Nucleic acids can also include cytosine or any cytosine-related base including 5-methylcytosine, 4-acetylcytosine, 3-methylcytosine, 5-hydroxymethyl cytosine, 2-thiocytosine, 5-halocytosine (e.g., 5-fluorocytosine, 5-bromocytosine, 5-chlorocytosine, and 5-iodocytosine), 5-propynyl cytosine, 6-azocytosine, 5-trifluoromethylcytosine, N4, N4-ethanocytosine, phenoxazine cytidine, phenothiazine cytidine, carbazole cytidine or pyridoindole cytidine. The aptamer can further include guanine or any guanine-related base including 6-methylguanine, 1-methylguanine, 2,2-dimethylguanine, 2-methylguanine, 7-methylguanine, 2-propylguanine, 6-propylguanine, 8-haloguanine (e.g., 8-fluoroguanine, 8-bromoguanine, 8-chloroguanine, and 8-iodoguanine), 8-aminoguanine, 8-sulfhydrylguanine, 8-thioalkylguanine, 8-hydroxylguanine, 7-methylguanine, 8-azaguanine, 7-deazaguanine or 3-deazaguanine. The aptamer can still further include adenine or any adenine-related base including 6-methyladenine, N6-isopentenyladenine, N6-methyladenine, 1-methyladenine, 2-methyladenine, 2-methylthio-N6-isopentenyladenine, 8-haloadenine (e.g., 8-fluoroadenine, 8-bromoadenine, 8-chloroadenine, and 8-iodoadenine), 8-aminoadenine, 8-sulfhydryladenine, 8-thioalkyladenine, 8-hydroxyladenine, 7-methyladenine, 2-haloadenine (e.g., 2-fluoroadenine, 2-bromoadenine, 2-chloroadenine, and 2-iodoadenine), 2-aminoadenine, 8-azaadenine, 7-deazaadenine or 3-deazaadenine. Also included are uracil or any uracil-related base including 5-halouracil (e.g., 5-fluorouracil, 5-bromouracil, 5-chlorouracil, 5-iodouracil), 5-(carboxyhydroxylmethyl)uracil, 5-carboxymethylaminomethyl-2-thiouracil, 5-carboxymethylaminomethyluracil, dihydrouracil, 1-methylpseudouracil, 5-methoxyaminomethyl-2-thiouracil, 5'-methoxycarbonylmethyluracil, 5-methoxyuracil, 5-methyl-2-thiouracil, 2-thiouracil, 4-thiouracil, 5-methyluracil, uracil-5-oxyacetic acid methylester, uracil-5-oxyacetic acid, pseudouracil, 5-methyl-2-thiouracil, 2-thiouracil, 3-(3-amino-3-N-2-carboxypropyl)uracil, 5-methylaminomethyluracil, 5-propynyl uracil, 6-azouracil, or 4-thiouracil.

Nonlimiting examples of other modified base variants known in the art include, without limitation, e.g., 4-acetylcytidine, 5-(carboxyhydroxylmethyl) uridine, 2'-methoxycytidine, 5-carboxymethylaminomethyl-2-thioridine, 5-carboxymethylaminomethyluridine, dihydrouridine, 2'-O-methylpseudouridine, b-D-galactosylqueosine, inosine, N6-isopentenyladenosine, 1-methyladenosine, 1-methylpseudouridine, 1-methylguanosine, 1-methylinosine, 2,2-dimethylguanosine, 2-methyladenosine, 2-methylguanosine, 3-methylcytidine, 5-methylcytidine, N6-methyladenosine, 7-methylguanosine, 5-methylaminomethyluridine, 5-methoxyaminomethyl-2-thiouridine, b-D-mannosylqueosine, 5-methoxycarbonylmethyluridine, 5-methoxyuridine, 2-methylthio-N6-isopentenyladenosine, N-((9-b-D-ribofuranosyl-2-methylthiopurine-6-yl)carbamoyl)threonine, N-((9-b-D-ribofuranosylpurine-6-yl)N-methyl-carbamoyl)threonine, uridine-5-oxyacetic acid methylester, uridine-5-oxyacetic acid (v), wybutoxosine, pseudouridine, queosine, 2-thiocytidine, 5-methyl-2-thiouridine, 2-thiouridine, 4-thiouridine, 5-methyluridine, N-((9-b-D-ribofuranosylpurine-6-yl)carbamoyl)threonine, 2'-O-methyl-5-methyluridine, 2'-O-methyluridine, and wybutosine, 3-(3-amino-3-carboxypropyl) uridine.

Also included are the modified nucleobases described in U.S. Pat. Nos. 3,687,808, 3,687,808, 4,845,205, 5,130,302, 5,134,066, 5,175,273, 5,367,066, 5,432,272, 5,457,187, 5,459,255, 5,484,908, 5,502,177, 5,525,711, 5,552,540, 5,587,469, 5,594,121, 5,596,091, 5,614,617, 5,645,985, 5,830,653, 5,763,588, 6,005,096, and 5,681,941. Examples of modified nucleoside and nucleotide sugar backbone variants known in the art include, without limitation, those having, e.g., 2' ribosyl substituents such as F, SH, $SCH_3$, OCN, Cl, Br, CN, $CF_3$, $OCF_3$, $SOCH_3$, $SO_2$, $CH_3$, $ONO_2$, $NO_2$, $N_3$, $NH_2$, $OCH_2CH_2OCH_3$, $O(CH_2)_2ON(CH_3)_2$, $OCH_2OCH_2N(CH_3)_2$, $O(C_{1-10}alkyl)$, $O(C_{2-10}alkenyl)$, $O(C_{2-10}alkynyl)$, $S(C_{1-10}alkyl)$, $S(C_{2-10}alkenyl)$, $S(C_{2-10}alkynyl)$, $NH(C_{1-10}alkyl)$, $NH(C_{2-10}alkenyl)$, $NH(C_{2-10}alkynyl)$, and O-alkyl-O-alkyl. Desirable 2' ribosyl substituents include 2'-methoxy (2'-$OCH_3$), 2'-aminopropoxy (2' $OCH_2CH_2CH_2NH_2$), 2'-allyl (2'-$CH_2$—CH=$CH_2$), 2'-O-allyl (2'-O—$CH_2$—CH=$CH_2$), 2'-amino (2'-$NH_2$), and 2'-fluoro (2'-F). The 2'-substituent can be in the arabino (up) position or ribo (down) position. Nucleic acids can be made up of nucleotides and/or nucleotide analogs such as described above, or a combination of both, or are oligonucleotide analogs.

The nucleic acid molecules described herein, including siRNA molecules, can also be labeled using any method known in the art; for instance, the nucleic acid compositions can be labeled with a fluorophore, e.g., Cy3, fluorescein, or rhodamine. The labeling can be carried out using a kit, e.g., the SILENCER™ siRNA labeling kit (Ambion Austin, Tex.). Additionally, an siRNA can be radiolabeled, e.g., using 3H, 32P, or other appropriate isotope.

Detectably labeled oligonucleotide primer and probe molecules are useful in the methods of the invention, e.g., diagnostic methods. Typically, such labels are chemiluminescent, fluorescent, radioactive, or colorimetric. Such probe molecules can be detectably labeled, with, e.g., fluorophores (e.g., fluorescein (FITC), phycoerythrin, rhodamine), chemical dyes, or compounds that are radioactive, chemoluminescent, magnetic, paramagnetic, promagnetic, or enzymes that yield a product that can be colored, chemoluminescent, or magnetic. The signal is detectable by any suitable means, including spectroscopic, photochemical, biochemical, immunochemical, electrical, optical or chemical means. In certain cases, the signal is detectable by two or more means. Nucleic acid labels may include fluorescent dyes, radiolabels, and chemiluminescent labels, which are examples that are not intended to limit the scope of the invention (see, e.g., Yu, et al. (1994) *Nucleic Acids Res.* 22(16): 3226-3232; Zhu, et al. (1994) *Nucleic Acids Res.* 22(16): 3418-3422).

Probe molecules can be detectably labeled using fluorescent labels. Non-limiting examples of fluorescent labels include 1- and 2-aminonaphthalene, p,p'diaminostilbenes, pyrenes, quaternary phenanthridine salts, 9-aminoacridines, p,p'-diaminobenzophenone imines, anthracenes, oxacarbocyanine, marocyanine, 3-aminoequilenin, perylene, bis-benzoxazole, bis-p-oxazolyl benzene, 1,2-benzophenazin, retinol, bis-3-aminopridinium salts, hellebrigenin, tetracycline, sterophenol, benzimidazolyl phenylamine, 2-oxo-3-chromen, indole, xanthen, 7-hydroxycoumarin, phenoxazine, salicylate, strophanthidin, porphyrins, triarylmethanes, flavin, xanthene dyes (e.g., fluorescein and rhodamine dyes); cyanine dyes; 4,4-difluoro-4-bora-3a,4a-diaza-s-indacene dyes and fluorescent proteins (e.g., green fluorescent protein, phycobiliprotein). These labels can be commercially obtained, e.g., from PerkinElmer Corp. (Boston, Mass.).

Other useful dyes are chemiluminescent dyes and can include, without limitation, biotin conjugated DNA nucleotides and biotin conjugated RNA nucleotides. Labeling of probe molecules can be accomplished by any means known in the art. (see, e.g., CyScribe™ First Strand cDNA Labeling Kit (#RPN6200, Amersham Biosciences, Piscataway, N.J.). The label can be added to the target nucleic acid(s) prior to, or after the hybridization. So called "direct labels" are detectable labels that are directly attached to, or incorporated into, the target nucleic acid prior to hybridization. In contrast, so called "indirect labels" are joined to the hybrid duplex after hybridization. Often, the indirect label is attached to a binding moiety that has been attached to the target nucleic acid prior to the hybridization. Thus, for example, the target nucleic acid can be biotinylated before the hybridization. After hybridization, an avidin-conjugated fluorophore binds the biotin bearing hybrid duplexes providing a label that is easily detected. (see, e.g., *Laboratory Techniques in Biochemistry and Molecular Biology*, Vol. 24: Hybridization With Probe Molecules. P. Tijssen, ed. NY: Elsevier, 1993).

Non-Nucleic Acid Compounds for Inhibiting Sprouty Expression or Activity

Peptide, Petidomimetic Compound, and Small Molecule

In addition, compounds such as peptides, peptidomimetic compounds, and small molecules can be tested for the ability to decrease Sprouty expression or activity. Inhibitors of Sprouty can be synthesized from peptides or other biomolecules including but not limited to saccharides, fatty acids, sterols, isoprenoids, purines, pyrimidines, derivatives or structural analogs of the above, or combinations thereof and the like. Phage display libraries and chemical combinatorial libraries can be used to develop and select synthetic compounds which are Sprouty inhibitors. Also envisioned in the invention is the use of inhibitors made from peptoids, random bio-oligomers (U.S. Pat. No. 5,650,489), benzodiazepines, diversomeres such as dydantoins, benzodiazepines and dipeptides, nonpeptidal peptidomimetics with a beta-D-glucose scaffolding, oligocarbamates or peptidyl phosphonates.

In certain examples, Sprouty expression or activity is inhibited by peptides that are designed to specifically interact, bind, or associate with the Sprouty protein or RNA. As used herein, the term "peptide" means a molecule comprising 200 or fewer amino acids bound together in any particular sequence. Such peptides can interact, associate, or bind with a particular amino acid sequence of the Sprouty polypeptide. Peptides can also interact, associate, or bind with an amino acid sequence of any other protein or nucleic acid that modulates the activity of Sprouty. Peptides can be subjected to directed or random chemical modifications such as acylation, alkylation, esterification, amidification, etc.

Identification of peptides that inhibit or antagonize Sprouty is facilitated by knowledge of the primary sequences of Sprty2. These primary sequences can provide an initial clue as to the inhibitors or antagonists of Sprouty. Identification and screening of peptide inhibitors is further facilitated by determining structural features of the Sprouty protein, e.g., using X-ray crystallography, neutron diffraction, nuclear magnetic resonance spectrometry, and other techniques for structure determination.

Peptide inhibitor identification is further facilitated by computer algorithms. Such computer algorithms are employed that are capable of scanning a database of peptides and small molecules of known three-dimensional structure for candidates that fit geometrically into the target proteins site. Most algorithms of this type provide a method for finding a wide assortment of chemical structures that are complementary to the shape of a binding pocket or region of a domain of a protein such as Sprouty. Each of a set of peptides from a particular database can be compared to determine the particular peptides that have the most potential for interacting with Sprouty.

Sometimes, a computer algorithm is utilized to search a for proteins or small molecules that can be oriented in a binding pocket or site in a way that is both sterically acceptable and has a high likelihood of achieving favorable chemical interactions between the candidate molecule and the surrounding amino acid residues. The method is based on characterizing a binding pocket or peptide sequence in terms of an ensemble of favorable binding positions for different chemical groups and then searching for orientations of the candidate molecules that cause maximum spatial coincidence of individual candidate chemical groups with members of the ensemble. By using the information generated by the algorithms, peptides and/or small molecules can be synthesized that are spatially and chemically optimized to interact with Sprouty.

The compounds of the present invention can also be peptidomimetic compounds that can be at least partially unnatural. The peptidomimetic compound can be a small molecule mimic of a portion of any desirable amino acid sequence. The compound can have increased stability, efficacy, potency and bioavailability by virtue of the mimic. Further, the compound can have decreased toxicity. The peptidomimetic compound can have enhanced mucosal intestinal permeability. The compound can be synthetically prepared. The compound of the present invention can include L-,D- or unnatural amino acids, alpha, alpha-disubstituted amino acids, N-alkyl amino acids, lactic acid (an isoelectronic analog of alanine). The peptide backbone of the compound can have at least one bond replaced with PSI-[CH.dbd.CH] (Kempf et al., 1991). The compound can further include trifluorotyrosine, p-Cl-phenylalanine, p-Br-phenylalanine, poly-L-propargylglycine, poly-D,L-allyl glycine, or poly-L-allyl glycine.

One example of the present invention is a peptidomimetic compound wherein the compound has a bond, a peptide backbone or an amino acid component replaced with a suitable mimic. Examples of unnatural amino acids which can be suitable amino acid mimics include, but are not limited to, β-alanine, L-α-amino butyric acid, L-γ-amino butyric acid, L-α-amino isobutyric acid, L-ε-amino caproic acid, 7-amino heptanoic acid, L-aspartic acid, L-glutamic acid, cysteine (acetamindomethyl), N-ε-Boc-N-α-CBZ-L-lysine, N-ε-Boc-N-α-Fmoc-L-lysine, L-methionine sulfone, L-norleucine, L-norvaline, N-α-Boc-N-δ-CBZ-L-ornithine, N-δ-Boc-N-α-CBZ-L-omithine, Boc-p-nitro-L-phenylalanine, Boc-hydroxyproline, Boc-L-thioproline. (Blondelle, et al. 1994; Pinilla, et al. 1995).

Sometimes, the Sprouty inhibitor can be a small molecule that binds, interacts, or associates with a Sprouty protein or RNA. Such a small molecule can be an organic molecule that is capable of penetrating the lipid bilayer of a cell to interact with Sprouty. Small include, but are not limited to, toxins, chelating agents, metals, and metalloid compounds. Small molecules can be attached or conjugated to a targeting agent so as to specifically guide the small molecule to a particular cell.

Chemical Libraries

Peptides can be identified using recombinant or chemical library approaches. Libraries of natural peptides in the form of bacterial, fungal, plant and animal extracts are available or can readily produced. Natural and synthetically produced libraries and peptides can be readily modified through conventional chemical, physical, and biochemical means.

The methods of the invention utilize this library technology to identify peptides, which bind to Sprouty amino acid sequences. One advantage of using libraries for antagonist identification is the facile manipulation of millions of different putative candidates of small size in small reaction volumes (i.e., in synthesis and screening reactions). Another advantage of libraries is the ability to synthesize inhibitors, which might not otherwise be attainable using naturally occurring sources, particularly in the case of non-peptide moieties.

Synthetic DNA and RNA libraries are also commonly used in the art. For instance, Ellington and Szostak describe theuse of random polynucleotide libraries to identify novel ligands (Ellington and Szostak (1990) *Nature* 346:818-822). Modifications of peptide inhibitors can be made at the level of the nucleic acid sequence. Amino acid substitutions can be made by PCR-directed mutation, site-directed mutagenesis according to the method of Kunkel ((1985) *Proc. Nat. Acad. Sci. U.S.A.* 82:488-492), or by chemical synthesis of a nucleic acid molecule encoding a peptide inhibitor of Sprouty.

Methods for preparing libraries of peptides are well known in the art and many libraries are commercially available (e.g., Mimotopes, Raleigh N.C.). Degenerate peptide libraries can be readily prepared in solution, in immobilized form as bacterial flagella peptide display libraries or as phage display libraries. Peptide ligands can be selected from combinatorial libraries of peptides containing at least one amino acid. Libraries can be synthesized of peptoids and non-peptide synthetic moieties. Such libraries can further be synthesized which contain non-peptide synthetic moieties, which are less subject to enzymatic degradation compared to their naturally-occurring counterparts. Libraries are also meant to include, but are not limited to, peptide-on-plasmid libraries, polysome libraries, aptamer libraries, synthetic peptide libraries, synthetic small molecule libraries and chemical libraries. The libraries can also comprise cyclic carbon or heterocyclic structure and/or aromatic or polyaromatic structures substituted with one or more of the above-identified functional groups.

Furthermore, other test compounds used in the methods described herein can be obtained from using any of the approaches in combinatorial library methods known in the art, including: biological libraries; peptoid libraries (libraries of molecules having the functionalities of peptides, but with a novel, non-peptide backbone which are resistant to enzymatic degradation but which nevertheless remain bioactive (see, e.g., Zuckermann et al. (1994) *J. Med. Chem.* 37:2678-85); spatially addressable parallel solid phase or solution phase libraries; synthetic library methods requiring deconvolution; the 'one-bead one-compound' library method; and synthetic library methods using affinity chromatography selection. The biological library and peptoid library approaches are limited to peptide libraries, while the other four approaches are applicable to peptide, non-peptide oligomer or small molecule libraries of compounds (Lam (1997) *Anticancer Drug Des.* 12:145).

Nonlimiting examples of methods for the synthesis of molecular libraries can be found in the art (see, e.g., DeWitt et al. (1993) *Proc. Natl. Acad. Sci. U.S.A.* 90:6909; Erb et al. (1994) *Proc. Natl. Acad. Sci. U.S.A.* 91:11422; Zuckermann et al. (1994) *J. Med. Chem.* 37:2678; Cho et al. (1993) *Science*, 261:1303; Carrell et al. (1994) *Angew. Chem. Int. Ed.*

*Engl.,* 33:2059; Carell et al. (1994) *Angew. Chem. Int. Ed. Engl.* 33:2061; and in Gallop et al. (1994) *J. Med. Chem.* 37:1233).

Compounds that can be used as test compounds are also available from commercial sources (e.g., Leadgenix; Taejon, Korea and Mimotopes; San Diego, Calif.).

Libraries of compounds can be presented in solution (e.g., Houghten (1992) *Biotechn.* 13:412-421), or on beads (Lam (1991) *Nature* 354:82-84), chips (Fodor (1993) *Nature* 364:555-556), bacteria (U.S. Pat. No. 5,223,409), spores (U.S. Pat. No. 5,223,409), plasmids (Cull et al. (1992) *Proc. Natl. Acad. Sci. U.S.A.* 89:1865-1869) or on phage (Scott and Smith (1990) *Science* 249:386-390; Devlin (1990) *Science* 249:404-406; Cwirla et al. (1990) *Proc. Natl. Acad. Sci. U.S.A.* 87:6378-6382; Felici (1991) *J. Mol. Biol.* 222:301-310).

Diagnosis of Malignancies Related to Ras Oncogenic Activity

Certain malignancies such as those related to Ras oncogenic activity are susceptible to treatment by compounds that decrease Sprouty expression or activity. Such malignancies can be identified by the activation of Ras/Map kinase pathways associated with malignancy, or with the overexpression of a Sprouty, e.g., Sprouty2. Non-limiting examples of malignancies that are associated with overexpression or Sprouty are fibrosarcomas, melanomas, thyroid tumors, breast tumors, lung tumors, and pancreatic tumors. According to aspects of the invention, malignancies that can be treated, for example, using a compound that decreases expression of Sprouty can be identified by obtaining a sample of a malignancy suspected of having Ras oncogenic activity, testing the sample for expression or activity of a Sprouty protein, and determining whether the expression or activity of the Sprouty protein is increased compared to a reference, e.g., when a nucleic acid or protein is overexpressed. In general, the reference is determined by testing a sample comprising cells or isolated cell components derived from the same cell or tissue type as the malignant cells. In some cases, a reference is predetermined, e.g., a reference can be a predetermined value that is determined to be a threshold amount of expression or activity of a specific nucleic acid or protein that is used to evaluate a sample for overexpression of the specific nucleic acid or protein.

Predictive Medicine

The present invention also pertains to the field of predictive medicine in which diagnostic assays, prognostic assays, and monitoring of clinical trials are used for prognostic (predictive) purposes to thereby treat a subject having or at risk for having a disease characterized by undesirable expression of a Sprouty protein (e.g., a Sprouty2). Examples of such diseases are cancers characterized by expression of a Ras oncogene.

The method includes one or more of the following. The method can include detecting, in a tissue of a subject, the presence or absence of a mutation which affects the expression of the Sprouty gene, or detecting the presence or absence of a mutation in a region which controls the expression of the gene, e.g., a mutation in the 5' control region. In another aspect, the invention includes detecting, in a tissue of the subject, the presence or absence of a mutation which alters the structure of the Sprouty gene; detecting, in a tissue of the subject, the misexpression of the Sprouty gene, at the mRNA level, e.g., detecting a non-wild type level of a mRNA, in general, an undesirable increase in Sprouty mRNA expression; or detecting, in a tissue of the subject, the misexpression of the gene, at the protein level, e.g., detecting a non-wild type level of a Sprouty polypeptide, in general, an undesirable increase in Sprouty protein expression.

Sometimes the method of the invention includes contacting a sample from the subject with an antibody to the Sprouty protein or a nucleic acid that specifically hybridizes with the gene.

Diagnostic and Prognostic Assays

According to aspects of the invention, the presence or level of a Sprouty protein or nucleic acid in a biological sample (e.g., a sample from a subject having or at risk for a Ras-related cancer) can be evaluated by obtaining a biological sample from a subject and contacting the biological sample with a compound or an agent capable of detecting Sprouty protein or nucleic acid (e.g., mRNA) that encodes Sprouty protein such that the presence of Sprouty protein or nucleic acid is detected in the biological sample. The term "biological sample" includes tissues, cells, and biological fluids isolated from a subject, as well as tissues, cells and fluids present within a subject. In some cases, the biological sample is serum or plasma. The level of expression of the Sprouty gene can be measured using any method known in the art, including, but not limited to; measuring the mRNA encoded by a Sprouty gene; measuring the amount of protein encoded by a Sprouty gene; or measuring the activity of a Sprouty protein.

The Sprouty mRNA in a biological can be used in hybridization or amplification assays that include, but are not limited to, Southern or Northern analyses, polymerase chain reaction (PCR) analyses, and probe arrays. One diagnostic method for the detection of mRNA levels involves contacting the isolated mRNA with a nucleic acid molecule (probe) that can hybridize to the mRNA encoded by the gene being detected. The nucleic acid probe can be, for example, a full-length Sprouty nucleic acid or a portion thereof, such as an oligonucleotide of at least 7, 15, 30, 50, 100, 250 or 500 nucleotides in length and sufficient to specifically hybridize under stringent conditions to Sprouty mRNA or genomic DNA. Other suitable probes can be designed and made using methods known in the art. Probes can be designed using known Sprouty sequences, e.g., Genbank accession nos. O43609, O43597, and NP 005831.

In one format according to the invention, Sprouty mRNA (or cDNA) is immobilized on a surface and contacted with the a probe, for example by running the isolated mRNA on an agarose gel and transferring the mRNA from the gel to a membrane, such as nitrocellulose. In an alternative format, the probes are immobilized on a surface and the mRNA (or cDNA) is contacted with the probes, for example, in a two-dimensional gene chip array. A skilled artisan can adapt known mRNA detection methods for use in detecting the level of mRNA encoded by a Sprouty gene. In some cases, expression of a specific Sprouty gene is detected. In other assays, a probe that is specific for Sprouty mRNAs, but that can detect more than one Sprouty mRNA is used.

The level of mRNA in a sample that is encoded by one of Sprouty can be evaluated with nucleic acid amplification, e.g., by rtPCR (U.S. Pat. No. 4,683,202), ligase chain reaction (Barany (1991) *Proc. Natl. Acad. Sci. U.S.A.* 88:189-193), self sustained sequence replication (Guatelli et al. (1990) *Proc. Natl. Acad. Sci. U.S.A.* 87:1874-1878), transcriptional amplification system (Kwoh et al. (1989) *Proc. Natl. Acad. Sci. U.S.A.* 86:1173-1177), Q-Beta Replicase (Lizardi et al. (1988) *Bio/Technol.* 6:1197), rolling circle replication (U.S. Pat. No. 5,854,033) or any other nucleic acid amplification method, followed by the detection of the amplified molecules using techniques known in the art. As used herein, amplification primers are defined as being a pair of nucleic acid molecules that can anneal to 5' or 3' regions of a gene (plus and minus strands, respectively, or vice-versa) and contain a short region in between. In general, amplification primers are from about 10 to 30 nucleotides in length and generally flank a region from about 50 to 200 nucleotides in length. Under appropriate conditions and with appropriate reagents, such primers permit the amplification of a nucleic acid molecule comprising the nucleotide sequence flanked by the primers.

For in situ methods, a cell or tissue sample can be prepared/processed and immobilized on a support, typically a glass slide, and then contacted with a probe that can hybridize to mRNA that encodes the Sprouty gene, washed and analyzed for specific hybridization to Sprouty mRNA.

In addition, the method can include contacting a control sample with a compound or agent capable of detecting Sprouty mRNA, or genomic DNA, and comparing the presence of Sprouty mRNA or genomic DNA in the control sample with the presence of Sprouty mRNA or genomic DNA in the test sample.

A variety of methods known in the art can be used to determine the level of protein encoded by Sprouty. Such methods include those in which an absolute amount of Sprouty is determined (e.g., an amount of Sprouty per mg protein in a sample), and those in which a relative amount of Sprouty is determined (e.g., compared to a reference). In general, these methods include contacting an agent that selectively binds to the protein, such as an antibody, with a test sample to evaluate the level of protein in the sample. In some cases, the antibody bears a detectable label. Antibodies can be polyclonal, or monoclonal. An intact antibody, or a fragment thereof (e.g., Fab, $F(ab')_2$, or FV) can be used. The term "labeled", with regard to the probe or antibody, is intended to encompass direct labeling of the probe or antibody by coupling (i.e., physically linking) a detectable substance to the probe or antibody, as well as indirect labeling of the probe or antibody by reactivity with a detectable substance. Examples of detectable substances are provided herein and are known in the art.

The detection methods can be used to detect Sprouty protein in a biological sample in vitro as well as in vivo. Useful, non-limiting in vitro techniques for detection of Sprouty protein include enzyme linked immunosorbent assays (ELISAs), immunoprecipitations, immunofluorescence, enzyme immunoassay (EIA), radioimmunoassay (RIA), and Western blot analysis. Useful in vivo techniques for detection of Sprouty protein include, but are not limited to, introducing into a subject a labeled anti-Sprouty antibody. For example, the antibody can be labeled with a radioactive marker whose presence and location in a subject can be detected by standard imaging techniques.

The methods also include contacting a control sample with a compound or agent capable of detecting Sprouty protein, and comparing the presence of Sprouty protein in the control sample with the presence of Sprouty protein in the test sample. In general, a control sample is derived from the same tissue as the test sample and it is known whether the control sample expresses a Ras oncogene or is malignant tissue. In some assay methods of the invention, a reference level of Sprouty expression or activity is established and Sprouty expression or activity is compared to the reference, which can be from a control or established by prior investigation, e.g., a standard.

Aspects of the invention also include kits for detecting the presence of Sprouty in a biological sample. For example, the kit can include a compound or agent capable of detecting Sprouty protein or mRNA in a biological sample, and a standard. The compound or agent can be packaged in a suitable container. The kit can further comprise instructions for using the kit to detect Sprouty protein or nucleic acid, and can include instructions for use.

For antibody-based kits, an embodiment of the kit includes a first antibody (e.g., attached to a solid support) which binds to a polypeptide corresponding to a marker of the invention; and, optionally, a second, different antibody which binds to either the polypeptide or the first antibody and is conjugated to a detectable agent.

For oligonucleotide-based kits of the invention, the kit includes an oligonucleotide, e.g., a detectably labeled oligonucleotide that hybridizes to a nucleic acid sequence encoding a polypeptide corresponding to a marker of the invention; and/or a pair of primers useful for amplifying a nucleic acid molecule corresponding to a marker of the invention. The kit can also includes a buffering agent, a preservative, or a protein stabilizing agent. Additional embodiments of the kit can also include components necessary for detecting the detectable agent (e.g., an enzyme or a substrate). The kit can also contain a control sample or a series of control samples that can be assayed and compared to the test sample contained. Each component of the kit can be enclosed within an individual container and all of the various containers can be within a single package, along with instructions for interpreting the results of the assays performed using the kit.

The diagnostic methods described herein are useful for identifying subjects having, or at risk of developing, a disease or disorder associated with misexpressed or aberrant or undesirable Sprouty expression or activity.

In one method, a disease or disorder associated with aberrant or unwanted Sprouty expression or activity is identified. A test sample is obtained from a subject and Sprouty protein or nucleic acid (e.g., mRNA or genomic DNA) expression is evaluated. An increase in the level, e.g., an increase in Sprouty protein or nucleic acid is diagnostic for the subject having or being at risk of developing a disease associated with aberrant or unwanted Sprouty expression or activity, e.g., a Ras-associated cancer. As used herein, a "test sample" refers to a biological sample obtained from a subject of interest, including a biological fluid (e.g., serum), cell sample, or tissue.

The prognostic assays described herein are useful to determine whether a subject can be administered an agent (e.g., an agonist, antagonist, peptidomimetic, protein, peptide, nucleic acid, small molecule, or other drug candidate) to treat a disease or disorder associated with aberrant or unwanted Sprouty expression or activity. For example, such methods can be used to determine whether a subject can be effectively treated with an agent for a Ras-associated cancer including certain fibrosarcomas and pancreatic cancers.

Pharmaceutical Compositions

Compounds that decrease Sprouty expression of activity, e.g., compounds that decrease Sprouty expression or activity in a cell transformed by expression of a Ras oncogene, are incorporated into pharmaceutical compositions according to the invention. Such compositions typically include the compound and a pharmaceutically acceptable carrier. As used herein the language "pharmaceutically acceptable carrier" includes solvents, dispersion media, coatings, antibacterial and antifungal agents, isotonic and absorption delaying agents, and the like, compatible with pharmaceutical administration. Supplementary active compounds can also be incorporated into the compositions.

A pharmaceutical composition is formulated to be compatible with its intended route of administration. Nonlimiting examples of routes of administration include parenteral, e.g., intravenous, intradermal, subcutaneous, oral (e.g., inhalation), transdermal (topical), transmucosal, vaginal and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringability exists. It should be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyetheylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. It may be desirable to include isotonic agents, for example, sugars, polyalcohols such as manitol, sorbitol, or sodium chloride in the composition. Prolonged absorption of the injectable compositions can be accomplished by including in the composition an agent that delays absorption, for example, aluminum monostearate and gelatin. (See, e.g., *Remingtons*, The Science and Practice of Pharmacy ($20^{th}$ ed.) (2000), Gennaro et al. eds.)

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, the methods of preparation include, without limitation, vacuum drying and freeze-drying which yields a powder of the active ingredient plus any additional desired ingredient from a previously sterile-filtered solution thereof.

Oral compositions generally include an inert diluent or an edible carrier. For the purpose of oral therapeutic administration, the active compound can be incorporated with excipients and used in the form of tablets, troches, or capsules, e.g., gelatin capsules. Oral compositions can also be prepared using a fluid carrier for use as a mouthwash. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser that contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, but are not limited to, for example, for transmucosal administration, detergents, bile salts, and fusidic acid derivatives. Transmucosal administration can be accomplished through the use of nasal sprays or suppositories. For transdermal administration, the active compounds are formulated into, e.g., ointments, salves, gels, or creams as generally known in the art.

The compositions according to the invention can also be prepared in the form of suppositories (e.g., with conventional suppository bases such as cocoa butter and other glycerides) or retention enemas for rectal delivery.

One therapeutic composition of the invention is prepared with a carrier that protects the Sprouty-related compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations are be apparent to those skilled in the art. The materials can also be obtained commercially (e.g., from Alza Corp., Mountain View, Calif.). Liposomal suspensions (including liposomes targeted to infected cells with monoclonal antibodies to viral antigens) can also be used as pharmaceutically acceptable carriers. These can be prepared according to methods known to those skilled in the art, e.g., as described in U.S. Pat. No. 4,522,811.

It may be advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier.

Toxicity and therapeutic efficacy of such compounds can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. While compounds that exhibit toxic side effects can be used, care should be taken to design a delivery system that targets such compounds to the site of affected tissue in order to minimize potential damage to uninfected cells and, thereby, reduce side effects.

The data obtained from the cell culture assays and animal studies can be used in formulating a range of dosage for use in humans. The dosage of such compounds lies generally within a range of circulating concentrations that include the $ED_{50}$ with little or no toxicity. The dosage can vary within this range depending upon the dosage form employed and the route of administration utilized. For any compound used in the method of the invention, the therapeutically effective dose can be estimated initially from cell culture assays. A dose can be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma can be measured, for example, by high performance liquid chromatography. Information for preparing and testing such compositions are known in the art (see, e.g., Gennaro, ed., *Remington: The Science and Practice of Pharmacy*, $20^{th}$ edition, Lippincott Williams & Wilkins, (2000)).

As defined herein, a therapeutically effective amount of protein, polypeptide, or peptidomimetic (i.e., an effective dosage) ranges from about 0.001 mg/kg to 30 mg/kg body weight, e.g., about 0.01 mg/kg to 25 mg/kg, about 0.1 mg/kg to 20 mg/kg, about 1 mg/kg to 10 mg/kg, about 2 mg/kg to 9 mg/kg, about 3 mg/kg to 8 mg/kg, about 4 mg/kg to 7 mg/kg, or about 5 mg/kg to 6 mg/kg body weight. The protein or polypeptide can be administered one time per week for between about 1 week to about 10 weeks, e.g., between about 2 weeks to 8 weeks, between about 3 weeks to 7 weeks, for about 4 weeks, for about 5 weeks, or for about 6 weeks. The skilled artisan will appreciate that certain factors can influence the dosage and timing required to effectively treat a subject, including but not limited to the severity of the disease or disorder, previous treatments, the general health and/or age of the subject, and other diseases present. Moreover, treatment of a subject with a therapeutically effective amount of a protein, polypeptide, peptidomimetic, or antibody can include a single treatment or can include a series of treatments.

For antibodies, the dosage is 0.1 mg/kg of body weight (generally 10 mg/kg to 20 mg/kg). If the antibody is to act in the brain, a dosage of 50 mg/kg to 100 mg/kg is usually appropriate. Generally, partially human antibodies and fully human antibodies have a longer half-life within the human body than other antibodies. Accordingly, lower dosages and less frequent administration are often possible. Modifications such as lipidation can be used to stabilize antibodies and to enhance uptake and tissue penetration (e.g., into the brain). Cruikshank et al. (1997) *J. Acquired Imm. Def. Syndr. Hum. Retrovirol.* 14:193 describes a method for lipidation of antibodies.

Aspects of the present invention encompass agents that decrease expression or activity. An agent can, for example, be a small molecule. Such small molecules can include, but are not limited to, peptides, peptidomimetics (e.g., peptoids), amino acids, amino acid analogs, polynucleotides, polynucleotide analogs, nucleotides, nucleotide analogs, organic or inorganic compounds (i.e., including heteroorganic and organometallic compounds) having a molecular weight less than about 10,000 grams per mole, organic or inorganic compounds having a molecular weight less than about 5,000 grams per mole, organic or inorganic compounds having a molecular weight less than about 1,000 grams per mole, organic or inorganic compounds having a molecular weight less than about 500 grams per mole, and salts, esters, and other pharmaceutically acceptable forms of such compounds.

Exemplary doses include milligram or microgram amounts of the small molecule per kilogram of subject or sample weight (e.g., about 1 µg/kg to about 500 mg/kg, about 100 µg/kg about 5 mg/kg, or about 1 µg/kg to about 50 µg/kg. It is furthermore understood that appropriate doses of a small molecule depend upon the potency of the small molecule with respect to the expression or activity to be decreased. When one or more of these small molecules is to be administered to an animal (e.g., a human) in order to decrease expression or activity of a polypeptide or nucleic acid of the invention, a physician, veterinarian, or researcher can, for example, prescribe a relatively low dose at first, subsequently increasing the dose until an appropriate response is obtained. In addition, it is understood that the specific dose level for any particular animal subject will depend upon a variety of factors including the activity of the specific compound employed, the age, body weight, general health, gender, and diet of the subject, the time of administration, the route of administration, the rate of excretion, any drug combination, and the degree of expression or activity to be decreased.

The nucleic acid molecules of the invention can be inserted into vectors and used as gene therapy vectors. Gene therapy vectors can be delivered to a subject by, for example, intravenous injection, local administration (see, e.g., U.S. Pat. No. 5,328,470) or by stereotactic injection (see, e.g., Chen et al. (1994) *Proc. Natl. Acad. Sci. U.S.A.* 91:3054-3057). The pharmaceutical preparation of the gene therapy vector can include the gene therapy vector in an acceptable diluent, or can comprise a slow release matrix in which the gene delivery vehicle is imbedded. Alternatively, where the complete gene delivery vector can be produced intact from recombinant cells, e.g., retroviral vectors, the pharmaceutical preparation can include one or more cells which produce the gene delivery system.

The pharmaceutical compositions can be included in a container, pack, or dispenser together with instructions for administration.

Methods of Treatment

Aspects of the present invention provide for both prophylactic and therapeutic methods of treating a subject (human or non-human animal) at risk of (or susceptible to) a disease or having a disease associated with aberrant or undesirable Sprouty expression or activity. As used herein, the term "treatment" is defined as the application or administration of a therapeutic agent to a patient, or application or administration of a therapeutic agent to an isolated tissue or cell line from a subject, who has a disease, a symptom of disease or a predisposition toward a disease, with the purpose to cure, heal, alleviate, relieve, alter, remedy, ameliorate, improve or affect the disease, the symptoms of disease or the predisposition toward disease. A therapeutic agent includes, but is not limited to, small organic (non-nucleic acid) molecules, small inorganic molecules, peptides, peptidomimetics, antibodies, and oligonucleotides including ribozymes, siRNA, and antisense oligonucleotides, as described above.

Both prophylactic and therapeutic methods of treatment, such treatments are specifically tailored or modified, based on knowledge obtained from the field of pharmacogenomics. "Pharmacogenomics", as used herein, refers to the application of genomics technologies such as gene sequencing, statistical genetics, and gene expression analysis to drugs in clinical development and on the market. More specifically, the term refers the study of how a patient's genes determine his or her response to a drug (e.g., a patient's "drug response phenotype", or "drug response genotype"). Thus, another aspect of the invention provides methods for tailoring an individual's prophylactic or therapeutic treatment with a Sprouty modulator according to that individual's drug response genotype. Pharmacogenomics allows a clinician or physician to target prophylactic or therapeutic treatments to patients who will most benefit from the treatment and to avoid treatment of patients who will experience toxic drug-related side effects.

In one aspect, a method is provided for preventing in a subject, a disease or condition associated with an aberrant or undesirable Sprouty expression or activity, by administering to the subject an agent that decreases Sprouty expression or at least one Sprouty activity. Subjects at risk for a disease that is caused or contributed to by aberrant or undesirable Sprouty expression or activity can be identified by, for example, any or a combination of diagnostic or prognostic assays as described herein. Administration of a prophylactic agent occurs prior to the manifestation of symptoms characteristic of the Sprouty aberrance, such that a disease is prevented or, alternatively, delayed in its progression.

Ras-oncogene associated disorders, fibrosarcomas, melanomas, and pancreatic tumors that are characterized by an abnormal level (e.g., an elevated level) of a Sprouty protein, or by the presence of a Sprouty protein exhibiting abnormal activity (e.g., elevated activity compared to normal activity) can be treated using compounds identified using methods described herein. As such, the reduction in the level and/or activity of such gene products would bring about the amelioration of disorder symptoms.

Sprouty molecules (e.g., Sprouty2) can act as novel diagnostic targets and therapeutic agents for controlling one or more of cellular proliferative diseases, e.g., proliferative diseases associated with activation of a Ras oncogene.

Examples of cellular proliferative diseases include cancer, e.g., carcinoma, sarcoma, metastatic disorders or hematopoietic neoplastic disorders, e.g., leukemias. A metastatic tumor can arise from a multitude of primary tumor types, including but not limited to those of prostate, colon, lung, breast, and liver origin.

As used herein, the terms "cancer", "hyperproliferative" and "neoplastic" refer to cells having the capacity for autonomous growth, i.e., an abnormal state or condition characterized by rapidly proliferating cell growth. Hyperproliferative and neoplastic disease states can be categorized as pathologic, i.e., characterizing or constituting a disease state, or can be categorized as non-pathologic, i.e., a deviation from normal but not associated with a disease state. The term is meant to include all types of cancerous growths or oncogenic processes, metastatic tissues or malignantly transformed cells, tissues, or organs, irrespective of histopathologic type or stage of invasiveness. "Pathologic hyperproliferative" cells occur in disease states characterized by malignant tumor growth. Examples of non-pathologic hyperproliferative cells include those that proliferate in association with wound repair.

The terms "cancer" or "neoplasms" include malignancies of the various organ systems, such as affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus.

The term "carcinoma" is art recognized and refers to malignancies of epithelial or endocrine tissues including, but not limited to, respiratory system carcinomas, gastrointestinal system carcinomas, genitourinary system carcinomas, testicular carcinomas, breast carcinomas, prostatic carcinomas, endocrine system carcinomas, and melanomas. Exemplary nonlimiting carcinomas include those forming from tissue of the cervix, lung, prostate, breast, head and neck, colon and ovary. The term also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures.

The term "sarcoma" is art recognized and refers to malignant tumors of mesenchymal derivation.

As described above, successful treatment of Sprouty disorders can be brought about by techniques that serve to inhibit the expression or activity of Sprouty proteins. For example, compounds that prove to exhibit negative modulatory activity (e.g., an agent identified using an assays described above) can be used in accordance with the invention to prevent and/or ameliorate symptoms of Sprouty disorders. Such molecules can include, but are not limited to peptides, phosphopeptides, small organic or inorganic molecules, or antibodies (including, for example, polyclonal, monoclonal, humanized, anti-idiotypic, chimeric or single chain antibodies, and Fab, $F(ab')_2$, Fab, and Fv expression library fragments, scFV molecules, and epitope-binding fragments thereof).

Further, antisense, siRNA, and ribozyme molecules that inhibit expression of the target gene can also be used in accordance with the invention to reduce the level of target gene expression, thus effectively reducing the level of target gene activity. Still further, triple helix molecules can be utilized in reducing the level of target gene activity. Antisense, ribozyme and triple helix molecules are discussed above.

In particular, siRNA or other oligonucleotide can also be introduced into the cell by transfection with an heterologous target gene using carrier compositions such as liposomes, which are known in the art (e.g., Lipofectamine™ 2000 (Invitrogen, Carlsbad, Calif.) as described by the manufacturer for adherent cell lines). Transfection of dsRNA oligonucleotides for targeting endogenous genes can be carried out, for example, using Oligofectamine™ (Invitrogen, Carlsbad, Calif.). The effectiveness of the oligonucleotide can be assessed by any of a number of assays following introduction of the oligonucleotide into a cell. These assays include, but are not limited to, Western blot analysis using antibodies that recognize the targeted gene product following sufficient time for turnover of the endogenous pool after new protein synthesis is repressed, and Northern blot analysis to determine the level of existing target mRNA.

Antibodies can be generated that are both specific for Sprouty protein and that reduce Sprouty protein activity. Such antibodies are administered in instances whereby negative modulatory techniques are appropriate for the treatment of Sprouty disorders.

The compounds identified as described herein that inhibit Sprouty gene expression, synthesis, and/or activity can be administered to a subject at therapeutically effective doses to prevent, treat or ameliorate Sprouty disorders. A therapeutically effective dose refers to that amount of the compound sufficient to result in amelioration of symptoms of the disorders. Toxicity and therapeutic efficacy of such compounds can be determined by standard pharmaceutical procedures as described above.

Another example of determination of effective dose for an individual is the ability to directly assay levels of "free" and "bound" compound in the serum of the test subject. Such assays can utilize antibody mimics and/or "biosensors" that have been created through molecular imprinting techniques. The compound which is able to decrease Sprouty activity is used as a template, or "imprinting molecule", to spatially organize polymerizable monomers prior to their polymerization with catalytic reagents. The subsequent removal of the imprinted molecule leaves a polymer matrix that contains a repeated "negative image" of the compound and is able to selectively rebind the molecule under biological assay conditions (see, e.g., Ansell et al. (1996) *Curr. Opin. Biotechnol.* 7:89-94 and Shea (1994) *Trends Polymer Sci.* 2:166-173). Such "imprinted" affinity matrices are amenable to ligand-binding assays, whereby the immobilized monoclonal antibody component is replaced by an appropriately imprinted matrix (see, e.g., Vlatakis et al. (1993) *Nature* 361:645-647). Through the use of isotope labeling, the "free" concentration of compound that decreases the expression or activity of Sprouty can be readily monitored and used in calculations of $IC_{50}$.

Such "imprinted" affinity matrixes can also be designed to include fluorescent groups whose photon-emitting properties measurably change upon local and selective binding of target compound. These changes can be readily assayed in real time using appropriate fiber optic devices, in turn allowing the dose in a test subject to be quickly optimized based on its individual $IC_{50}$ (see, e.g., Kriz et al. (1995) *Anal. Chem.* 67:2142-2144).

Another aspect of the invention pertains to methods of modulating Sprouty expression or activity for therapeutic purposes. Accordingly, in an exemplary embodiment, the modulatory method of the invention involves contacting a cell with a compound that decreases one or more of the activities of Sprouty protein activity associated with the cell. A compound that decreases Sprouty protein activity can be an compound as described herein.

In general, the agent inhibits one or more Sprouty activities. Examples of such inhibitory agents include antisense Sprouty nucleic acid molecules, anti-Sprouty antibodies, and Sprouty inhibitors (e.g., peptides, peptidomimetics, small organic (non-nucleic acid) molecules or small inorganic molecules). These modulatory methods can be performed in vitro (e.g., by culturing the cell with the agent) or, alternatively, in vivo (e.g., by administering the agent to a subject). As such, aspects of the present invention provide methods of treating an individual afflicted with a disease or disorder characterized by aberrant or unwanted expression or activity of a Sprouty protein or nucleic acid molecule. In one embodiment, the method involves administering an agent (e.g., an agent identified by a screening assay described herein), or combination of agents that decreases (e.g., down-regulates) Sprouty expression or activity.

Compounds that decrease the expression or activity can be used for the preparation of a medicament for use in any of the methods of treatment described herein.

Coadministration with EGFR-Targeted Chemotherapeutics

The invention includes methods, and associated pharmaceutical formulations, of treating cancer by administering a second chemotherapeutic agent in combination with the Sprouty2 antagonists of the invention. As used here, a "chemotherapeutic agent" is a chemical compound useful in the treatment of cancer. Nonlimiting examples of chemotherapeutic agents include alkylating agents such as thiotepa and cyclosphosphamide (CYTOXAN™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethiylenethiophosphoramide and trimethylolomelamine; acetogenins (especially bullatacin and bullatacinone); delta-9-tetrahydrocannabinol (dronabinol, MARINOL™); beta-lapachone; lapachol; colchicines; betulinic acid; a camptothecin (including the synthetic analogue topotecan (HYCAMTIN™), CPT-11 (irinotecan, CAMPTOSAR™), acetylcamptothecin, scopolectin, and 9-aminocamptothecin); bryostatin; callystatin; CC-1065 (including its adozelesin, carzelesin and bizelesin synthetic analogues); podophyllotoxin; podophyllinic acid; teniposide; cryptophycins (particularly cryptophycin 1 and cryptophycin 8); dolastatin; duocarmycin (including the synthetic analogues, KW-2189 and CB1-TM1); eleutherobin; pancratistatin; a sarcodictyin; spongistatin; nitrogen mustards such as chlorambucil, chlornaphazine, cholophosphamide, estramustine, ifosfamide, mechlorethainine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, and ranimnustine; antibiotics such as the enediyne antibiotics (e.g., calicheamicin, especially calicheamicin gamma1I and calicheamicin omega1I (see, e.g., Agnew (1994) *Chem Intl. Ed. Engl.* 33:183-186); dynemicin, including dynemicin A; an esperamicin; as well as neocarzinostatin chromophore and related chromoprotein enediyne antiobiotic chromophores), aclacinomysins, actinomycin, authramycin, azaserine, bleomycins, cactinomycin, carabicin, carminomycin, carzinophilin, chromomycinis, dactinomycin, daunorubicin, detorubicin, 6-diazo-5-oxo-L-norleucine, doxorubicin (including ADRIAMYCIN™, morpholino-doxorubicin, cyanomorpholino-doxorubicin, 2-pyrrolino-doxorubicin, doxorubicin HCl liposome injection (DOXIL™), liposomal doxorubicin TLC D-99 (MYOCET™), peglylated liposomal doxorubicin (CAELYX™), and deoxydoxorubicin), epirubicin, esorubicin, idarubicin, marcellomycin, mitomycins such as mitomycin C, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate, gemcitabine (GEMZAR™), tegafur (UFIORAL™), capecitabine (XELODA™), an epothilone, and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; anti-adrenals such as aminoglutethimide, mitotane, trilostane; folic acid replenisher such as frolinic acid; aceglatone; aldophosphamide glycoside; aminolevulinic acid; eniluracil; amsacrine; bestrabucil; bisantrene; edatraxate; defofamine; demecolcine; diaziquone; elformnithine; elliptinium acetate; etoglucid; gallium nitrate; hydroxyurea; lentinan; lonidainine; maytansinoids such as maytansine and ansamitocins; mitoguazone; mitoxantrone; mopidanmol; nitraerine; pentostatin; phenamet; pirarubicin; losoxantrone; 2-ethylhydrazide; procarbazine; PSK.RTM. polysaccharide complex (JHS Natural Products, Eugene, Oreg.); razoxane; rhizoxin; sizofiran; spirogermanium; tenuazonic acid; triaziquone; 2,2',2"-trichlorotriethyla-mine; trichothecenes (especially T-2 toxin, verracurin A, roridin A and anguidine); urethan; dacarbazine; mannomustine; mitobronitol; mitolactol; pipobroman; gacytosine; arabinoside ("Ara-C"); thiotepa; taxoid, e.g., paclitaxel (TAXOL™), albumin-engineered nanoparticle formulation of paclitaxel (ABRAXANE™), and docetaxel (TAXOTERE™); chloranbucil; 6-thioguanine; mercaptopurine; methotrexate; platinum agents such as cisplatin, oxaliplatin, and carboplatin; vincas, which prevent tubulin polymerization from forming microtubules, including vinblastine (VELBAN™), vincristine (ONCOVIN™), vindesine (ELDISINE™, FILDESIN™), and vinorelbine (NAVELBINE™); etoposide (VP-16); ifosfamide; mitoxantrone; leucovovin; novantrone; edatrexate; daunomycin; aminopterin; ibandronate; topoisomerase inhibitor RFS 2000; difluorometlhylornithine (DMFO); retinoids such as retinoic acid, including bexarotene (TARGRETIN™); bisphosphonates such as clodronate (for example, BONEFOS™ or OSTAC™, etidronate (DIDROCAL™), NE-58095, zoledronic acid/zoledronate (ZOMETA™), alendronate (FOSAMAX™), pamidronate (AREDIA™), tiludronate (SKELID™), or risedronate (ACTONEL™); troxacitabine (a 1,3-dioxolane nucleoside cytosine analog); antisense oligonucleotides, particularly those that inhibit expression of genes in signaling pathways implicated in aberrant cell proliferation, such as, for example, PKC-alpha, Raf, H-Ras, and epidermal growth factor receptor (EGF-R); vaccines such as THERATOPE™ vaccine and gene therapy vaccines, for example, ALLOVECTIN™ vaccine, LEUVECTIN™ vaccine, and VAXID.RTM. vaccine; topoisomerase 1 inhibitor (e.g., LURTOTECAN.RTM.); rmRH (e.g., ABARELIX™); BAY439006 (sorafenib; Bayer); SU-11248 (Pfizer); perifosine, COX-2 inhibitor (e.g. celecoxib or etoricoxib), proteosome inhibitor (e.g., PS341); bortezomib (VELCADE™); CC1-779; tipifarnib (R11577); orafenib, ABT510; Bcl-2 inhibitor such as oblimersen sodium (GENASENSE™); pixantrone; EGFR inhibitors (see definition below); tyrosine kinase inhibitors (see definition below); and pharmaceutically acceptable salts, acids or derivatives of any of the above; as well as combinations of two or more of the above such as CHOP, an abbreviation for a combined therapy of cyclophosphamide, doxorubicin, vincristine, and prednisolone, and FOLFOX, an abbreviation for a treatment regimen with oxaliplatin (ELOXATIN™) combined with 5-FU and leucovovin.

Useful chemotherapeutic agents for coadministration of a Sprouty2 antagonist of the invention are the EGFR-targeting chemotherapeutic agents, including, but not limited to, gefitinib (Iressa™ 4-(3'-Chloro-4'-fluoroanilino)-7-methoxy-6-(3-morpholinopropoxy)quinazoline (AstraZeneca, Wilmington, Del.);erlotinib (Tarceva™ Genentech/OSI Pharmaceuticals, SanFrancisco, Calif.); cetuximab (Erbitux™; a chimerized 225 (C225 or Cetuximab)) and matuzumab (a humanized EGFR antibody directed against EGFR that competes with both EGF and TGF-alpha for EGFR binding (EMD/Merck, Whitehouse Station, N.J.). As used herein, the term "EGFR-targeted drug" refers to a therapeutic agent that binds to EGFR and, optionally, inhibits EGFR activation. Erlotinib is a human EGFR type 1 (HER1/EGFR) tyrosine kinase inhibitor. An effective therapeutic dose of erlontinib is 150 mg/daily. Gefitinib (Iressa™) is a small molecule EGFR-selective inhibitor of tyrosine kinase activity that blocks EGF autophosphorylation and activation. An effective therapeutic dose of gefitinib is 250 mg/day. Cetuximab (Erbitux™) is a chimeric human-mouse monoclonal immunoglobin IgG1 antibody that blocks ligand binding and functional activation of the EGFR. Matuzumab (also known as EMD 72000) is a humanized monoclonal antibody specific for EGFR. As with the chimeric antibody cetuximab and the fully human panitumumab, matuzumab binds to the extracellular domain of the EGFR (Thomas et al. (2004) Cancer Treat Rev 30: 255-68). Effective doses of matuzumab are from 100 to 1,000 mg/week, administered intravenously.

Other examples of EGFR-targeted chemotherapeutic agents include other antibodies and small molecules that bind to EGFR. Examples of other antibodies which bind to EGFR include MAb 579 (ATCC CRL HB 8506), MAb 455 (ATCC CRL HB8507), MAb 225 (ATCC CRL 8508), MAb 528 (ATCC CRL 8509) (see, U.S. Pat. No. 4,943,533) and variants thereof, such as reshaped human 225 (H225) (see, WO 96/40210, Imclone Systems Inc.); IMC-11F8, a fully human, EGFR-targeted antibody (Imclone); antibodies that bind type II mutant EGFR (U.S. Pat. No. 5,212,290); humanized and chimeric antibodies that bind EGFR as described in U.S. Pat. No. 5,891,996; and human antibodies that bind EGFR, such as ABX-EGF or Panitumumab (see WO98/50433, Abgenix/Amgen); EMD 55900 (Stragliotto et al. (1996) Eur. J. Cancer 32A:636-640); human EGFR antibody, HuMax-EGFR (GenMab); fully human antibodies known as E1.1, E2.4, E2.5, E6.2, E6.4, E2.11, E6.3 and E7.6.3 and described in U.S. Pat. No. 6,235,883; MDX-447 (Medarex Inc); and mAb 806 or humanized mAb 806 (Johns et al. (2004) J. Biol. Chem. 279(29):30375-30384). The anti-EGFR antibody may be conjugated with a cytotoxic agent, thus generating an immunoconjugate (see, e.g., EP659,439A2, Merck Patent GmbH). Other EGFR antagonists include small molecules such as compounds described in U.S. Pat. Nos. 5,616,582, 5,457,105, 5,475,001, 5,654,307, 5,679,683, 6,084,095, 6,265,410, 6,455,534, 6,521,620, 6,596,726, 6,713,484, 5,770,599, 6,140,332, 5,866,572, 6,399,602, 6,344,459, 6,602,863, 6,391,874, 6,344,455, 5,760,041, 6,002,008, and 5,747,498, as well as the following PCT publications: WO98/14451, WO98/50038, WO99/09016, and WO99/24037. Particular small molecule EGFR antagonists include, but are not limited to, PD 183805 (CI 1033, 2-propenamide, N-[4-[(3-chloro-4-fluorophenyl)amino]-7-[-3-(4-morpholinyl)propoxy]-6-quinazolinyl]-, dihydrochloride, Pfizer Inc.); ZM 105180 ((6-amino-4-(3-methylphenyl-amino)-quinazoline, Zeneca); BIBX-1382 (N-8-(3-chloro-4-fluoro-phenyl)-N-2-(1-methyl-piperidin-4-yl)-pyrimido[5,-4-d]pyrimidine-2,8-diamine, Boehringer Ingelheim); PKI-166 ((R)-4-[4-[(1-phenylethyl)amino]-1H-pyrrolo[2,3-d]pyrimidin-6-yl]-phenol]-; (R)-6-(4-hydroxyphenyl)-4-[(1-phenylethyl) amino]-7H-pyrrolo[2,3-d]pyrimi-dine); CL-387785 (N-[4-[(3-bromophenyl)amino]-6-quinazolinyl]-2-butynamide-); EKB-569 (N-[4-[(3-chloro-4-fluorophenyl)amino]-3-cyano-7-ethoxy-6-quino-linyl]-4-(dimethylamino)-2-butenamide) (Wyeth); AG1478 (Sugen); AG1571 (SU 5271; Sugen); dual EGFR/HER2 tyrosine kinase inhibitors such as lapatinib (GW 572016 or N-[3-chloro-4-[(3 fluorophenyl)methoxy] phenyl]6[5[[[2methyl-sulfonyl)ethyl]amino]methyl]-2-furanyl]-4-quinazolinamine; Glaxo-SmithKline) or cyanoguanidine quinazoline and cyanoamidine quinazolamine derivatives.

The inventions described herein are related in part to the findings described in the Examples (infra). The MSU-1.0 cell strain arose spontaneously in culture when normal human fibroblasts were transfected with the v-myc oncogene. This strain is chromosomally stable and has an infinite lifespan. A clonal derivative of the MSU-1.0 strain, designated MSU-1.1, differs from its precursor in that it can be malignantly transformed with the H-Ras oncogene. Consistently, MSU-1.1 cells that express H-Ras (PH3MT cells) form tumors in athymic mice. To identify novel genes that are involved in human cells becoming malignant, gene chip arrays were used to compare the expression profiles of the MSU-1.1 and PH3MT strains, to the expression profile of the MSU-1.0 strain. Sprouty-2 (spry2) was identified as having elevated expression levels in MSU-1.1 and PH3MT cells compared to MSU-1.0 cells, a finding that was then validated by Northern and Western blotting. It has also been found that several fibrosarcoma and pancreatic cancer cell lines contained elevated levels of Sprouty2 (Example 2).

To determine whether Sprouty2 plays a role in H-Ras transformation, the level of Sprouty2 was down-regulated in PH3MT cells by stably expressing spry2-specific RNAi molecules. Compared to PH3MT cells, cells with decreased Sprouty2 expression formed fewer and smaller colonies in soft agar. Also, the cells that expressed spry2-specific RNAi molecules exhibited an increase in the latency of tumor formation. Accordingly, methods are provided herein for identifying compounds that decrease Sprouty expression or activity in a tumor cell that expresses a Ras oncogene.

To study how Sprouty2 contributes to neoplastic formation, the levels of epidermal growth factor receptor (EGFR) were compared before and after EGF stimulation, in the presence or absence of Sprouty2 expression. PH3MT cells retained the same level of EGFR after EGF stimulation. In contrast, upon EGF stimulation, the levels of EGFR in PH3MT cells with down-regulated Sprouty2 were decreased. This is a similar profile to that seen in MSU-1.1 cells, which have a significantly lower Sprouty2 expression than PH3MT cells. These data also show that, under serum-depriving conditions, the down regulation of Sprouty2 led to a decrease in the activation of ERK. The levels of active H-Ras were not affected by the down regulation of Sprouty2. These results suggest that, in the system described herein, Sprouty2 contributes to malignant transformation by sustaining signaling from the EGFR and the Ras-mitogen activated protein kinase pathways.

Studies show that EGFR signaling is necessary for H-Ras-induced malignant phenotypes (Hamilton et al. (1998) *J. Biol. Chem.* 273:28155-28162; Casanova et al. (2002) *Cancer Res.* 62:3402-3407; Gangarosa et al. (1997) *J. Biol. Chem.* 272: 18926-18931; Martâinez-Lacaci et al. (2000) *Int. J. Cancer,* 88:44-52; Sibilia et al. (2000) *Cell* 102:211-220). Furthermore, H-Ras causes the transcriptional activation of EGFR ligands (e.g., TNFα and amphiregulin), which then, in an autocrine fashion, activate EGFR (Gangarosa et al. (1997) *J. Biol. Chem.* 272:18926-18931; Hamilton et al. (1998, supra)). Herein, it is shown that H-Ras-transformed cells express high levels of Sprouty2, which can sustain the levels and signaling activity of EGFR. This represents an intracellular mechanism by which H-Ras can recruit EGFR during malignant transformation.

EXAMPLES

The invention is further illustrated by the following examples. The examples are provided for illustrative purposes only. They are not to be construed as limiting the scope or content of the invention in any way.

Example 1

Materials and Methods

Cells and Cell Culture

The derivation of the human fibroblast cell line MSU-1.1 has been described (Hurlin et al. (1989) *Proc. Natl. Acad. Sci. U.S.A.* 86:187-191; Morgan et al. (1991) *Exp. Cell Res.* 197: 125-136). The PH2MT and PH3MT cell strains were derived from tumors formed in athymic mice by the injection of MSU-1.1 cells malignantly transformed by an overexpressed H-Ras oncogene (Hurlin et al. (1989) *Proc. Natl. Acad. Sci. U.S.A.* 86:187-191). The SL68 and SL89 cell lines are normal neonatal foreskin-derived fibroblasts, SHAC, HT1080, VIP: FT, and NCI cells were derived from fibrosarcoma patients. The N-Ras-2T and N-Ras-3T cell strains are tumor-derived cell lines originating from MSU-1.1 cells overexpressing the N-Ras oncogene (Wilson et al. (1989) *Carcinogenesis* 10:635-640). The immortalized pancreatic cell ps-1 was obtained from Michigan State University. MIAPaCa-2, AsPc1, CFPAC1, PANC-1, BxPC-3, HPAF-II, Capan-1, and Capan-2 are pancreatic cancer cell lines (available from the American Type Culture Collection, Manassas, Va.) derived from human patients. The cells were cultured in Eagle's Minimal Essential Medium (MEM), supplemented with L-aspartic acid (0.2 mmol), L-serine (0.2 mmol), pyruvate (1 mmol), and 10% supplemented calf serum (Hyclone, Logan, Utah), penicillin (100 units/ml), and streptomycin (100 µg/ml, culture medium) at 37° C. in a humidified incubator with 5% $CO_2$. To select for infected cell strains puromycin (20 µg/ml) was added to the culture medium.

Northern Blot Analysis

Total RNA was extracted from cells with RNAzol™ reagent from Tel-Test, Inc. (Friendswood, Tex.) according to the manufacturer's protocol. Northern blotting was performed according to standard procedures. A spry2-specifc probe was used for the detection of Spry2. Equal loading was determined with a probe specific for GAPDH.

Western Blot Analysis

Whole cell lysates were prepared as described in Lou et al. (2005) *Cancer Res.* 65:1007-1017. The protein content was quantified with Coomassie protein reagent from Pierce (Rockford, Ill.). Whole cell lysate (50 µg) was separated by SDS-PAGE. The protein was transferred to polyvinylidene fluoride membrane (Millipore, Billerica, Mass.), and immunoblotting was carried out using standard techniques. The signal was detected with the SuperSignal® reagent (Pierce). Antibodies against EGFR, ERK, pERK, c-Cbl, and H-Ras were purchased from Santa Cruz Biotechnology, Inc. (Santa Cruz, Calif.); Sprouty2 from Calbiochem (San Diego, Calif.); Pan-Ras from Cytoskeleton, Inc. (Denver, Colo.) and Ku80 from Serotec (Raleigh, N.C.). The Ku80 protein expression was used as a loading control.

Preparation of Spry2-shRNA (siRNA) Constructs

The down-regulation of Sprouty2 in PH3MT cells was carried out with the pSuper.retro system (OligoEngine, Seattle, Wash.). The shRNA (short hairpin RNA) constructs were designed according to the manufacturer's protocol. Briefly, the coding region of Spry2 was analyzed with OligoEngine's RNAi design tool and two 19-nucleotide long regions centered on positions 399 and 492 of the Spry2 coding region were selected as target sites. For each of these target sites, a 65-base pair, double-stranded oligonucleotide was synthesized, which encoded the sense and antisense orientations of the Spry2 target site separated by a hairpin sequence of nine base pairs. The double stranded oligonucleotides were synthesized to contain BgIII and HindIII overhangs. The sequences for the oligonucleotides targeting positions 399 and 492 on the Spry2 coding region were 5'GATCCCCGAGACTGCTAGGATCATCCT-TCAAGAGAGGAGTGATCCTAGCAG CTCTTTTTG-GAAA (SEQ ID NO:1) and 5'GATCCCCGCCACTGAG-CAAGGAAGATTTCAAGAGAATCTTCCTTGCTCAGT GGCTTTTTGGAAA (SEQ ID NO:2), respectively. In addition to the two spry2-specific oligonucleotides, a nonspecific oligonucleotide was synthesized in which the sense and antisense sequences were scrambled. Following their synthesis, the double-stranded oligonucleotides were ligated into the pSuper.retro vector.

Stable Infection

The pSuper.retro vectors encoding the spry2-specifc or the nonspecific shRNA constructs were transiently transfected into the Phoenix packaging cell line by using Lipofectamine™ 2000 from Invitrogen (Carlsbad, Calif.) according to the manufacturer's directions. In each case, 5 µg of DNA and a 1:4 DNA to Lipofectamine™ ratio were used. 48 hrs. post-transfection the medium was collected, centrifuged at 1,500×rpm for 5 mins., and the retrovirus-containing supernatant was collected. One ml of retrovirus-containing medium was mixed with 4 µg/ml polybrene and was added to PH3MT cells that had been plated at a density of 200,000 cells per 60 mm dish 24 hrs. prior to infection. The retrovirus-containing medium was removed after 18 hrs. and the cells were allowed to recover for 30 hrs. 48 hrs. post-infection the cells were passaged into 100 mm dishes at a 1:10 dilution, and 24 hrs. later the infected cells were selected with puromycin. Puromycin-resistant cell strains were isolated, and screened for the down regulation of Sprouty2 with Western blotting.

AG1478 Inhibitor Study

For AG1478 inhibitor studies, cells were plated at a density of 5,000 cells per 60 mm-diameter dish in medium containing 0.1% serum, and were allowed to grow in the presence or absence of AG1478 at a concentration of 6 µM. Cell growth was monitored by measuring the number of cells every two days. Each experimental repetition included at least two replicates for each cell strain analyzed.

Immunoprecipitation Reactions

Generally, in experiments employing immunoprecipitation, whole cell lysates (250 µg) were precleared with an appropriate IgG anbtibody for 30 mins., then incubated with an antibody specific to HRas for 2 hrs., followed by incubation with protein-G for 1 hr. to overnight at 4° C. When an Hras-agarose conjugate was used (Ras-cCbl/CIN85), the lysates were incubated with the agarose conjugate for 3 hrs. to overnight. The immunoprecipitated fraction was washed several times with lysis buffer and assayed by Western blotting. Experiments were generally conducted in replicate, e.g., experiments were repeated 3 to 4 times for those examining Ras-Spry2 and Ras-c-Cbl interactions, and two times for those examining the Ras-CIN85 interaction.

Anchorage Independence Assay

Cells were assayed for their ability to form colonies in agarose as described in Lou et al. (2005) *Cancer Res.* 65:1007-1017. Briefly, 5,000 cells were plated in 0.33% top agarose per 60-mm-diameter dish, and overlaid with 2.5 ml of culture medium. The culture medium was replaced weekly. After 3 weeks the cells were fixed with 2.5% gluteraldehyde, and colonies in random fields were analyzed by using the NIH Image 1.62 software. The number and the size of the each colony was determined with the Quantity One software by Bio-Rad (Hercules, Calif.).

Tumorigenicity Assay

Cells were assayed for their ability to form tumors in athymic mice as described in Lou et al. (2005) *Cancer Res.* 65:1007-1017. The mice were examined weekly for tumor growth, and the tumors were removed when they reached 1 cm in diameter. In the absence of tumor formation six months after the injection, the mice were sacrificed.

Ras Activation Assay

Whole cell lysates (2 mg) were pulled down with Raf-Ras binding domain (RBD) conjugated beads from Cytoskeleton, Inc. (Denver, Colo.) according to the manufacturer's instructions. The pulled down fractions were immunoblotted with an H-Ras specific antibody to determine the level of active H-Ras.

Example 2

Elevated Expression of Spry2 in the H-Ras-Transformed Cells

Figure 1B:
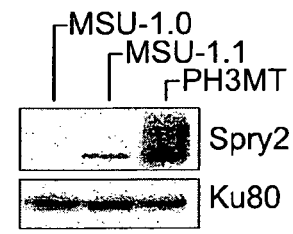
FIG. 1B is a photographic representation of a Western blot depicting the expression of Sprouty2 in immortalized human fibroblasts, MSU-1.0, MSU-1.1, and in PH3MT cells.

The results of a genome-wide comparison between the mRNA expression profiles of the MSU-1.0, MSU-1.1 and PH3MT cell strains revealed that the expression of Spry2 in these strains is low, intermediate, and high, respectively. To verify the results obtained from the gene expression analysis, the expression of Sprouty2 in these cells was examined using Northern and Western blot analysis. Using these methods, an increase in the level of Sprouty2 mRNA was observed that was similar to the levels observed using the genome-wide comparison. There was also a comparable increase in the levels of Sprouty2 protein in these cell lines (FIGS. 1A and 1B). In particular, the expression of Sprouty2 was significantly increased in the cells malignantly transformed by H-Ras$^{V12}$ oncogene (PH3MT) compared to the other cell lines.

Figure 1C:
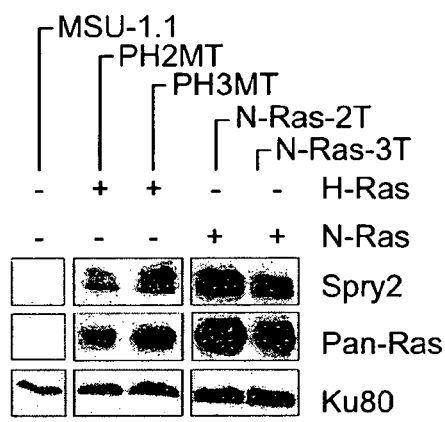
FIG. 1C is a photographic representation of a Western blot in which in MSU-1.1 cells, and cells malignantly transformed by the N-Ras oncogene was stained with antibodies that detect Sprouty2, Pan-Ras, and Ku80.

The increased expression of Sprouty2 in the malignantly transformed cell line suggested that oncogenic transformation of a cell, e.g., by H-Ras, is responsible for the high level of Sprouty2 protein found in PH3MT cells. To determine if the same was true for another oncogenic cell line, one transformed using N-Ras, the levels of Sprouty protein expression were examined in MSU-1.1 cell strains that were malignantly transformed by the N-Ras$^{V12}$ oncogene, i.e., N-Ras-2T and N-Ras-3T (Wilson et al. (1990) *Cancer Res.* 50:5587-5593). N-Ras-transformed cells expressed Sprouty2 at a similar level to that present in the H-Ras-transformed cells, i.e., PH2MT and PH3MT (FIG. 1C).

Figure 1D:
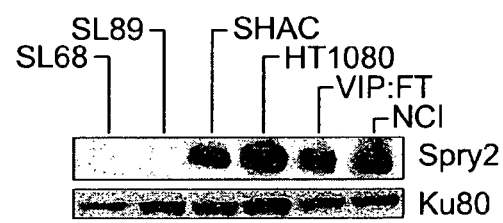
FIG. 1D is a photographic representation of a Western blot in which the expression of Sprouty2 protein in patient derived fibrosarcoma cell lines, and in normal foreskin-derived fibroblast lines (SL68 and SL89) was detected.
Figure 1E:
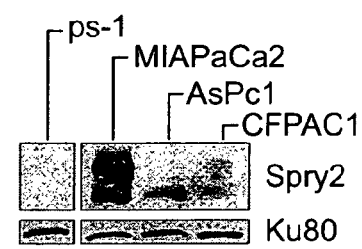
FIG. 1E is a photographic representation of a Western blot in which the expression of Sprouty2 protein in pancreatic carcinoma cell lines and a normal infinite lifespan pancreatic cell line (ps-1) was detected.

The level of expression of Sprouty2 was also examined in a panel of patient-derived fibrosarcoma and patient-derived pancreatic carcinoma cell lines. As shown in FIG. 1D, the four fibrosarcoma cell lines expressed high levels of Sprouty2, whereas the normal foreskin-derived fibroblasts did not express a detectable level of Sprouty2. Only 3 of 7 pancreatic cancer cell lines analyzed expressed Sprouty2 (FIG. 1E). An infinite life span pancreatic cell line, ps-1, did not express Sprouty2. Other pancreatic cancer-derived cell lines (PANC-1, BxPC-3, HPAF-II, Capan-1 and Capan-2) were also analyzed but did not show elevated expression of Sprouty2.

Example 3

Figure 2A:
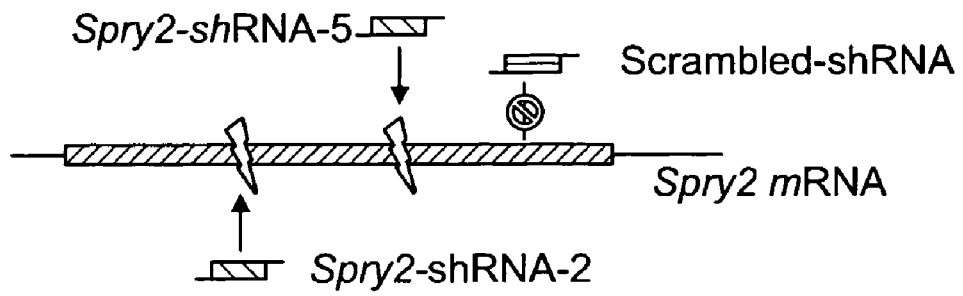
FIG. 2A is a schematic representation illustrating the positions targeted by the Sprouty2-specific shRNA constructs. Spry2-shRNA-2 targets position 399 of the Spry2 coding region, whereas Spry2-shRNA-5 targets position 492 of the Spry2 coding region.

Spry2 Sustains EGFR Levels and Contributes to EGF-Stimulated ERK Activation in H-Ras-Transformed Cells To determine the role of Sprouty2 protein in PH3MT cells, RNA interference (RNAi) was used to down-regulate the expression of Sprouty2 in these cells. The RNAi molecules were designed to target position 399 or position 492 of the Sprouty2 coding region. A scrambled RNAi molecule that does not target Sprouty2 was included as a control (FIG. 2A). The RNAi molecules were stably introduced in the PH3MT cells as described supra, in brief, by employing a retroviral vector designed to express short hairpin RNA (shRNA) molecules. Cell stains expressing a vector without an shRNA molecule (PH3MT-VC, vector control), or a vector encoding a nonspecific shRNA molecule (PH3MT-SC, scrambled control), were used as controls. Two strains of cells were identified that expressed the Sprouty2-specific shRNA molecule targeting position 399 (PH3MT-2A3 and PH3MT-2B9), as well as a cell strain expressing the Sprouty2-specific shRNA molecule targeting position 492 (PH3MT-5A3). The PH3MT-2A3 and PH3MT-2B9 cell strains were derived with Spry2-shRNA-2, whereas the PH3MT-5A3 cell strain was derived with Spry2-shRNA-5.

Figure 2B:
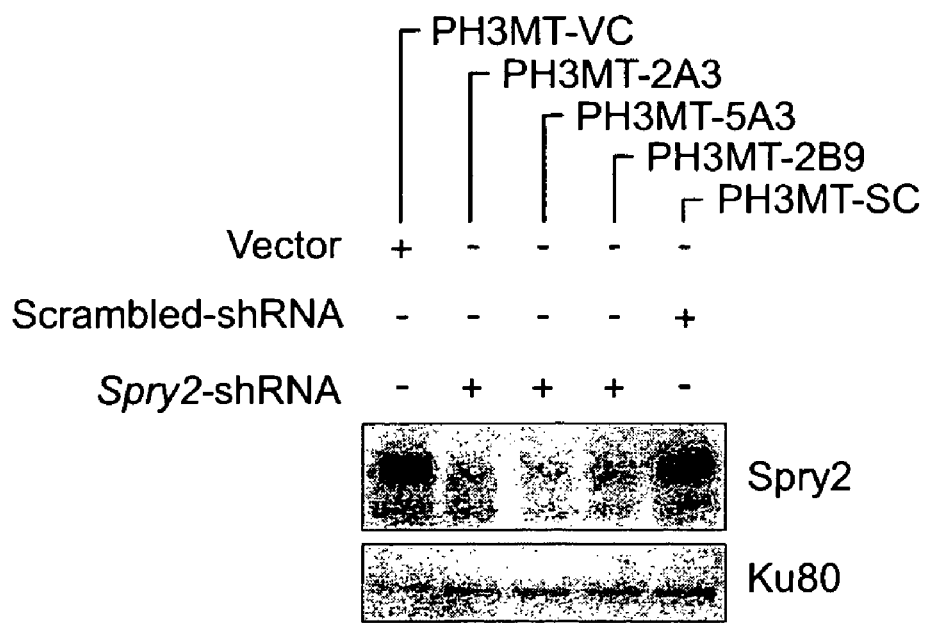
FIG. 2B is a photographic representation of a Western blot in which PH3MT cell strains stably expressing the indicated constructs were analyzed by Western blotting.

The ability of these shRNA molecules to down-regulate Sprouty2 was evaluated by Western blotting (FIG. 2B). The cell strains expressing shRNA molecules specific for either position of the Spry2 coding region were found to express lower levels of the Sprouty2 protein compared Sprouty2 expression in the control cell strains.

Sprouty2 interacts with c-Cbl (E3 ubiquitin ligase, and the interaction prevents the ubiquitination and subsequent degradation of EGFR, and thereby sustains the signaling activity of this receptor (Wong et al. (2001) *J. Biol. Chem.* 276:5866-

Figure 3A:
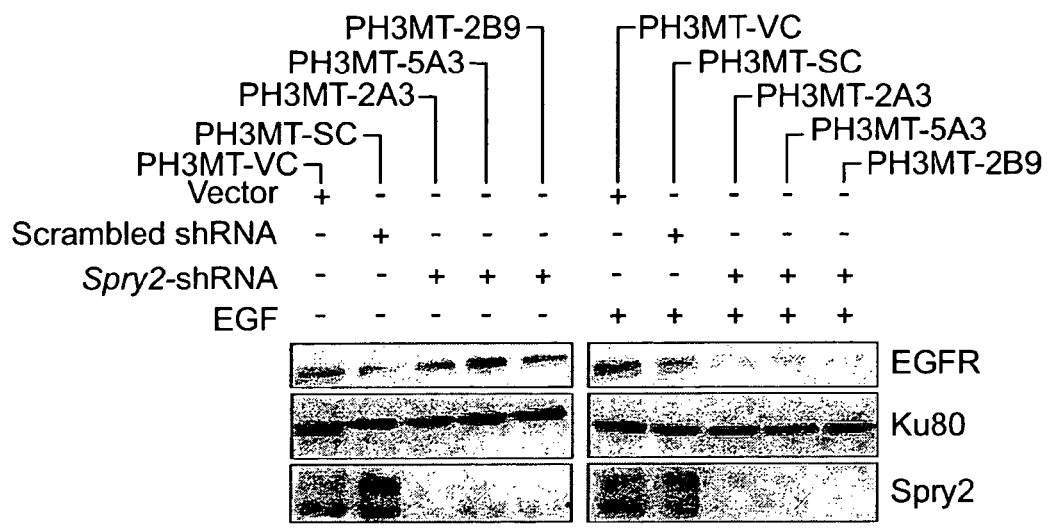
FIG. 3A is a photographic representation of a Western blot showing the expression of EGFR where the indicated cell strains were serum starved for 12 hrs. and then stimulated with EGF (100 ng/ml) for 10 mins.

5875; Egan et al. (2002) *Proc. Natl. Acad. Sci. U.S.A.* 99:6041-6046; Wong et al. (2002) *EMBO J.* 21:4796-4808; Fong et al. (2003) *J. Biol. Chem.* 278:33456-33464; Rubin et al. (2003) *Curr. Biol.* 13:297-307; Mason et al. (2004) *Mol. Biol. Cell* 15:2176-2188). To determine if Sprouty2 has a similar function in H-Ras-transformed cells, the levels of EGFR were compared in the cells with down-regulated Sprouty2 with the levels of the EGFR in the control cells. Because the ubiquitination of EGFR by c-Cbl is dependent on the activation of the EGF receptor (Levkowitz et al. (1999) *Mol. Cell* 4:1029-1040) the cells were serum-deprived and then stimulated with EGF. Upon EGF stimulation, the levels of EGFR in the 3 PH3MT-derived cell strains with down-regulated Sprouty2 were decreased. In contrast, the cell strain containing the empty vector, as well as that expressing a scrambled RNAi, retained the same level of EGFR after EGF stimulation, as they did in the absence of EGF (FIG. 3A). Furthermore, MSU-1.1 cells, which have a lower endogenous level of Sprouty2 expression than do PH3MT cells, also expressed lower levels of EGFR under similar conditions. These data demonstrate that Sprouty2 acts to prevent ubiquitination and subsequent degradation of EGFR in a malignantly transformed cell.

Figure 3B:
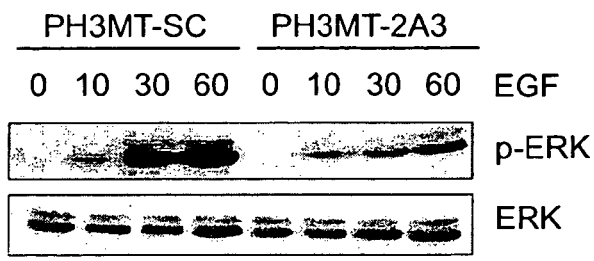
FIG. 3B is a photographic representation of a Western blot depicting the results of experiments in which the indicated cell strains were serum starved for 12 hrs. and then stimulated with EGF (100 ng/ml) for the indicated time periods (shown in minutes) and the activation of ERK determined with a phosphorylation-specific antibody ERK (pERK)-specific antibody.

To determine if the expression of Sprouty2 in PH3MT cells was associated with an increase in the activation of the RAS/MAPK cascade, EGF-induced activation of ERK was examined by Western blotting with a phosphorylation-specific antibody. The cell strain with down-regulated Sprouty2 level (PH3MT-2A3) showed decreased levels of ERK activation, compared to the level found in the cell strain containing the scrambled RNAi (PH3MT-SC) (FIG. 3B). These data demonstrate that the elevated expression of Sprouty2 in H-Ras transformed cells sustains the level of EGFR and contributes to the activation of ERK. Together, these results indicate that Sprouty2 acts as an agonist of RTK signaling in fibroblasts transformed by the H-Ras oncogene. Furthermore, these experiments demonstrate that a decrease in Sprouty in a malignantly transformed cell can decrease the expression or activity of components of a signaling pathway associated with malignancy.

Example 4

Figure 4:
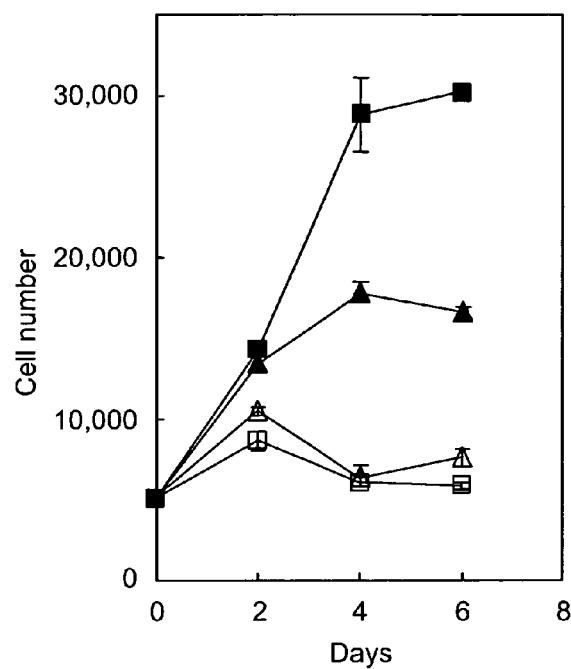
FIG. 4 is a graphic representation illustrating the results of experiments in which MSU-1.1 and PH3MT cells were grown in media with 0.1% serum in the presence (closed triangles and squares, respectively) or absence (opened triangles and squares, respectively) of the selective EGFR inhibitor AG1478 (6 µM).

EGFR Activity and Growth Factor Independence of H-Ras$^{V12}$-Transformed Fibroblasts The activation of Ras oncogenes enables cellular growth in the absence of exogenous growth factors (Medema et al. (1993) *Crit. Rev. Oncog.* 4; Shields et al. (2000) *Trends Cell. Biol.* 10:147-154). To determine if the activity of EGFR is necessary for the growth factor independence of H-Ras-transformed cells, measurements were made to determine the ability of PH3MT cells to grow in the presence of the AG1478 inhibitor, a specific inhibitor of EGFR tyrosine kinase activity (Levitzki et al. (1995) *Science* 267:1782-1788). The inhibition of EGFR activity by AG1478 resulted in a decrease in the ability of H-Ras-transformed cells to grow in medium with reduced serum. This decrease was significantly greater than the corresponding effect of the same inhibitor on the MSU-1.1 cells ($p<0.001$), the cell strain from which the H-Ras transformed cells were derived (FIG. 4). This suggests that intact EGFR activity is required for the growth factor independence of PH3MT.

Sprouty2 is known to interact with several proteins to regulate the MAPK cascade. The interaction of Sprouty2 with c-Cbl prevents EGFR degradation whereas the interaction of Sprouty2 with Grb2 or with Raf inhibits the activation of ERK (Christofori (2003) *Nat. Cell Biol.* 5:377-379; Guy et al. (2003) *J. Cell Sci.* 116:3061-3068; Kim et al. (2004) *Nat. Cell Biol.* 2:281-282). The finding described herein that Sprouty2 sustains the level of EGFR (Example 4) and promotes the activation of ERK in H-Ras-transformed cells (Example 3), indicates that Sprouty2 prevents the c-Cbl-induced down-regulation of EGFR in these cells. This is also supported by findings that Sprouty2 can interact with c-Cbl in Ras-transformed cells, while no interaction between Sprouty2 and Grb2 was detected in these cells.

Example 5

Figure 5:
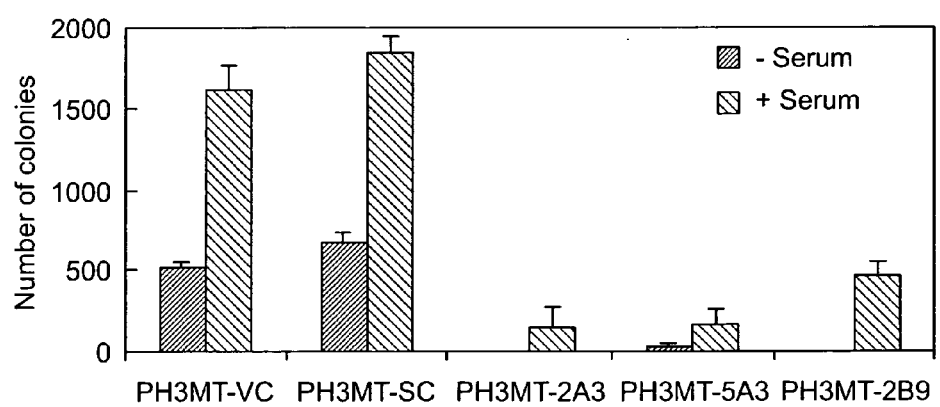
FIG. 5 is a graphic representation illustrating the results of experiments in which the indicated cell lines were allowed to grow in soft agar in the presence of 10% serum (+) or 2.5% serum (−) in the culture medium as described in Example 1 (infra). The graph depicts the number of colonies with a diameter greater than 120 µm in each of the analyzed cell strains.

Sprouty2 Affects Malignant Transformation of and Anchorage-Independent Growth of H-Ras Oncogene-Transformed Fibroblasts The data presented above suggest that Sprouty2 plays a role in H-Ras oncogene-transformation. To determine the contribution of Sprouty2 to this process, the anchorage-independent growth of H-Ras$^{V12}$-transformed cells was examined by determining the ability of the control cell strains, and the three cell strains with down-regulated Sprouty2 to form colonies on 0.33% agarose. The cells with decreased expression of Sprouty2 formed significantly fewer colonies in agarose, compared to the control cells (FIG. 5), demonstrating that Sprouty2 is necessary for this H-Ras-induced oncogenic property, i.e., anchorage independent growth.

When these same cell strains were compared for their ability to form tumors in athymic mice (Table I), the control cell strains (PH3MT-VC and PH3MT-SC) formed 0.5 cm$^3$ tumors in 21 days (12/12 tumors formed per cell strain).

TABLE 1

The Tumorigenicity of the Cell Strains with Down-Regulated Sprouty2

| Cell strain | H-RasV12 | Spry2-shRNA | Tumor incidence$^a$ | Days for tumor to reach 0.5 cm$^3$ volume |
|---|---|---|---|---|
| MSU-1.1 | − | − | 0/6$^b$ | — |
| PH3MT | + | − | 6/6 | 21 |
| PH3MT-VC | + | − | 12/12 | 21 |
| PH3MT-SC | + | − | 12/12 | 21 |
| PH3MT-2A3 | + | + | 0/12 | — |
| PH3MT-5A3 | + | + | 0/12 | — |
| PH3MT-2B9 | + | + | 0/12 | — |

$^a$Ratio of tumors formed to the number of sites injected subcutaneously. The mice were examined for tumor formation for at least 6 months after injection
$^b$10$^7$ MSU-1.1 cells were injected in each site. The rest of the cell strains were injected at one million cells per site.

In contrast, the 3 cell strains with down-regulated expression of Sprouty2 (PH3MT-2A3, PH3MT-5A3, and PH3MT-2B9) failed to form tumors (0/12 tumors formed per cell strain, 6 months after injection). These data provide a strong argument that Sprouty2 is necessary for the transformation of human fibroblasts by the H-Ras oncogene.

Figure 6:
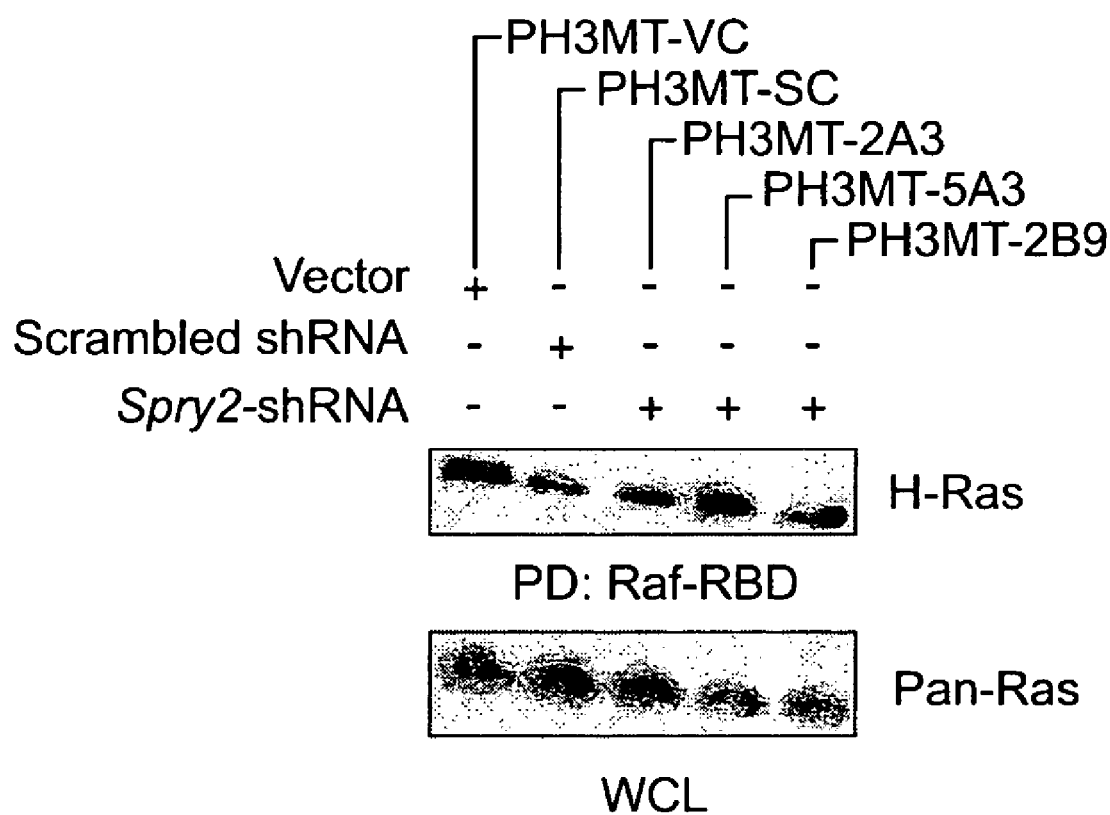
FIG. 6 is a representation of a Western blot depicting the results of experiments in which whole cell lysates from the indicated cell lines were pulled down with RafRBD conjugated beads as described in Example 1 (infra). The total amount of Ras in the whole cell lysate (WCL) is shown.

Given the significant effect that the down-regulation of Sprouty2 has in H-Ras$^{V12}$ transformed cells, an investigation was conducted of whether the down-regulation mitigated H-Ras activation in PH3MT cells. Control cells and cells expressing Sprouty2-specific shRNA constructs were analyzed using a Ras-activation assay. The down-regulation of Sprouty2 had no effect on the levels of active H-Ras (FIG. 6), indicating that Sprouty2 acts at a level other than by affecting Ras activation to modulate H-Ras oncogene-induced malignant transformation.

Example 6

Interaction of Spry2 with HRas

Figure 8A:
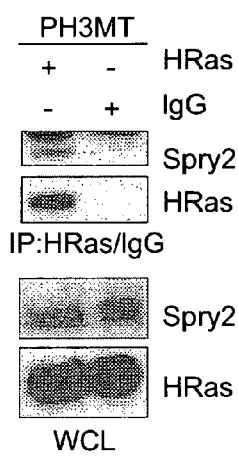
FIG. 8A is a photographic representation of a Western blot depicting the results of experiments in which whole cell lysates (WCL) from HRas-transformed cells (PH3MT) were immunoprecipitated with an antibody specific to HRas or a nonspecific IgG and immunoblotted with the indicated antibodies.

Co-immunoprecipitation experiments were conducted to examine whether Spry2 forms a complex with HRas in HRas-transformed cells (PH3MT). Endogenous Spry2 was found to co-immunoprecipitate with HRas, indicating that that Spry2 interacts with HRas in vivo (FIG. 8A). These data indicate that Spry2 mediates the effect of HRas on EGFR levels via a direct interaction with HRas. Thus, compounds that modulate Spry2 activity, e.g., by decreasing or increasing the interaction between Spry2 and HRas are useful for modulating the effects of Spry2 in a cell. It was also found that the interaction between Spry2 and HRas was enhanced upon stimulation of cells with EGF.

Example 7

Interaction of HRas with c-Cbl and CIN85 in a Spry2-Dependent Fashion

Figure 8B:
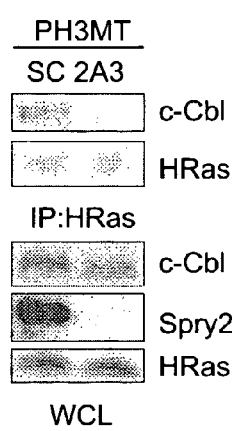
FIG. 8B is a photographic representation of a Western blot depicting the results of experiments in which whole cell lysates from control cells (PH3MT-SC) or cells down-regulated for Spry2 (PH3MT-2A3) were immunoprecipitated with anti-HRas and immunoblotted with c-Cbl, HRas, or Spry2 antibodies.

In PH3MT cells, Spry2 interacts with both HRas and c-Cbl, suggesting that Spry2 mediates an association between HRas and c-Cbl. This interaction was investigated using co-immunoprecipitation methods in which control cells or cells down-regulated for Spry2 expression (PH3MT-2A3) were immunoprecipitated with anti-HRas and immunoblotted to detect with c-Cbl, HRas, or Spry2. The results of the co-immunoprecipitation experiments demonstrated that endogenous c-Cbl can bind to HRas, and that this interaction is abolished in HRas-transformed cells in which Spry2 was down-regulated (FIG. 8B).

Figure 8C:
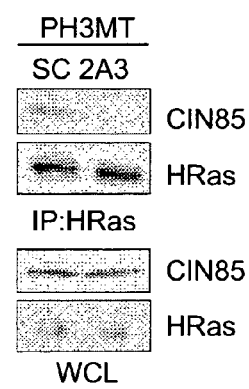
FIG. 8C is a photographic representation of a Western blot depicting the results of experiments in which whole cell lysates from control cells (PH3MT-SC) or cells down-regulated for Spry2 (PH3MT-2A3) were immunoprecipitated with anti-HRas and immunoblotted with the indicated antibodies.

In addition to c-Cbl, Spry2 interacts with CIN85 (Haglund et al. (2005) EMBO Rep. 6:635-41). In particular, Spry2, c-Cbl and CIN85 form a tertiary complex, resulting in the inhibition of EGFR-degradation by the lysosome. In view of this, co-immunoprecipitation experiments were conducted to determine whether HRas also associates with CIN85 in HRas-transformed cells. The results demonstrate that endogenous CIN85 co-immunoprecipitated with HRas in cells expressing Spry2, but not in cells with down-regulated Spry2 (FIG. 8C). These findings indicate that HRas interacts with c-Cbl and CIN85 in a Spry2-dependent manner, and that HRas regulates the turnover of EGFR at the level of the Spry2/c-Cbl/CIN85 complex. Accordingly, compounds that modulate Spry2 expression or activity are useful for modulating the interaction of HRas with c-Cbl and CIN85.

Example 8

Effect of Spry2 Expression in Immortalized Human Fibroblasts

To determine the role of Spry2 in EGF signaling and cancer formation in the absence of activated HRas signaling, Spry2 was stably expressed in cells that were not transformed with HRas (MSU-1.1 cells) (FIG. 9A). MSU-1.1 cells expressing a low level of Spry2-V5 (MSU-1.1S41) were found to exhibit a decrease in EGF-induced ERK activation compared to control cells (MSU-1.1VC) (FIG. 9B). This inhibitory function of Spry2 was less pronounced in MSU-1.1 cells expressing higher levels of Spry2-V5 (MSU-1.1S62), which exhibited an ERK activation profile similar to that of control cells (FIG. 9C). In MSU-1.1S62 cells, Spry2 did not have an effect on the level of EGFR (FIG. 9C). It was also found that the level of Spry2-V5 expression in MSU-1.1S62 cells was similar to the level of endogenous Spry2 expression in PH3MT cells. Exogenous Spry2 inhibited HRas activation in MSU-1.1 cells, an effect that was diminished when there were relatively higher levels of Spry2 expression (FIG. 9D). Consistent with these findings, low levels of exogenous Spry2 expression resulted in a decrease in the ability of MSU-1.1 cells to grow in the absence of growth factors (FIG. 9E, MSU-1.1S41). This inhibitory effect was not observed in cells expressing higher levels of Spry2 (FIG. 9E, MSU-1.1S62). Consistent with these results, control cells and cells expressing low or high levels of exogenous Spry2 failed to form tumors upon injection in athymic mice (Table II), suggesting that independent expression of Spry2 cannot malignantly transform immortalized human fibroblasts.

TABLE II

The tumorigenicity of the cell strains expressing Spry2

| Cell strain | HRas$^{V12}$ | Spry2 | Tumor incidence$^a$ | Days for tumor to reach 0.5 cm$^3$ volume |
|---|---|---|---|---|
| MSU-1.1 | − | − | 0/6$^b$ | — |
| MSU-1.1VCA1 | − | − | 0/6$^c$ | — |
| MSU-1.1VCA6 | − | − | 0/6$^c$ | — |
| MSU-1.1S41 | − | + | 0/6$^c$ | — |
| MSU-1.1S62 | − | ++ | 0/6$^c$ | — |
| PH3MT | ++ | +++$^d$ | 6/6 | 21 |

$^a$Ratio of tumors formed to the number of sites injected subcutaneously. If no tumors arose 6 months after the injection the mice were sacrificed.
$^b$MSU-1.1 derivatives were injected at 10$^7$ cells per site in a 1 cm$^3$ absorbable gelatin sponge that was implanted in the mice one week prior.
$^c$Data reflect a period of 3 months
$^d$Represents endogenous level of Spry2

Example 9

Additional Materials and Methods

The following additional materials and methods were used in Examples 10-14.

Cells and Cell Culture

The derivation of the human fibroblast cell line MSU-1.1 was described in Hurlin et al. (1989) Proc. Nat. Acad. Sci. U.S.A. 86((1)):187-191; and Morgan et al. (1991) Exp. Cell Res. 197((1)):125-36. The PH3MT cell strain used in the studies was derived from tumors formed in athymic mice by the injection of MSU-1.1 cells malignantly transformed by an overexpressed HRas oncogene (Hurlin et al.,1989, supra)). The cells were cultured in Eagle's MEM, supplemented with L-aspartic acid (0.2 mmol), L-serine (0.2 mmol), pyruvate (1 mmol) and 10% supplemented calf serum (Hyclone, Logan, Utah), penicillin (100 units/ml), and streptomycin (100 μg/ml, culture medium) at 37° C. in a humidified incubator with 5% $CO_2$.

Apoptosis Assay

Apoptosis was detected by staining the cells with AnnexinV-FITC (BD Biosciences, San Jose, Calif.) according to manufacturer's recommendations. Briefly, cells were plated at a density of 2×10$^5$ cells/60 mm-dish. 16 hours after plating, the cells were irradiated with UV at a dose of 30-60 J/m$^2$ and incubated at 37° C. under normal culture conditions for varying time periods. Subsequently, the cells were collected, washed twice with AnnexinV binding buffer and incubated with AnnexinV-FITC at room temperature for 15 mins. The cells were also stained with propidium iodide (PI) to distinguish between live and dead cells. AnnexinV-FITC positive cells were determined by flow cytometry under standard conditions. Cells that stained positively for AnnexinV were considered apoptotic, while cells that were positive for both annexinV and PI were not considered apoptotic. All experiments were repeated at least three times.

Western Blotting

Whole cell lysates were prepared as described in Lou et al. ((2005) *Cancer Res.* 65:1007-1017). Protein concentration was quantified with Coomasie protein reagent from Pierce (Rockford, Ill.). Whole cell lysates (50 μg) were separated by SDS-PAGE. The electrophoresed proteins were transferred to a polyvinylidene fluoride membrane (Millipore, Billerca, Mass.), and immunoblotted using standard techniques. Antibodies against pp85, p85, c-Cbl, Mdm2, p53 and H-Ras were purchased form Santa Cruz (Santa Cruz, Calif.); Spry2 from Calbiochem (San Diego, Calif.); pAkt and Akt from Cell Signaling (Danver, Mass.) and Ku80 from Serotec (Raleigh, N.C.). Ku80 protein was used as a loading control. Label signals were detected with the SuperSignal reagent (Pierce, Rockford, Ill.).

Rac1 Activation

Pull-down assays were performed using whole cell lysates (2 mg). The lysates were pulled down with PAK-Cdc42/Rac1 interacting region (CRIB)-conjugated beads from Cytoskeleton (Denver, Colo.) using methods provided by the manufacturer. The pulled down fractions were immunoblotted with a Rac1-specific antibody to determine the level of active H-Ras in selected fractions. These experiments were repeated 3 times in H-Ras-transformed cells and twice in immortalized fibroblasts.

Stress Fiber Staining

Stress fibers were detected with Alexa-fluor 488 conjugated phalloidin stain from Invitrogen (Carlsbad, Calif.), which was used according to the manufacturer's instructions. Briefly, cells at log phase were fixed in 10% normal buffered formalin solution for 10 mins. The fixed cells were washed twice in phosphate buffered saline (PBS), and then treated with 0.1 Triton X-100 in PBS for 3-5 mins. at room temperature. Subsequently, the cells were incubated with blocking solution (1% BSA in PBS) for 20 mins. at room temperature. Finally, the cells were incubated with phalloidin stain for 30 mins. and analyzed by fluorescent microscopy.

Immunoprecipitation Reactions

For immunoprecipitations, whole cell lysates (250 μg-500 μg) were precleared with an appropriate IgG antibody for 30 mins., incubated with an antibody specific to H-Ras for 2 hrs., followed by incubation with protein-G for 1 hr. to overnight at 4° C. In experiments using an H-Ras-agarose conjugate, the lysates were incubated with the agarose conjugate for 3 hrs. to overnight. The immunoprecipitated fraction was washed several times with lysis buffer and assayed by Western blotting. Generally, experiments were repeated three times.

Example 10

Effect of H-Ras Oncogene-Transformation on DNA Damage-Induced Apoptosis

Ras protects NIH3T3 fibroblasts from apoptosis induced by DNA-damage (Franke et al. (2003) *Oncogene* 22:8983-98). Experiments were conducted to determine whether this effect was produced in an H-Ras-transformed cell strain (PH3MT), which has a higher expression of Spry2 compared to its parental cell strain (MSU-1.1) (FIG. 10A). In these experiments, both MSU-1.1 and PH3MT cells were plated at a density of $2 \times 10^5$ cells per dish and allowed to grow overnight. The cells were stimulated with UV and allowed to grow under normal conditions for 4 hrs., then were stained with AnnexinV. The percentage of cells undergoing apoptosis was assayed by staining the cells with AnnexinV-FITC, and analyzing the stained cells using flow cytometry.

Oncogenic H-Ras was found to desensitize immortalized human fibroblasts to early apoptotic events induced by DNA damage (FIG. 10B). These data demonstrate that other H-Ras transformed cells can be used in assay Spry2 effects related to functions and gene expression in such transformed cells. They also demonstrate that such cells are suitable for certain embodiments of the invention, e.g., identifying compounds that modulate effects of Spry2.

It was also found that a cell strain derived from the transformation of MSU-1.1 cells with another Ras oncogene, N-Ras, which expresses high levels of Spry2, was resistant to UV-induced apoptosis. This indicates that the ability to suppress this type of apoptosis process is shared among these Ras isoforms. Therefore, compounds that reduce expression or activity of Spry2, thereby increasing sensitivity to UV-induced apoptosis can be useful generally in Ras-transformed cells.

PI3K is a lipid kinase that phosphorylates phosphoinositides on the 3' position of the inositol ring (Carpenter et al. (1996) *Biochim. Biophys. Acta* 1288:M11-16; Franke et al. (1997) *Cell*, 88:435-437. The enzyme consists of two subunits; a regulatory subunit, p85 and a catalytic subunit, p110. The regulatory subunit interacts with phosphorylated tyrosine residues on activated growth factor receptors (Okkenhaug et al. (2001) *Sci. STKE* (65):PE1; Otsu et al. (1991) *Cell* 65:91-104). The association of p85 with activated growth factor receptors recruits the catalytic subunit to the plasma membrane, were it can phosphorylate phosphoinositides. The p110 catalytic subunit of PI3K interacts with GTP-bound Ras, a process that also results in the activation of PI3K (Rodriguez-Viciana et al. (1996) *Embo J.* 15:2442-2451). Activated PI3K converts $PI(4,5)P_2$ into $PI(3,4,5)P_3$, which activates several effector proteins, including the serine/threonine kinase Akt (Alessi et al. (1996) *Embo J.* 15(23):6541-6551). Akt phosphorylates a number of substrates, which regulate cellular survival pathways. Akt substrates include, but may not be limited to, BAD, NFκB and Mdm2 (Datta et al. (1999) *Genes Dev.* 13:2905-2927; Mayo et al. (2001) *Proc. Natl. Acad. Sci. U.S.A.* 98:11598-11603).

Because PI3K activity is necessary for the activation of survival pathways downstream of Ras, as well as for the transformation of human cells by Ras oncogene (Franke et al. (2003) *Oncogene* 22:8983-8998), experiments were done to determine whether PI3K activity is also necessary for the resistance of HRas-transformed cells to DNA damage induced apoptosis was investigated. In these experiments, UV-induced apoptosis was assayed in cultures of HRas-transformed cells in the presence or absence of 50 nm Wortmannin, an inhibitor of PI3K.

In the absence of Wortmannin treatment, only a small percentage of HRas-transformed cells underwent DNA-damage induced apoptosis (FIG. 10C). However, in the presence of Wortmannin treatment, the percentage of cells undergoing apoptosis was increased (FIG. 10C). This indicates that the ability of HRas to protect human fibroblasts from UV-induced apoptosis is at least in part dependent on PI3K activity. These data also indicate that compounds that stabilize or increase PI3K activity are useful for protecting cells from UV-induced apoptosis. Compounds that decrease PI3K activity are useful for increasing the sensitivity of cells to UV-induced apoptosis.

Treatment of the cells with AG1478, a selective inhibitor of EGFR, also increased the number of Ras-transformed cells undergoing apoptosis in response to UV radiation, suggesting that EGFR signaling is also important for the ability of HRas to protect cells from UV-induced apoptosis. These data also indicated that compounds that stabilize or increase EGFR activity are useful for protecting cells from UV-induced apoptosis.

Because Rac1 can also have a protective effect against UV-induced apoptosis (Murga et al. (2002) *Oncogene* 21(2): 207-216), it was determined whether Rac1 activity is necessary for the inhibition of UV-induced apoptosis in HRas-transformed cells (e.g., PH3MT cells). Two PH3MT-derrived cell lines, PH3MT-RC1, which expresses a dominant negative form of Rac1 (Rac1$^{N17}$), and PH3MT-VC, which expresses an empty vector (FIG. 10D), were analyzed for induction of apoptosis under the same conditions as those described above. The cell line expressing Rac1$^{N17}$ displayed enhanced apoptosis compared to the control cell line (FIG. 10E). These data indicate that Rac1 is also necessary for the HRas-transformed cells to resist UV-induced apoptosis. Accordingly, these data also indicate that compounds that stabilize or increase Rac1 activity are useful for protecting cells from UV-induced apoptosis. Cells that decrease Rac1 expression or activity are useful for increasing sensitivity of a cell, e.g., a Ras-transformed cell to UV-induced apoptosis.

Example 11

Effect of Spry2 on the Activation of the PI3K Pathway in HRas-Transformed Cells

Figure 11A:
FIG. 11A is a photographic representation of a Western blot depicting the results of an experiment in which whole cell lysates from HRas-transformed cells (PH3MT) that were stably infected with a vector encoding a scrambled shRNA (PH3MT-SC), or a vector encoding a Spry2-specific shRNA were analyzed by Western blotting to determine the expression of Spry2.
Figure 11A:
Figure 11A:
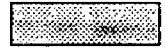

PI3K activation involves recruitment of PI3K to phosphotyrosine residues on the cytoplasmic tail of activated receptor tyrosine kinases (RTKs), a process that is mediated by the SH2 domain of the p85 subunit (Okkenhaug et al. (2001) *Sci STKE* 2001(65):PE1). Because, as shown herein, Spry2 sustains the levels of EGFR in HRas-transformed cells, which activates PI3K (Miller et al. (1995) *J. Virol.* 69(7):4390-4398; Okano et al. (2000) *J. Biol. Chem.* 275(40):30934-30942; Sithanandam et al. (2005) *Am. J. Respir. Cell Mol. Biol.* 33(5):490-499; Stein et al. (2000) *Mol. Med. Today* 6(9):347-357; Wang et al. (2003) *J. Biol. Chem.* 278(46):45737-45745), the question of whether Spry2 contributes to the activation of PI3K was investigated. To test whether this is the case, two cell lines were analyzed; a PH3MT-derived cell strain in which Spry2 has been down-regulated by the expression of a spry2-specific shRNA (PH3MT-2A3), and a control PH3MT cell strain expressing a scrambled shRNA (PH3MT-SC)(FIG. 11A). Because the activation of PI3K correlates with the level of p85 phosphorylation, the level of phosphorylated p85 in control cells and in cells with down regulated Spry2 was assayed (Chen et al. (2001) *J. Biol. Chem.* 276(37): 34617-34623; Tiganis et al. (1999) *J. Biol. Chem.* 274(39): 27768-27775).

Figure 11B:
FIG. 11B is a photographic representation of a Western blot depicting the results of an experiment in which control cells (PH3MT-SC) and cells with down-regulated Spry2 (PH3MT-2A3) were analyzed with the indicated antibodies.
Figure 11B:
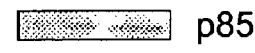
Figure 11B:
Figure 11B:
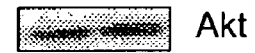

It was found that down-regulation of Spry2 in HRas-transformed cells resulted in a decrease in the level of p85 phosphorylation (FIG. 11B). This finding is consistent with the finding disclosed above that Spry2 can sustain EGFR signaling.

Because Spry2 sustains the activation of PI3K the effect of Spry2 down-regulation in the activation of Akt was examined. Akt is a downstream effector of PI3K. It was found that cells expressing Spry2 had higher levels of phosphorylated Akt compared to the cells with down-regulated Spry2 (FIG. 11B).

This indicates that Spry2 sustains the activation of the PI3K/Akt pathway in HRas-transformed cells. Accordingly, compounds that modulate Spry2 can be useful for modulating the PI3K/Akt pathway.

Example 12

Effect of Spry2 on the Activation of Rac1 in HRas-Transformed Cells

Figure 12A:
FIG. 12A is a photographic representation of the results of a pull-down assay in which whole cell lysates from control cells (PH3MT-SC) and cells with down-regulated Spry2 (PH3MT-2A3) were pulled down with PAK-CRIB (Cdc42- and Rac1-interacting domain)-conjugated beads. The amount of Rac1 that was bound to the beads (Upper panel) and the amount of Rac1 present in whole cell lysates (WCL) (lower panel) is shown.

To determine whether Spry2 plays a role in the activation of Rac1, a Rac1 activation assay was carried out to determine the level of activated Rac1 in control HRas-transformed cells (PH3MT-SC) and in HRas-transformed cells with down regulated Spry2 (PH3MT-2A3). The HRas-transformed cell strain with endogenous levels of Spry2, contained a significantly higher level of active Rac1, compared to cell strain with down-regulated Spry2 expression (FIG. 12A).

Figure 12B:
FIG. 12B is a representation of a photomicrograph of the indicated cell strains stained with Alexa-fluor 488-conjugated Phalloidin stain.

One function of Rac1 is to inhibit stress fiber formation (Burridge et al. (2004) *Cell* 116(2): 167-179). To further investigate whether Spry2 contributes to Rac1 activation in HRas-transformed cells, stress fiber formation was examined in control cells (PH3MT-SC) and in cells with down-regulated Spry2 (PH3MT-2A3). Cells with decreased Spry2 expression contained more pronounced stress fibers compared to cells with endogenous levels of Spry2. This is consistent with the lower level of Rac1 activation in these cells (FIG. 12B). Accordingly, one assay that can be used to analyze the effects of a compound that affects Spry2 expression or activity is to assay stress fiber formation in the presence and absence or a compound in a cell that can express Rac1.

Figure 11C:
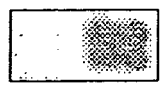
FIG. 11C is a photographic representation of a Western blot depicting the results of an experiment in which whole cell lysates from non-tumorigenic, immortalized human fibroblasts (MSU-1.1) were stably transfected with an empty vector (MSU-1.1-VC) or a vector encoding V5-tagged Spry2 (MSU-1.1-S62) were analyzed for Spry2 expression.
Figure 11C:

To determine whether Spry2 has an effect on Rac1 activation independently of Ras, a stable cell strain of immortalized human fibroblasts expressing V5-tagged Spry2 (MSU-1.1-S62) (FIG. 11C) was established. MSU-1.1 cells are the same precursor cells used to generate the HRas-transformed cells in the studies reported herein.

Figure 12C:
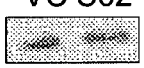
FIG. 12C is a photographic representation of the results of a pull-down assay in which an MSU-1.1 cell strain expressing exogenous Spry2 (MSU-1.1-S62), and a MSU-1.1 cell strain expressing an empty vector (MSU-1.1-VC) were analyzed as in FIG. 12A.

It was found that Spry2 expression did not have a significant effect on Rac1 activation in these cells (FIG. 12C). These data indicate that Spry2 cannot activate Rac1 independently of HRas-transformation.

To determine the role of Spry2 in the activation of Rac1 by HRas, the Ras-Tiam1 interaction was investigated. Tiam1 is a guanine nucleotide releasing factor for Rac1, which has been shown to interact with Ras, a process that leads to Rac1 activation (Lambert et al. (2002) *Nat. Cell Biol.* 4(8):621-625). To identify the role of Spry2 in this interaction, co-immunoprecipitation experiments were carried out using antibodies that bind to HRas and Tiam1. The studies were carried out using control cells (PH3MT-SC) and cells that were down-regulated Spry2 (PH3MT-2A3).

Figure 12D:
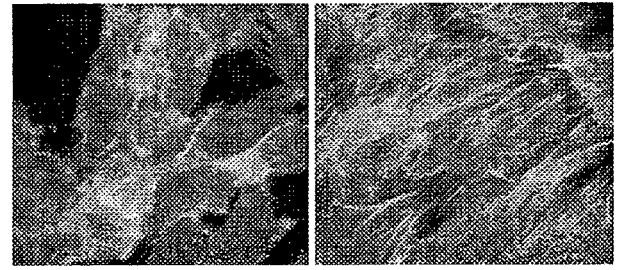
FIG. 12D is a photographic representation of the results of an assay in which whole cell lysates from the indicated cell strains were immunoprecipitated with an antibody specific to HRas, then immunoblotted with the indicated antibodies.

In these experiments, the amount of endogenous Tiam1 that co-immunoprecipitated with HRas was reduced in the in cells that had down-regulated Spry2 expression compared to the amount of Tiam 1 that co-precipitated in control cells (FIG. 12D). Thus, Spry2 enhanced the level of active Rac1 in HRas-transformed cells, in part by modulating the interaction between HRas and Tiam1. Accordingly, a compound that can modulate (e.g., increase or decrease) Spry2 expression or activity can modulate (e.g., increase or decrease) the interaction between Hras and Tiam1 in a cell.

Example 13

Effect of Spry2 on the Induction of Apoptosis in Response to DNA Damage

As described herein, it was found that Spry2 contributes to the activation of PI3K and Rac1, both of which are responsible for the ability of HRas to inhibit apoptosis in response to DNA damage in PH3MT cells. The question of whether Spry2 itself is required for such activity was investigated. To test this, the amount of apoptosis in response to UV damage in HRas-transformed cells were in which Spry2 was down-regulated (PH3MT-2A3) were compared to control H-Ras-transformed cells (PH3MT-SC) that were treated in the same way.

Figure 13A:
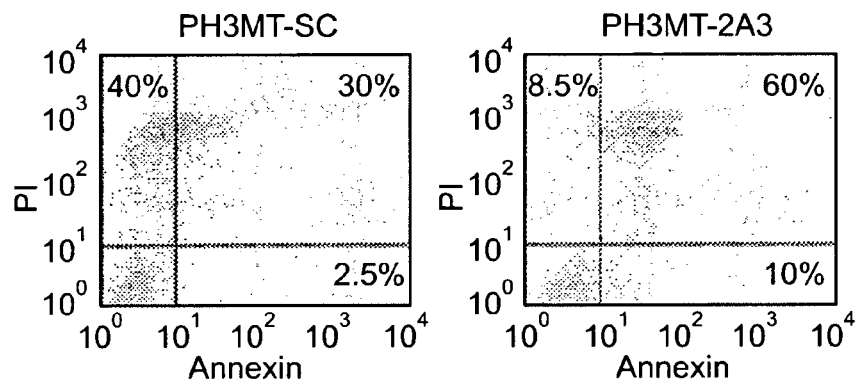
FIG. 13A is a representation of a flow cytometry plot of the results of experiments in which control HRas-transformed cells (PH3MT-SC), as well as HRas-transformed cells with down regulated Spry2 (PH3MT-2A3) were analyzed as in FIG. 10B.

The results of these experiments demonstrated that cells with down regulated Spry2 exhibited an increase in the percentage of cells undergoing apoptosis in response to UV damage. This indicates that Spry2 is necessary for HRas$^{V12}$ to protect the cells from UV-induced apoptosis (FIG. 13A). The down-regulation of Spry2 had no effect on the induction of apoptosis when the cells were cultured under normal conditions.

Figure 13B:
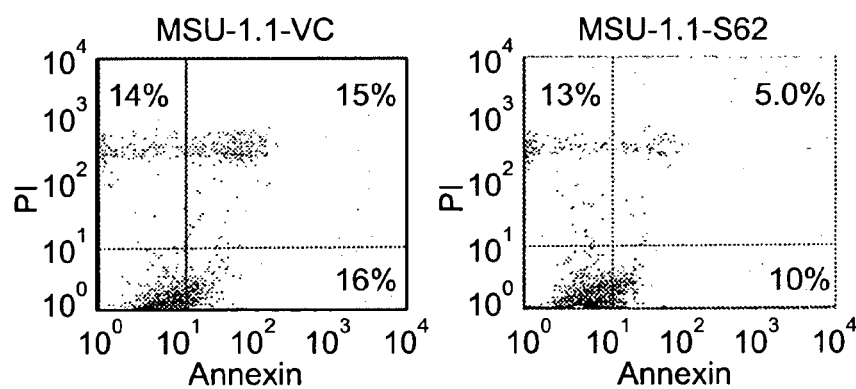
FIG. 13B is a representation of a flow cytometry plot of the results of experiments in which control immortalized fibroblasts (MSU-1.1-VC) and immortalized fibroblasts expressing Spry2-V5 (MSU-1.1-S62) were analyzed as in FIG. 1B.

To determine whether Spry2 plays a role in the regulation of apoptosis independently of HRas transformation, the level of apoptosis induced by UV-stimulation was examined in MSU-1.1-derived cell strains expressing either exogenous Spry2-V5 (MSU-1.1-S62) or an empty vector (MSU-1.1-VC). Consistent with the role of Spry2 in HRas-transformed cells, expression of Spry2 in immortalized human fibroblasts (MSU-1.1-S62) diminished the ability of these cells to undergo apoptosis in response to UV-induced DNA damage (FIG. 13B). This is the same type of response induced by expression of HRas oncogene in the same cell line (see FIG. 10B). Thus, Spry2 plays a role in the regulation of apoptosis that is independent of HRas transformation.

Example 14

Effect of Spry2 on the MDM2/p53 Pathway

The MDM2/p53 pathway plays a critical role in UV-induced apoptosis (Lakin et al. (1999) *Oncogene* 18(53):7644-7655). Akt phosphorylates MDM2 on serine residue 166, resulting in the stabilization of MDM2 (Ogawara et al. (2002) *J. Biol. Chem*, 277(24):21843-21850). This enhances the ubiquitination of p53 by MDM2, which is followed by degradation of the p53. Because Spry2 prevents UV-induced apoptosis while sustaining the activation of Akt in HRas-transformed fibroblasts, it was proposed that Spry2 promotes the Akt-mediated stabilization of Mdm2 and subsequent decrease in the level of p53 protein. To test this proposal, the amount of MDM2 phosphorylated at Ser166 was determined in a cell strain with down regulated Spry2 (PH3MT-2A3) and in a control cell strain (PH3MT-SC).

It was found that the cell strain with down-regulated Spry2 exhibited a decrease in the amount of MDM2 that is phosphorylated at Ser166 (FIG. 14A), which correlated with the decreased in the level of activated Akt in these cells. It was also found that the levels of p53 were increased in the cell strain with down-regulated Spry2 (FIG. 14A).

Next the stability of MDM2 and p53 in control cells and in cells with decreased expression of Spry2 was examined. The cells were irradiated with UV and assayed to determine the protein expression levels of MDM2 and p53.

It was found that HRas-transformed cells with down-regulated Spry2 (PH3MT-2A3) exhibited a decrease in the level of MDM2 following UV treatment compared to control HRas-transformed cells (PH3MT-SC) (FIG. 14B). This finding is consistent with the decrease in the activation of Akt, and the decrease in the phosphorylation that stabilizes MDM2 in the cell strain with down-regulated Spry2. The level of p53 was higher in the cell strain with down-regulated Spry2 compared to the control cell strain, even though both cell strains exhibited an increase in the amount of p53 in response to UV stimulation (FIG. 14B). These findings are consistent with the ability of Spry2 to inhibit UV-induced apoptosis in HRas-transformed cells.

Because it was found that Spry2 prevented UV-induced apoptosis upon expression in immortalized human fibroblasts (MSU-1.1) (see FIG. 13B), the effect of Spry2 expression on the level of p53 was examined in these cells. Consistent with the function of Spry2 in HRas-transformed cells, the MSU-1.1 cell strain expressing Spry2 (MSU-1.1-S62) exhibited a decrease in the level of p53 compared to the control cell line (MSU-1.1-VC) (FIG. 14C).

Experiments were also conducted to determine whether Rac1 plays a role in the ability of Spry2 to regulate the MDM2/p53 pathway in HRas-transformed cells. Since the down regulation of Spry2 in HRas-transformed cells results in a decrease in the level of active Rac1, GFP-tagged, constitutively active Rac1 (Rac$^{V12}$) was stably expressed in a cell strain with down-regulated Spry2 (PH3MT-2A3). When compared to a cell strain expressing GFP alone (2A3-VC), the cell strain expressing GFP-Rac1$^{V12}$ (2A3-R1) did not exhibit a difference in the level of MDM2 or p53 under normal culture conditions (FIG. 14D) or following UV-treatment of the cells. These data indicate that the effect of Spry2 on the MDM2/p53 pathway is independent of Rac1. Accordingly, UV-related apoptosis can be increased by contacting a cell with both a compound that decreases Spry2 expression or activity, and, in some cases, also in combination with a compound that stabilizes or increases Rac1 expression or activity.

Taken together, the Examples demonstrate that Spry2 is an important mediator of survival signals induced by oncogenic HRas. Accordingly, compounds that ameliorate Spry2 expression or activity are useful for modulating survival signals that are subject to induction by oncogenic Hras. In general, the assays for the effects of Spry2 on survival signals can be used to identify or confirm the identify of a compound that can modulate Spry2 expression or activity.

EQUIVALENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A composition comprising a Sprouty2 siRNA that decreases Sprouty2 expression or activity, wherein the Sprouty2 siRNA comprises a sequence expressed from a vector sequence comprising SEQ ID NO: 1, wherein the sequence is at least 16 nucleotides in length.

2. The composition of claim 1, wherein the Sprouty2 siRNA comprises an RNA sequence that corresponds to 30 nucleotides of the DNA sequence of SEQ ID NO: 1.

3. The composition of claim 1, wherein the Sprouty2 siRNA comprises an RNA sequence that corresponds to 25 nucleotides of the DNA sequence of SEQ ID NO: 1.

4. The composition of claim 1, wherein the Sprouty2 siRNA comprises an RNA sequence that corresponds to 20 nucleotides of the DNA sequence of SEQ ID NO: 1.

5. The composition of claim 1, wherein the Sprouty2 siRNA comprises an RNA sequence that corresponds to 16 nucleotides of the DNA sequence of SEQ ID NO: 1.

6. The composition of claim 1, wherein the Sprouty2 siRNA consists of an RNA sequence that corresponds to 30 nucleotides of the DNA sequence of SEQ ID NO: 1.

7. The composition of claim 1, wherein the Sprouty2 siRNA consists of an RNA sequence that corresponds to 25 nucleotides of the DNA sequence of SEQ ID NO: 1.

8. The composition of claim 1, wherein the Sprouty2 siRNA consists of an RNA sequence that corresponds to 20 nucleotides of the DNA sequence of SEQ ID NO: 1.

9. The composition of claim 1, wherein the Sprouty2 siRNA consists of an RNA sequence that corresponds to 16 nucleotides of the DNA sequence of SEQ ID NO: 1.

10. A pharmaceutical composition comprising (i) the composition of any one of claims 1-9, and (ii) a pharmaceutical carrier.

* * * * *